United States Patent
Corte et al.

(10) Patent No.: US 7,459,564 B2
(45) Date of Patent: Dec. 2, 2008

(54) SUBSTITUTED BIARYL COMPOUNDS AS FACTOR XIA INHIBITORS

(75) Inventors: James R. Corte, Lawrenceville, NJ (US); Mimi L. Quan, Yardley, PA (US); Joanne M. Smallheer, Yardley, PA (US); Donald J. Pinto, Churchville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 213 days.

(21) Appl. No.: 11/330,528

(22) Filed: Jan. 12, 2006

(65) Prior Publication Data

US 2006/0154915 A1 Jul. 13, 2006

Related U.S. Application Data

(60) Provisional application No. 60/643,759, filed on Jan. 13, 2005.

(51) Int. Cl.
| | |
|---|---|
| C07D 261/20 | (2006.01) |
| C07D 231/56 | (2006.01) |
| C07D 215/00 | (2006.01) |
| C07D 237/30 | (2006.01) |
| C07D 239/72 | (2006.01) |
| A01N 43/80 | (2006.01) |
| A01N 43/56 | (2006.01) |
| A01N 43/42 | (2006.01) |
| A01N 43/58 | (2006.01) |
| A01N 43/54 | (2006.01) |

(52) U.S. Cl. .............. 548/241; 548/361.1; 546/152; 546/165; 544/237; 544/283; 514/379; 514/403; 514/311; 514/248; 514/266.1

(58) Field of Classification Search .......... 514/248, 514/266.1, 311, 379, 403; 544/237, 283; 546/152, 165; 548/241, 361.1
See application file for complete search history.

(56) References Cited

U.S. PATENT DOCUMENTS

| 6,645,939 B1 | 11/2003 | Durette et al. |
|---|---|---|
| 2004/0106621 A1 | 6/2004 | Wu et al. |
| 2004/0138268 A1 | 7/2004 | Boy et al. |
| 2004/0220206 A1 | 11/2004 | Smallheer et al. |
| 2004/0235847 A1 | 11/2004 | Quan et al. |
| 2005/0228000 A1 | 10/2005 | Smallheer et al. |
| 2005/0282805 A1 | 12/2005 | Hangeland et al. |
| 2006/0009455 A1 | 1/2006 | Corte et al. |

FOREIGN PATENT DOCUMENTS

| EP | 1258473 A | 11/2002 |
|---|---|---|
| EP | 1314719 A | 5/2003 |
| WO | WO00/39115 A | 7/2000 |
| WO | WO 01/27079 | 4/2001 |
| WO | WO 01/49288 | 7/2001 |
| WO | WO02/76929 A | 3/2002 |
| WO | WO2004/047738 A | 6/2004 |
| WO | WO2004/060281 A | 7/2004 |

OTHER PUBLICATIONS

Deng et al., Bioorg. Med Chem Lett, 16, 2006, 3049-3054.*
Arendsen et al., caplus an 1997:41540.*
Bouma, B.N. et al., "Thrombin-Activatable Fibrinolysis Inhibitor (TAFI, Plasma Procarboxypeptidase B, Procarboxypeptidase R, Procarboxypeptidase U", Thrombosis Research, vol. 101, pp. 329-354 (2001).
Colman, R.W., Chapter 6: "Contact Activation Pathway: Inflammatory, Fibrinolytic, Anticoagulant, Antiadhesive, and Antiangiogenic Activities", Hemostasis and Thrombosis: Basic Principles and Clinical Practice, 4th Ed., Lippincott Williams & Wilkins, publ., Colman, R.W. et al., eds., pp. 103-121 (2001).
Gailani, D., "Activation of Factor IX by Factor XIa", Trends Cardiovasc. Med., vol. 10, No. 5, pp. 198-204 (2000).
Gailani, D., "Gene Targeting in Hemostasis. Factor XI", Frontiers in Bioscience, vol. 6, pp. d201-207 (2001).
Gailani, D. et al., "A murine model of factor XI deficiency", Blood Coagulation and Fibrinolysis, vol. 8, pp. 134-144 (1997).
Goodnight, S.H. et al., Chapter 4: "Screening Tests of Hemostasis", Disorders of Hemostasis and Thrombosis: A Clinical Guide, The McGraw-Hill Companies, publ., pp. 41-51 (2001).

(Continued)

Primary Examiner—Kamal Saeed
Assistant Examiner—Sun Jae Y Loewe
(74) Attorney, Agent, or Firm—Jing G. Sun

(57) ABSTRACT

The present invention provides compounds of Formula (I):

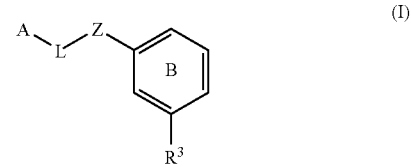

or a stereoisomer, tautomer, pharmaceutically acceptable salt or solvate form thereof, wherein the variables A, L, Z, $R^3$, and ring B are as defined herein. The compounds of Formula (I) are useful as selective inhibitors of serine protease enzymes of the coagulation cascade and/or contact activation system; for example thrombin, factor Xa, factor XIa, factor IXa, factor VIIa and/or plasma kallikrein. In particular, it relates to compounds that are selective factor XIa inhibitors. This invention also relates to pharmaceutical compositions comprising these compounds and methods of treating thromboembolic and/or inflammatory disorders using the same.

14 Claims, No Drawings

OTHER PUBLICATIONS

Meijers, J.C.M. et al., "High Levels of Coagulation Factor XI as a Risk Factor for Venous Thrombosis", The New England Journal of Medicine, vol. 342, No. 10, pp. 696-701 (2000).

Minnema, M.C. et al., "Activation of Clotting Factors XI and IX in Patients With Acute Myocardial Infarction", Arterioscler. Thromb. Vasc. Biol., vol. 20, pp. 2489-2493 (2000).

Schmaier, A.H., Chapter 5: "Contact Activation", Hemostasis and Thrombosis: Basic Principles and Clinical Practice, 4th Ed., Lippincott Williams & Wilkins, publ., Colman, R.W. et al., eds., pp. 105-127 (2001).

Walsh, P.N., "Platelets and Factor XI Bypass the Contact System of Blood Coagulation", Thrombosis and Haemostasis, vol. 82, No. 2, pp. 234-242 (1999).

Yong-Jin Wu et al., "Synthesis and Structure-Activity Relationship of Acrylamides as KCNQ2 Potassium Channel Openers", *J. Med. Chem.*, vol. 47, No. 11, pp. 2887-2896.

U.S. Appl. No. 11/610,027, Pinto et al.

* cited by examiner

SUBSTITUTED BIARYL COMPOUNDS AS FACTOR XIA INHIBITORS

CROSS-REFERENCE TO RELATED APPLICATIONS

The present application claims the priority benefit of U.S. Provisional Application No. 60/643,759, filed Jan. 13, 2005, which is expressly incorporated fully herein by reference.

FIELD OF THE INVENTION

The present invention relates generally to compounds that inhibit serine proteases. In particular it is directed to novel substituted biaryl compounds of Formula (I):

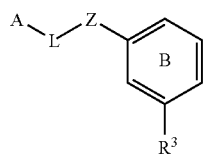

or a stereoisomer, tautomer, pharmaceutically acceptable salt, solvate, or prodrug form thereof, which are useful as selective inhibitors of serine protease enzymes of the coagulation cascade and/or contact activation system; for example thrombin, factor XIa, factor Xa, factor IXa and/or factor VIIa, and/or plasma kallikrein. In particular, it relates to compounds that are selective factor XIa inhibitors. This invention also relates to pharmaceutical compositions comprising these compounds and methods of using the same.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood coagulation is initiated in vivo by the binding of tissue factor (TF) to Factor VII (FVII) to generate Factor VIIa (FVIIa). The resulting TF:FVIIa complex activates Factor IX (FIX) and Factor X (FX) which leads to the production of Factor Xa (FXa). The FXa that is generated catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Walsh, P. N. *Thromb. Haemostasis.* 1999, 82, 234-242.) Factor XIa plays a key role in propagating this amplification loop and is thus an attractive target for anti-thrombotic therapy.

An alternative way of initiation of coagulation is operative when blood is exposed to artificial surfaces (e.g., during hemodialysis, 'on-pump' cardiovascular surgery, vessel grafts, bacterial sepsis). This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Activated FXI acts on FIX, which acts through the coagulation cascade to produce thrombin. Thus, inhibitors of plasma kallikrein would be expected to exert an antithrombotic effect under conditions of contact activation. Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway,* pages 103-122 in *Hemostasis and Thrombosis,* Lippincott Williams & Wilkins 2001; Schmaier A. H. *Contact Activation,* pages 105-128 in *Thrombosis and Hemorrhage,* 1998).

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D. *Trends Cardiovasc. Med.* 2000, 10, 198-204.)

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al. *Thromb. Res.* 2001, 101, 329-354.) Thus, inhibitors of factor XIa are expected to be anticoagulant and profibrinolytic.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of APTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The APTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D. *Frontiers in Bioscience* 2001, 6, 201-207; Gailani, D. et al. *Blood Coagulation and Fibrinolysis* 1997, 8, 134-144.) Taken together, these observations suggest that high levels of inhibition of factor XIa should be well tolerated. This is in contrast to gene targeting experiments with other coagulation factors.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al. *Arterioscler. Thromb. Vasc. Biol.* 2000, 20, 2489-2493). A second study establishes a positive correlation between the extent of coronary arteriosclerosis and factor XIa in complex with alpha 1 antitrypsin (Murakami, T. et al. *Arterioscler Thromb Vasc Biol* 1995, 15, 1107-1113.). In another study, Factor XI levels above the $90^{th}$ percentile in patients were associated with a 2.2-fold increased risk for venous thrombosis (Meijers, J. C. M. et al. *N. Engl. J. Med.* 2000, 342, 696-701.).

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Proteins or peptides that reportedly inhibit Factor XIa are disclosed in WO 01/27079. There are advantages in using small organic compounds, however, in preparing pharmaceuticals, e.g., small compounds generally have better oral bioavailability and compatibility in making formulations to aid in delivery of the drug as compared with large proteins or peptides. Small molecule inhibitors of Factor XIa are disclosed in U.S. Patent Application Publications US20040235847A1, US20040220206A1, and US20050228000A1, U.S. patent applications Ser. Nos. 11/151,627, and 11/151,667.

In addition, it is also desirable to find new compounds with improved pharmacological characteristics compared with known serine protease inhibitors. For example, it is preferred to find new compounds with improved factor XIa inhibitory activity and selectivity for factor XIa versus other serine proteases. Also, it is preferred to find new compounds with improved plasma kallikrein inhibitory activity and selectivity for plasma kallikrein versus other serine proteases. Also, it is preferred to find new compounds with improved activity in in vitro clotting assays, such as the prothrombin time (PT) assay or activated partial thromboplastin time assay (APTT) (for a description of the PT and APTT assays see, Goodnight, S. H.; Hathaway, W. E. Screening Tests of Hemostasis. *Disorders of Thrombosis and Hemostasis: a clinical guide*, $2^{nd}$ edition, McGraw-Hill: New York, 2001 pp. 41-51). It is also desirable and preferable to find compounds with advantageous and improved characteristics in one or more of the following categories, which are given as examples and are not intended to be limiting: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

SUMMARY OF THE INVENTION

The present invention provides novel substituted biaryl compounds, and analogues thereof, which are useful as selective inhibitors of serine protease enzymes, especially factor XIa and/or plasma kallikrein, or stereoisomers, tautomers, pharmaceutically acceptable salts, solvates, or prodrugs thereof.

The present invention also provides processes and intermediates for making the compounds of the present invention or a stereoisomer, tautomer, pharmaceutically acceptable salt, solvate, or prodrug form thereof The present invention also provides pharmaceutical compositions comprising a pharmaceutically acceptable carrier and a therapeutically effective amount of at least one of the compounds of the present invention or a stereoisomer, tautomer, pharmaceutically acceptable salt, solvate or prodrug form thereof.

The present invention also provides a method for modulation of the coagulation cascade and/or the contact activation system comprising administering to a host in need of such treatment a therapeutically effective amount of at least one of the compounds of the present invention or a stereoisomer, tautomer, pharmaceutically acceptable salt, solvate, or prodrug form thereof.

The present invention also provides a method for treating thromboembolic disorders comprising administering to a host in need of such treatment a therapeutically effective amount of at least one of the compounds of the present invention or a stereoisomer, tautomer, pharmaceutically acceptable salt, solvate, or prodrug form thereof.

The present invention also provides a method for treating inflammatory diseases disorders comprising administering to a host in need of such treatment a therapeutically effective amount of at least one of the compounds of the present invention or a stereoisomer, pharmaceutically acceptable salt, solvate, or prodrug form thereof.

The present invention also provides novel substituted biaryl compounds, and analogues thereof, for use in therapy.

The present invention also provides the use of substituted biaryl compounds, and analogues thereof, for the manufacture of a medicament for the treatment of a thromboembolic disorder.

The present invention also provides the use of substituted biaryl compounds, and analogues thereof, for the manufacture of a medicament for the treatment of an inflammatory disorder.

These and other features of the invention will be set forth in the expanded form as the disclosure continues.

DETAILED DESCRIPTION OF THE INVENTION

In a first aspect, the present invention provides, inter alia, compounds of Formula (I):

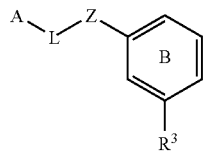

(I)

or stereoisomers, tautomers, pharmaceutically acceptable salts, solvates, or prodrugs thereof, wherein:

A is substituted with 0-1 $R^1$ and 0-3 $R^2$ and is selected from the group: $C_{3-7}$ cycloalkyl, $C_{3-7}$ cycloalkenyl, phenyl, naphthyl, and a 5- to 10-membered heterocycle comprising: carbon atoms and 1-4 heteroatoms selected from N, O, and $S(O)_p$; provided that A is other than $C_{3-7}$ cycloalkyl substituted with CN;

ring B is phenyl optionally further substituted with 0-3 $R^4$;

Z is —$CHR^{11}$— or $NR^{12}$;

L is —$(CH_2)_rC(O)NR^{10}$—, —$(CH_2)_rNR^{10}C(O)$—, —CH=CHC(O)$NR^{10}$—, —$S(O)_pCH_2C(O)NR^{10}$—, —$OCH_2C(O)NR^{10}$, —NHNHC(O)$NR^{10}$— or —$CH_2NR^{10}C(O)NR^{10}$—; provided that when L is —$(CH_2)_rNR^{10}C(O)$— or —NHNHC(O)$NR^{10}$—, then Z is other than $NR^{12}$;

$R^1$ is, independently at each occurrence, H, —$NH_2$, —NH($C_{1-3}$ alkyl), —$(CH_2)_rNR^7R^8$, —$(CH_2)_rNR^7C(O)OR^9$, —CH($C_{1-4}$ alkyl)$NH_2$, —CH($C_{1-4}$ alkyl)$_2NH_2$, —N($C_{1-3}$ alkyl)$_2$, —C(=NH)$NH_2$, —C(O)$NH_2$, —$CH_2NH_2$, —$CH_2NH(C_{1-3}$ alkyl), —$CH_2N(C_{1-3}$ alkyl)$_2$, —$CH_2CH_2NH_2$, —$CH_2CH_2NH(C_{1-3}$ alkyl), —$CH_2CH_2N(C_{1-3}$ alkyl)$_2$, —C(=$NR^{8a}$)$NR^8R^9$, —$NR^8CR^8$(=$NR^{8a}$), —C(O)$NR^7R^8$, —$S(O)_pNR^8R^9$, F, Cl, Br, I, $OCF_3$, $CF_3$, $OR^a$, $SR^a$, CN or $C_{1-6}$ alkyl substituted with 0-1 $R^{1a}$;

$R^{1a}$ is —C(=$NR^{8a}$)$NR^8R^9$, —NHC(=$NR^{8a}$)$NR^8R^9$, —$NR^8CH$(=$NR^{8a}$), —ONHC(=$NR^{8a}$)$NR^8R^9$, —$NR^7R^8$, —C(O)$NR^7R^8$, F, $OCF_3$, $CF_3$, $OR^a$, $SR^a$, CN, —$NR^8SO_2NR^8R^9$, —$NR^8SO_2R^c$, or —$(CF_2)_rCF_3$;

$R^2$ is, independently at each occurrence, H, =O, F, Cl, Br, $CF_3$, $OCF_3$, $CHF_2$, CN, $NO_2$, $OR^a$, $SR^a$, —C(O)$R^a$, —C(O)$OR^a$, —OC(O)$R^a$, —$NR^7R^8$, —C(O)$NR^7R^8$, —$NR^7C(O)R^b$, —$S(O)_pNR^8R^9$, —$NR^8S(O)_pR^c$, —$S(O)R^c$, —$S(O)_2R^c$, $C_{1-6}$ alkyl substituted with 0-2 $R^{2a}$, $C_{2-6}$ alkenyl substituted with 0-2 $R^{2a}$, $C_{2-6}$ alkynyl substituted with 0-2 $R^{2a}$, $C_{3-7}$ cycloalkyl substituted with 0-2 $R^{2a}$, —$(CH_2)_r$-phenyl substituted with 0-2 $R^{2b}$, or —$(CH_2)_r$-5- to 6-membered heterocycle comprising: carbon atoms and 1-4 heteroatoms selected from N, O, and $S(O)_p$, wherein said heterocycle is substituted with 0-3 $R^{2b}$;

$R^{2a}$ is, independently at each occurrence, H, F, Cl, Br, I, =O, =$NR^8$, CN, $OCF_3$, $CF_3$, $OR^a$, $SR^a$, —$NR^7R^8$, —C(O)$NR^8R^9$, —$NR^7C(O)R^b$, —$S(O)_pNR^8R^9$, —$NR^8SO_2R^c$, —$S(O)R^c$, or —$S(O)_2R^c$;

$R^{2b}$ is, independently at each occurrence, H, F, Cl, Br, I, =O, =$NR^8$, CN, $NO_2$, $OR^a$, $SR^a$, —C(O)$R^a$, —C(O)$OR^a$, —OC(O)$R^a$, —$NR^7R^8$, —C(O)$NR^7R^8$, —$NR^7C(O)R^b$, —$S(O)_pNR^8R^9$, —$SO_2R^c$, —$NR^8SO_2NR^8R^9$, —$NR^8SO_2R^c$, —$(CF_2)_rCF_3$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy-;

alternately, when $R^1$ and $R^2$ are substituted on adjacent ring atoms, they can be taken together with the ring atoms to which they are attached to form a 5- to 7-membered carbocycle or heterocycle comprising: carbon atoms and 0-4 heteroatoms selected from N, O, and $S(O)_p$, wherein said carbocycle or heterocycle is substituted with 0-2 $R^{2b}$;

$R^3$ is phenyl substituted with 0-3 $R^{3a}$ and 0-1 $R^{3d}$, naphthyl substituted with 0-3 $R^{3a}$ and 0-1 $R^{3d}$, or —$(CH_2)_r$-5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, F, Cl, Br, I, $OCF_3$, $CF_3$, —$(CH_2)_rCN$, $NO_2$, —$(CH_2)_rOR^{3b}$, —$(CH_2)_r$—$SR^{3b}$, —$(CH_2)_rNR^7R^8$, —C(=$NR^{8a}$)$NR^8R^9$, —NHC(=$NR^{8a}$)$NR^8R^9$, —C(O)$C_{1-4}$ alkyl, —$SO_2NHR^{3b}$, —$SO_2NHCOR^{3c}$, —$SO_2NHCO_2R^{3c}$, —$CONHSO_2R^{3c}$, —$NR^8CR^8$(=$NR^{8a}$), —NHC(O)$NR^8R^9$, —$(CH_2)_rNR^8C(O)R^{3b}$, —$(CH_2)_rNR^8CO_2R^{3b}$, —$(CH_2)_rS(O)_pNR^8R^9$, —$(CH_2)_rNR^8S(O)_pR^{3c}$, —$NHSO_2CF_3$, —$S(O)R^{3c}$, —$S(O)_2R^{3c}$, —$(CH_2)_rCO_2R^{3b}$, —$(CH_2)_rC(O)NR^8R^9$, —$(CH_2)_rOC(O)NR^8R^9$, —$NHCOCF_3$, —$NHSO_2R^{3c}$, —$CONHOR^{3b}$, $C_{1-4}$ haloalkyl, $C_{1-4}$ haloalkyloxy-, $C_{1-6}$ alkyl substituted by $R^{3e}$, $C_{2-6}$ alkenyl substituted by $R^{3e}$, $C_{1-6}$ alkynyl substituted by $R^{3e}$, $C_{3-6}$ cycloalkyl substituted by 0-1 $R^{3d}$, —$(CH_2)_r$—$C_{6-10}$ carbocycle substituted by 0-3 $R^{3d}$ or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$, or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 $R^{3e}$, $C_{2-6}$ alkenyl substituted with 0-2 $R^{3e}$, $C_{2-6}$ alkynyl substituted with 0-2 $R^{3e}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, F, Cl, Br, CN, $NO_2$, —$(CH_2)_rNR^7R^8$, —$(CH_2)_rOR^a$, —C(O)$R^a$, —C(O)$OR^a$, —OC(O)$R^a$, —$NR^7C(O)R^b$, —C(O)$NR^8R^9$, —$S(O)_2NR^8R^9$, —$NR^7R^8$, —$NR^8S(O)_2NR^8R^9$, —$NR^8S(O)_2R^c$, —$S(O)_pR^c$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^{3e}$ is, independently at each occurrence, H, —$(CH_2)_rOR^a$, F, =O, CN, $NO_2$, —$(CH_2)_rNR^7R^8$, —C(O)$R^a$, —C(O)$OR^a$, —OC(O)$R^a$, —$NR^7C(O)R^b$, —C(O)$NR^8R^9$, —$S(O)_2NR^8R^9$, —$NR^8S(O)_2NR^8R^9$, —$NR^8S(O)_2R^c$, —$S(O)_pR^c$, —$(CF_2)_rCF_3$, —$(CH_2)_r$—$C_{3-10}$ carbocycle substituted with 0-3 $R^d$, or —$(CH_2)_r$-5- to 10-membered heterocycl0065 comprising: carbon atoms and 1-4 heteroatoms selected from N, O, and $S(O)_p$, wherein said heterocycle is substituted with 0-3 $R^d$;

$R^4$ is, independently at each occurrence, H, F, Cl, Br, I, $OCF_3$, $CF_3$, CN, $NO_2$, $OR^a$, $SR^a$, —C(O)$R^a$, —C(O)$OR^a$, —OC(O)$R^a$, —$NR^7R^8$, —C(O)$NR^8R^9$, —$NR^8C(O)R^b$, —$NR^8C(O)OR^b$, —$NR^8C(O)NR^8$, —$S(O)_pNR^8R^9$, —$NR^8S(O)_pR^c$, —$S(O)R^c$, —$S(O)_2R^c$, $C_{1-6}$ alkyl substituted with 0-2

$R^{4a}$, $C_{2-6}$ alkenyl substituted with 0-2 $R^{4a}$, $C_{2-6}$ alkynyl substituted with 0-2 $R^{4a}$, —$(CH_2)_r$—$C_{3-10}$ carbocycle substituted with 0-3 $R^{4b}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{4b}$;

$R^{4a}$ is, independently at each occurrence, H, F, =O, $C_{1-4}$ alkyl, $OR^a$, $SR^a$, $CF_3$, CN, $NO_2$, —$C(O)R^a$, —$C(O)OR^a$, —$NR^7R^8$, —$C(O)NR^8R^9$, —$NR^7C(O)R^b$, —$S(O)_pNR^8R^9$, —$NR^8S(O)_pR^c$, —$S(O)R^c$, or —$S(O)_2R^c$;

$R^{4b}$ is, independently at each occurrence, H, =O, =$NR^8$, $OR^a$, $SR^a$, F, Cl, Br, I, CN, $NO_2$, —$NR^7R^8$, —$C(O)R^a$, —$C(O)OR^a$, —$NR^7C(O)R^b$, —$C(O)NR^8R^9$, —$SO_2NR^8R^9$, —$S(O)_2R^c$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy-;

$R^7$ is, independently at each occurrence, H, $C_{1-4}$ alkyl, —$C(O)(C_{1-4}$ alkyl), —$C(O)$—$CH_2$—$(C_{3-6}$ cycloalkyl), —$C(O)$-benzyl, —$C(O)CH_2(C_{6-10}$ aryl), —$C(O)O(C_{1-4}$ alkyl), —$C(O)OCH_2(C_{6-10}$ aryl), —$CONHR^c$, —$CON(C_{1-6}$ alkyl)$_2$, —$S(O)_2R^c$, —$(CH_2)_n$—$C_{3-7}$ cycloalkyl, —$(CH_2)_n$-phenyl, or —$(CH_2)_n$-5- to 10-membered heteroaryl comprising: carbon atoms and 1-4 heteroatoms selected from N, O, and $S(O)_p$;

$R^8$ is, independently at each occurrence, H, $C_{1-6}$ alkyl, —$(CH_2)_n$-phenyl, or —$(CH_2)_n$-5-10 membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-2 additional heteroatoms selected from N, O, and $S(O)_p$, wherein said heterocycle is substituted with 0-2 $R^d$;

$R^{8a}$ is, independently at each occurrence, $R^7$, OH, $C_{1-4}$ alkoxy, $(C_{6-10}$ aryl)-$C_{1-4}$ alkoxy; wherein said aryl is optionally substituted with 0-2 $R^f$;

$R^9$ is, independently at each occurrence, H, $C_{1-6}$ alkyl, or —$(CH_2)_n$-phenyl; wherein said alkyl and phenyl are optionally substituted with 0-2 $R^f$;

alternatively, $R^8$ and $R^9$, when attached to the same nitrogen, combine to form a 5- to 10-membered heterocycle comprising: carbon atoms and 0-2 additional heteroatoms selected from N, O, and $S(O)_p$, wherein said heterocycle is substituted with 0-2 $R^d$;

$R^{10}$ is, independently at each occurrence, H, $C_{1-6}$ alkyl substituted with 0-2 $R^{10a}$, —$(CH_2)_r$-phenyl substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{10a}$ is, independently at each occurrence, H, =O, $C_{1-4}$ alkyl, $OR^a$, $SR^a$, F, $CF_3$, CN, $NO_2$, —$C(O)R^a$, —$C(O)OR^a$, —$C(O)NR^7R^8$, —$NR^7C(O)R^b$, —$S(O)_pNR^8R^9$, —$NR^8S(O)_pR^c$, or —$S(O)_pR^c$;

$R^{11}$ is —$(CH_2)_rC(O)NR^8R^9$, $C_{1-4}$ haloalkyl, $C_{1-4}$ alkyl substituted with 0-3 $R^{11a}$, $C_{2-4}$ alkenyl substituted with 0-3 $R^{11a}$; $C_{2-4}$ alkynyl substituted with 0-3 $R^{11a}$, —$(CH_2)_s$—$C_{3-7}$ cycloalkyl substituted with 0-2 $R^{11b}$, —$(CH_2)_s$-phenyl substituted with 0-3 $R^{11b}$, —$(CH_2)_s$-naphthyl substituted with 0-3 $R^{11b}$, or —$(CH_2)_s$-5- to 10-membered heterocycle comprising: carbon atoms and 1-4 heteroatoms selected from N, O, and $S(O)_p$, wherein said heterocycle is substituted with 0-3 $R^{11b}$;

$R^{11a}$ is, independently at each occurrence H, =O, $OR^a$, $SR^a$, F, $CF_3$, CN, $NO_2$, —$NR^7R^8$, —$C(O)R^a$, —$C(O)OR^a$, —$C(O)NR^7R^8$, —$NR^7C(O)R^b$, —$S(O)_pNR^8R^9$, —$NR^8S(O)_pR^c$, —$S(O)_pR^c$, $C_{3-6}$ cycloalkyl, $C_{1-4}$ alkyl, $C_{1-4}$ haloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{11b}$ is, independently at each occurrence, H, =O, =$NR^8$, $OR^a$, $SR^a$, F, Cl, Br, CN, $NO_2$, $CF_3$, $OCF_3$, $OCHF_2$, —$NR^7R^8$, —$C(O)R^a$, —$C(O)OR^a$, —$C(O)NR^7R^8$, —$CH_2OR^a$, —$CH_2NR^7R^8$, —$NR^8C(O)R^b$, —$S(O)_pNR^8R^9$, —$NR^8S(O)_pR^c$, —$S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$;

$R^{12}$ is $C_{1-6}$ alkyl, —$(CH_2)_s$-cycloalkyl, —$(CH_2)_s$-phenyl, —$(CH_2)_s$-naphthyl, —$(CH_2)_r$$NR^8C(O)R^a$, —$C(O)R^c$, —$C(O)OR^c$, —$CONR^8R^c$, —$S(O)_2R^c$, —$C(O)O$—$(C_{1-4}$ alkyl)-OC(O)—$(C_{1-4}$ alkyl), —$C(O)O$—$(C_{1-4}$ alkyl)-OC(O)—$(C_{6-10}$ aryl), or —$(CH_2)_s$-5-to 10-membered heteroaryl comprising: carbon atoms and 1-4 heteroatoms selected from N, O, and $S(O)_p$; wherein said alkyl, phenyl, aryl, and heteroaryl are optionally substituted with 0-3 $R^f$;

$R^a$ is, independently at each occurrence, H, $CF_3$, $C_{1-6}$ alkyl, —$(CH_2)_r$—$C_{3-7}$ cycloalkyl, —$(CH_2)_r$—$C_{6-10}$ aryl, or —$(CH_2)_r$-5- to 10-membered heteroaryl comprising carbon atoms and 1-4 heteroatoms selected from N, O, and $S(O)_p$; wherein said cycloalkyl, aryl or heteroaryl groups are optionally substituted with 0-2 $R^f$;

$R^b$ is, independently at each occurrence, $CF_3$, OH, $C_{1-4}$ alkoxy, $C_{1-6}$ alkyl, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$ and substituted with 0-3 $R^d$;

$R^c$ is, independently at each occurrence, $CF_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, $(C_{6-10}$ aryl)-$C_{1-4}$ alkyl, or (5-to 10-membered heteroaryl)-$C_{1-4}$ alkyl, wherein said aryl is substituted with 0-3 $R^f$ and said heteroaryl comprises: carbon atoms and 1-4 heteroatoms selected from N, O, and $S(O)_p$ and substituted with 0-3 $R^f$;

$R^d$ is, independently at each occurrence, H, =O, $OR^a$, F, Cl, Br, I, CN, $NO_2$, —$NR^7R^8$, —$C(O)R^a$, —$C(O)OR^a$, —$OC(O)R^a$, —$NR^8C(O)R^a$, —$C(O)NR^7R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, —$NR^8R^9$, —$C(O)R^a$, —$C(O)OR^a$, —$NR^8C(O)R^a$, —$C(O)NR^7R^8$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

$R^f$ is, independently at each occurrence, H, =O, —$(CH_2)_rOR^g$, F, Cl, Br, I, CN, $NO_2$, —$NR^gR^g$, —$C(O)R^g$, —$C(O)OR^g$, —$NR^gC(O)R^g$, —$C(O)NR^gR^g$, —$SO_2NR^gR^g$, —$NR^gSO_2NR^gR^g$, —$NR^gSO_2$—$C_{1-4}$ alkyl, —$NR^gSO_2CF_3$, —$NR^gSO_2$-phenyl, —$S(O)_2CF_3$, —$S(O)_p$—$C_{1-4}$ alkyl, —$S(O)_p$-phenyl, —$(CH_2)_n$-phenyl, —$(CF_2)_rCF_3$, $C_{1-6}$ alkyl, $C_{2-6}$ alkenyl, or $C_{2-6}$ alkynyl;

alternately, when two $R^f$ groups are substituents on adjacent atoms they may be taken together with the atoms to which they are attached to form a 5-7-membered heterocycle comprising carbon atoms and 1-4 heteroatoms selected from N, O, and $S(O)_p$ and substituted with 0-2 $R^g$;

$R^g$ is, independently at each occurrence, H, $C_{1-6}$ alkyl, or —$(CH_2)_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4; and s, at each occurrence, is selected from 1, 2, 3, and 4;

provided that when $R^{11}$ is —$CH_2CO_2H$, then A is other than an optionally substituted 5- to 10-membered fully or partially saturated, containing at least one N.

In a second aspect, the present invention includes compounds of Formula (I) or stereoisomers, pharmaceutically acceptable salts, solvates, or prodrugs thereof, wherein:

A is substituted with 0-1 $R^1$ and 0-3 $R^2$ and is selected from the group: $C_{3-7}$ cycloalkyl, phenyl, naphthyl, pyridyl, indazolyl, benzimidazolyl, benzisoxazolyl, quinolinyl, isoquinolinyl, 1H-4-oxo-quinazolinyl, 2H-1-oxo-isoquinolinyl, 3H-4-oxo-quinazolinyl, 3,4-dihydro-2H-1-oxo-isoquinolinyl, 2,3-dihydro-isoindolinone, 1,2,3,4-tetrahydroquinolinyl, 5,6,7,8-tetrahydroquinolinyl, 1,2,3,4-tetrahydroisoquinolinyl, 5,6,7,8-tetrahydroisoquinolinyl, quinazolinyl, and phthalazinyl;

Z is $CHR^{11}$;

L is —$C(O)NR^{10}$—, —$NR^{10}C(O)$— or —$CH_2NHC(O)NH$—;

$R^3$ is phenyl substituted with 0-3 $R^{3a}$, naphthyl substituted with 0-3 $R^{3a}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3a}$;

$R^{3a}$ is, independently at each occurrence, F, Cl, Br, Me, CN, OH, OMe, —$CH_2OH$, —$CH_2OMe$, $CF_3$, COMe, $CO_2H$, $CO_2Me$, —$CH_2CO_2H$, —$(CH_2)_2CO_2H$, —$CH_2CO_2Me$, —$CH_2CO_2Et$, —$CH_2CN$, —$NHC(O)Me$, —$NHC(O)R^{3b}$, —$NHSO_2R^{3c}$, —$NHCO_2R^{3c}$, —$CH_2NHCO_2R^{3c}$, —$NHC(O)NR^8R^9$, —$NR^7R^8$, —$CH_2NR^7R^8$, —$S(O)_pNR^8R^9$, —$C(O)NR^8R^9$, —$CH_2C(O)NR^8R^9$, —$C(O)NHOR^{3b}$, —$C(=NH)NH_2$, or —$(CH_2)_r$-5- to 6-membered heterocycle comprising: carbon atoms and 1-4 heteroatoms selected from N, O, and $S(O)_p$, wherein said heterocycle is substituted with 0-1 $R^{3d}$; and $R^4$ is, independently at each occurrence, H, F, Cl, Br, I, $CF_3$, $OCF_3$, CN, $NO_2$, $OR^a$, $SR^a$, —$C(O)R^a$, —$C(O)OR^a$, —$NR^7R^8$, —$C(O)NR^8R^9$, —$NR^8C(O)R^b$, —$NR^8C(O)OR^b$, —$NR^8C(O)NR^8$, —$S(O)_pNR^8R^9$, —$NR^8S(O)_pR^c$, —$S(O)R^c$, —$S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, —$(CH_2)_r$-phenyl substituted with 0-3 $R^{4b}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{4b}$.

In a third aspect, the present invention includes compounds of Formula (I) or stereoisomers, pharmaceutically acceptable salts, solvates, or prodrugs thereof, wherein:

$R^1$ is, independently at each occurrence, F, Cl, Br, Me, Et, $CF_3$, OMe, OH, —$NH_2$, —$C(=NH)NH_2$, —$C(O)NH_2$, or —$CH_2NH_2$;

$R^3$ is phenyl substituted with 0-2 $R^{3a}$, naphthyl substituted with 0-2 $R^{3a}$, or a 5- to 10-membered heterocycle substituted with 0-2 $R^{3a}$, wherein said heterocycle is selected from: thiophene, furan, thiazole, tetrazole, pyridine, pyridinone, pyrimidine, pyrrole, pyrazole, indole, 2-oxoindole, isoindolin-1-one, indazole, benzofuran, benzothiophene, benzoimidazole, benzisoxazole, quinazoline, phthalazine, quinoline, isoquinoline, 3H-quinazolin-4-one, 2H-phthalazin-1-one, 2H-3,4-dihydrophthalazin-1-one, 1H-quinolin-4-one, 2H-3,4-dihydroisoquinolin-1-one, 3,4-dihydro-1H-quinolin-2-one, 1H-quinolin-2-one, 1,3-dihydroindol-2-one, 3H-benzoxazol-2-one, 1,3-dihydrobenzimidazol-2-one, 1,4-dihydro-3,1-benzoxazin-2-one, 3,4-dihydro-1H-quinazolin-2-one, 4H-benzothiazin-3-one, 4H-1,4-benzoxazin-3-one, 1,3,4,5-tetrahydro-1-benzazepin-2-one, 1,3,4,5-tetrahydro-1,3-benzodiazepin-2-one, 8,9-dihydro-5H-7-oxa-5-aza-benzocyclohepten-6-one, 1,3-dihydroindol-2-one, benzimidazol-2-one, 1,3-dihydro-benzimidazol-2-one, 3H-benzoxazol-2-one, and 1,2,3,4-tetrahydroquinoline;

$R^{3a}$ is, independently at each occurrence, F, Cl, Br, Me, CN, OH, OMe, —$CH_2OH$, —$CH_2OMe$, $CF_3$, COMe, $CO_2H$, $CO_2Me$, —$CH_2CO_2H$, —$(CH_2)_2CO_2H$, —$CH_2CO_2Me$, —$CH_2CO_2Et$, —$CH_2CN$, $NH_2$, —$CH_2NH_2$, —$CH_2NMe_2$, —$NHC(O)Me$, —$NHCO_2Me$, —$NHCO_2Et$, —$NHCO_2Bn$, —$NHCO_2iBu$, —$CH_2NHCO_2Me$, —$NHC(O)NH_2$, —$NHC(O)NHMe$, —$NHC(O)N(Me)_2$, —$NHSO_2Me$, —$SO_2NH_2$, —$SO_2NHMe$, —$CONH_2$, —$CONHMe$, —$CON(Me)_2$, —$CH_2CONH_2$, —$C(=NH)NH_2$, —$NH(1H$-imidazol-2-yl), 1H-tetrazol-5-yl, or N-morpholinyl;

$R^4$ is, independently at each occurrence, H, F, Cl, Br, OH, OMe, $NH_2$, Me, Et, $CF_3$, —$CH_2OH$, —$(CH_2)_2OH$, —$(CH_2)_3OH$, —$CH_2NH_2$, —$(CH_2)_2NH_2$, —$(CH_2)_3NH_2$, —$C(O)_2H$, —$C(O)NH_2$, —$C(O)NHMe$, —$C(O)N(Me)_2$, —$CH_2CO_2H$, —$CH_2C(O)NH_2$, —$NHC(O)Me$, —$NHCO_2Me$, —$NHC(O)NHMe$, —$NHC(O)N(Me)_2$, —$NHSO_2Me$, —$SO_2NH_2$, —$SO_2NHMe$, —$SO_2N(Me)_2$, Ph, or 4-$NHCO_2Me$-Ph; and $R^{11}$ is —$(CH_2)_rC(O)NR^7R^8$, $C_{1-4}$ alkyl substituted with 0-2 $R^{11a}$, —$(CH_2)_s$-cyclohexyl substituted with 0-1 $R^{11b}$, —$(CH_2)_s$-phenyl substituted with 0-2 $R^{11b}$, —$(CH_2)_s$-naphthyl substituted with 0-2 $R^{11b}$, or —$(CH_2)_s$-heteroaryl substituted with 0-2 $R^{11b}$; wherein said heteroaryl is selected from: thienyl, furanyl, imidazolyl, thiazolyl, pyrrolyl, pyrazolyl, pyridyl, pyrimidyl, indolyl, indazolyl, benzofuranyl, benzothienyl, benzthiazolyl, benzimidazolyl, benzisoxazolyl, benzoxazolyl, quinazolinyl, phthalazinyl, 1,3-benzodioxolyl, oxazolyl, isoxazolyl, triazolyl, quinolinyl, and isoquinolinyl.

In a fourth aspect, the present invention includes compounds of Formula (I) or stereoisomers, pharmaceutically acceptable salts, solvates, or prodrugs thereof, wherein:

$R^{11}$ is —$(CH_2)_rC(O)NR^7R^8$, $C_{1-4}$ alkyl substituted with 0-2 $R^{11a}$, —$CH_2$-cyclohexyl substituted with 0-1 $R^{11b}$, —$CH_2$-phenyl substituted with 0-2 $R^{11b}$, —$CH_2$-naphthyl substituted with 0-2 $R^{11b}$, or —$(CH_2)_s$-heteroaryl substituted with 0-2 $R^{11b}$; wherein said heteroaryl is selected from: imidazol-4-yl, thiazol-4-yl, triazol-3-yl, oxazol-2yl, pyrid-2-yl, pyrid-3-yl, pyrid-4-yl, benzthiazol-2-yl, indol-3-yl, indol-5-yl, indol-6-yl, indazol-6-yl, indazol-5-yl, benzimidazol-6-yl, and benzimidazol-2-yl; and $R^{11b}$ is, independently at each occurrence, H, F, Cl, Br, OMe, $C_{1-4}$ alkyl, $OCF_3$, $OCHF_2$, OPh, OBn, $NO_2$, —$NH_2$, —$CO_2H$, —$CO_2Me$, —$CONH_2$, —$C(O)Ph$, —$C(O)NMePh$, —$C(O)NHPh$, —$NHC(O)Me$, —$NHC(O)CH_2Ph$, —$NMeC(O)Ph$, —$NHC(O)CH_2CH_2Ph$, —$NHS(O)_2Ph$, —$NMeS(O)_2Ph$, —$S(O)_2NMePh$, $CF_3$, Ph, Bn, —$C(O)$-5- to 10-membered heterocycle substituted with 0-2 $R^d$,

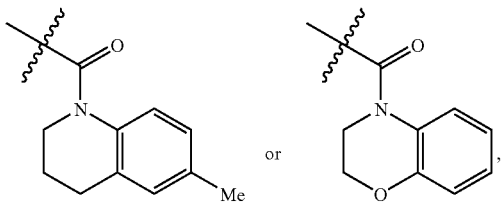

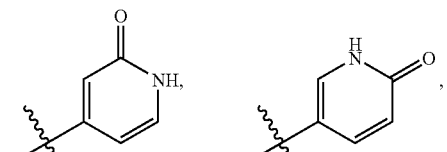

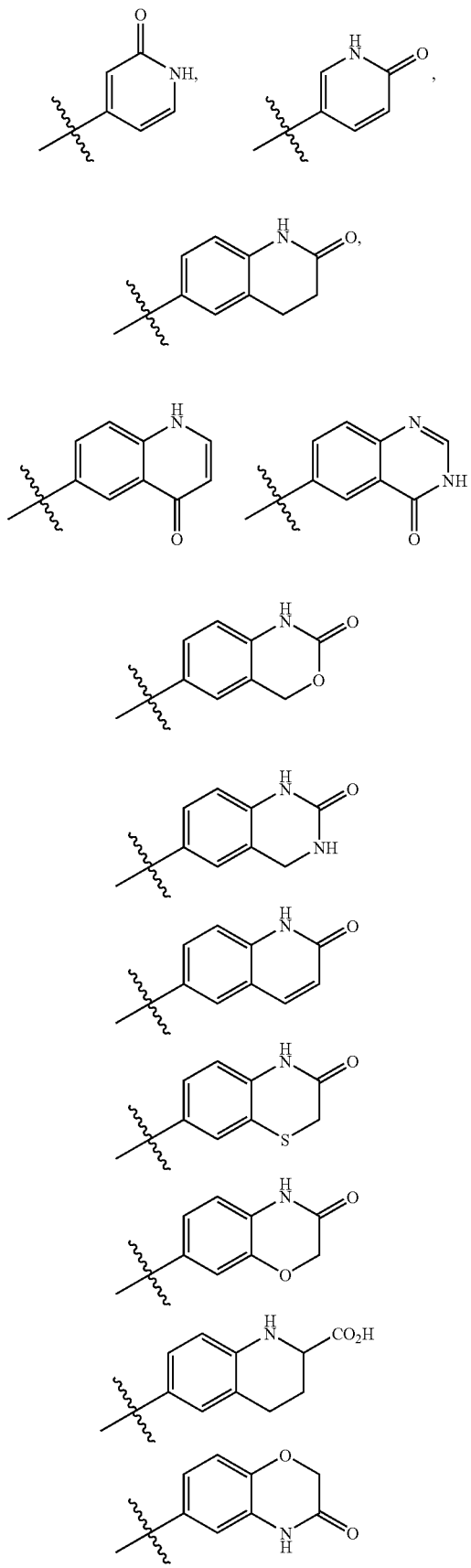

wherein each phenyl is optionally substituted by 0-2 R$^d$;

alternately, when two R$^{11b}$ groups are substituents on adjacent atoms they may be taken together with the atoms to which they are attached to form a 5 to 7-membered heterocycle comprising carbon atoms and 1-4 heteroatoms selected from N, O, and S(O)$_p$ and substituted with 0-2 R$^g$.

In a fifth aspect, the present invention includes compounds of Formula (I) or stereoisomers, pharmaceutically acceptable salts, solvates, or prodrugs thereof, wherein:

A is 4-aminomethyl-cyclohexyl, 4-amidino-phenyl, 4-methyl-cyclohexyl, 4-aminomethyl-phenyl, 4-aminomethyl-naphth-1-yl, 4 aminomethyl-2-fluoro-phenyl, 2-fluoro-4-methyl-phenyl, 4-amino-2-fluoro-phenyl, 2,6-difluoro-4-methoxy-phenyl, 2,6-difluoro-4-methyl-phenyl, 4-amino-2,6-difluoro-phenyl, 4-carbamoyl-2-fluoro-phenyl, 3-chlorophenyl, 3-chloro-2,6-difluoro-phenyl, 2-amino-pyridin-5-yl, 1-aminoisoquinolin-6-yl, 1-amino-5,6,7,8-tetrahydroisoquinolin-6-yl, 3-amino-benzisoxazol-6-yl, 3-amino-indazol-6-yl, quinolin-2-yl, 1-amino-isoquinolin-6-yl, or 1,2,3,4-tetrahydroisoquinolin-6-yl; and R$^3$ is Ph, 3-F-Ph, 4-F-Ph, 4-Br-Ph, 3-CF$_3$-Ph, 3-NH$_2$-Ph, 4-NH$_2$-Ph, 2-CH$_2$NH$_2$-Ph, 3-CH$_2$NH$_2$-Ph, 4-CH$_2$NH$_2$-Ph, 2-CH$_2$NMe$_2$-Ph, 3-CH$_2$NMe$_2$-Ph, 4-CH$_2$NMe$_2$-Ph, 3-OH-Ph, 4-OH-Ph, 3-OMe-Ph, 4-OMe-Ph, 3-CH$_2$OH-Ph, 4-CH$_2$OH-Ph, 3-CH$_2$OMe-Ph, 4-CH$_2$OMe-Ph, 4-COMe-Ph, 3-CO$_2$H-Ph, 4-CO$_2$H-Ph, 3-CH$_2$CO$_2$H-Ph, 4-CH$_2$CO$_2$H-Ph, 2-(CH$_2$)$_2$CO$_2$H-Ph, 3-(CH$_2$)$_2$CO$_2$H-Ph, 4-(CH$_2$)$_2$CO$_2$H-Ph, 3-CH$_2$CO$_2$Et-Ph, 4-CH$_2$CO$_2$Et-Ph, 3-CN-Ph, 4-CN-Ph, 3-CH$_2$CN-Ph, 4-CH$_2$CN-Ph, 3-CONH$_2$-Ph, 4-CONH$_2$-Ph, 3-CH$_2$CONH$_2$-Ph, 4-CH$_2$CONH$_2$-Ph, 3-CONHMe-Ph, 4-CONHMe-Ph, 3-NHCOMe-Ph, 4-NHCOMe-Ph, 2-NHCO$_2$Me-Ph, 3-NHCO$_2$Me-Ph, 4-NHCO$_2$Me-Ph, 4-NHCO$_2$Et-Ph, 4-NHCO$_2$Bn-Ph, 4-CH$_2$NHCO$_2$Me-Ph, 2-NHSO$_2$Me-Ph, 3-NHSO$_2$Me-Ph, 4-NHSO$_2$Me-Ph, 3-(1H-tetrazol-5-yl)-Ph, 4-(N-morpholinyl)-Ph, 4-[(1H-imidazol-2-yl)amino)]-Ph, 2,4-diF-Ph, 3,4-diCl-Ph, 3-CN-4-F-Ph, 4-CN-3-F-Ph, 3-CO$_2$H-4-NH$_2$-Ph, 3-CO$_2$H-5-NH$_2$-Ph, 3-CO$_2$Me-4-NH$_2$-Ph, 3-CO$_2$H-4-NHCOMe-Ph, 3-CO$_2$H-4-NHCO$_2$Me-Ph, 2-naphthyl, 2-CO$_2$H-thien-5-yl, 2-CO$_2$Me-thien-5-yl, 2-CONH$_2$-thien-5-yl, 2-(1H-tetrazol-5-yl)-thien-5-yl, pyrrol-3-yl, 2-NH$_2$-thiazol-4-yl, pyrid-2-yl, pyrid-3-yl, pyrid-4-yl, 2-NH$_2$-pyrid-3-yl, 2-NH$_2$-pyrid-5-yl, 2-NH$_2$-pyrid-6-yl, 2-CONH$_2$-pyrid-5-yl, 2-NHCO$_2$Me-pyrid-5-yl, 3-NH$_2$-benzisoxazol-5-yl, 3-NH$_2$-benzisoxazol-6-yl, 3-NH$_2$-indazol-5-yl, 3-NH$_2$-indazol-6-yl, 3-OH-indazol-5-yl, 3-OH-indazol-6-yl, quinolin-5-yl, 1-NH$_2$-phthalazin-6-yl, 4-NH$_2$-quinazolin-7-yl, 2-Me-4-NH$_2$-quinazolin-7-yl, 2,4-di-NH$_2$-quinazolin-7-yl, -continued

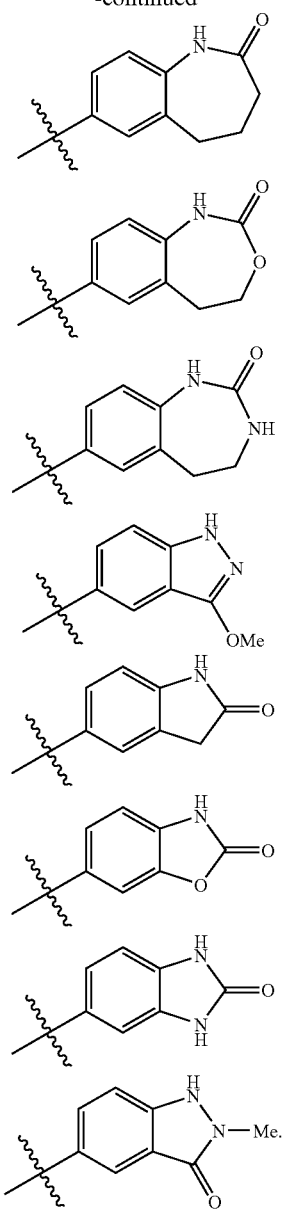

In a sixth aspect, the present invention includes compounds of Formula (I) or stereoisomers, pharmaceutically acceptable salts, solvates, or prodrugs thereof, wherein:

A is 4-aminomethyl-cyclohexyl, 2-amino-pyridin-5-yl, or quinolin-2-yl;

$R^3$ is Ph, 3-$CF_3$-Ph, 3-$NH_2$-Ph, 4-$CH_2NH_2$-Ph, 2-$CH_2NMe_2$-Ph, 3-OH-Ph, 3-OMe-Ph, 4-OMe-Ph, 4-$CH_2OH$-Ph, 4-$CH_2OMe$-Ph, 4-COMe-Ph, 3-$CO_2H$-Ph, 4-$CO_2H$-Ph, 4-$CH_2CO_2H$-Ph, 2-$(CH_2)_2CO_2H$-Ph, 3-$(CH_2)_2CO_2H$-Ph, 4-$(CH_2)_2CO_2H$-Ph, 3-CN-Ph, 4-$CH_2CN$-Ph, 3-$CONH_2$-Ph, 4-$CONH_2$-Ph, 3-$CH_2CONH_2$-Ph, 4-$CH_2CONH_2$-Ph, 3-NHCOMe-Ph, 4-NHCOMe-Ph, 2-$NHCO_2Me$-Ph, 3-$NHCO_2Me$-Ph, 4-$NHCO_2Me$-Ph, 4-$CH_2NHCO_2Me$-Ph, 2-$NHSO_2Me$-Ph, 3-$NHSO_2Me$-Ph, 4-$NHSO_2Me$-Ph, 3-(1H-tetrazol-5-yl)-Ph, 4-(N-morpholinyl)-Ph, 4-[(1H-imidazol-2-yl)amino)]-Ph, 3,4-diCl-Ph, 3-$CO_2H$-4-$NH_2$-Ph, 3-$CO_2H$-5-$NH_2$-Ph, 3-$CO_2Me$-4-$NH_2$-Ph, 3-$CO_2H$-4-NHCOMe-Ph, 3-$CO_2H$-4-$NHCO_2Me$-Ph, 2-$NH_2$-pyrid-5-yl, 2-$NHCO_2Me$-pyrid-5-yl, 2-$CO_2H$-thien-5-yl, 2-$CO_2Me$-thien-5-yl, 2-$CONH_2$-thien-5-yl, 2-(1H-tetrazol-5-yl)-thien-5-yl, 2-$NH_2$-thiazol-4-yl, pyrrol-3-yl, pyrid-4-yl, 3-$NH_2$-indazol-6-yl, 3-$NH_2$-benzisoxazol-6-yl, 2-naphthyl, quinolin-5-yl, 3-OH-indazol-5-yl, or

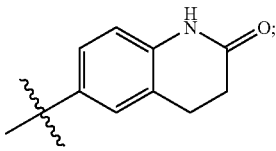

$R^4$ is, independently at each occurrence, H, F, Cl, Br, OH, OMe, $NH_2$, Me, Et, or 4-$NHCO_2Me$-Ph; and $R^{11}$ is benzyl, —C(O)$NHCH_2$-pyrid-2-yl, or 3-[C(O)NMePh]-benzyl.

In a seventh aspect, the present invention provides the (S)-enantiomer of the compound of Formula (I) or pharmaceutically acceptable salt, solvate, or prodrug thereof.

In an eighth aspect, the present invention provides a compound selected from the exemplified examples or a stereoisomer, pharmaceutically acceptable salt, solvate, or prodrug thereof.

In another aspect, the present invention provides includes compounds of Formula (I) or stereoisomers, pharmaceutically acceptable salts, solvates, or prodrugs thereof, wherein:

A is substituted with 0-1 $R^1$ and 0-3 $R^2$ and is selected from the group: $C_{3-7}$ cycloalkyl, phenyl, naphthyl, 1,2,3,4-tetrahydronaphthyl, pyridyl, indazolyl, benzimidazolyl, benzisoxazolyl, quinolinyl, isoquinolinyl, 1H-4-oxo-quinazolinyl, 2H-1-oxo-isoquinolinyl, 3H-4-oxo-quinazolinyl, 3,4-dihydro-2H-1-oxo-isoquinolinyl, 2,3-dihydro-isoindolinone, 1,2,3,4-tetrahydroquinolinyl, 5,6,7,8-tetrahydroquinolinyl, 1,2,3,4-tetrahydroisoquinolinyl, 5,6,7,8-tetrahydroisoquinolinyl, quinazolinyl, and phthalazinyl;

$R^3$ is phenyl substituted with 0-3 $R^{3a}$, naphthyl substituted with 0-3 $R^{3a}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3a}$; and $R^{11}$ is —$(CH_2)_s$-cyclohexyl substituted with 0-1 $R^{11b}$, —$(CH_2)_s$-phenyl substituted with 0-2 $R^{11b}$, —$(CH_2)_s$-naphthyl substituted with 0-2 $R^{11b}$, or —$(CH_2)_s$-heteroaryl substituted with 0-2 $R^{11b}$; wherein said heteroaryl is selected from: thienyl, furanyl, imidazolyl, thiazolyl, pyrrolyl, pyrazolyl, pyridyl, pyrimidyl, indolyl, indazolyl, benzofuranyl, benzothienyl, benzthiazolyl, benzimidazolyl, benzisoxazolyl, benzoxazolyl, quinazolinyl, phthalazinyl, 1,3-benzodioxolyl, oxazolyl, isoxazolyl, triazolyl, quinolinyl, and isoquinolinyl.

In another aspect, the present invention provides includes compounds of Formula (I) or stereoisomers, pharmaceutically acceptable salts, solvates, or prodrugs thereof, wherein:

A is substituted with 0-1 $R^1$ and 0-3 $R^2$ and is selected from the group: $C_{3-7}$ cycloalkyl, phenyl, naphthyl, 1,2,3,4-tetrahydronaphthyl, pyridyl, indazolyl, benzimidazolyl, benzisoxazolyl, quinolinyl, isoquinolinyl, 1H-4-oxo-quinazolinyl, 2H-1-oxo-isoquinolinyl, 3H-4-oxo-quinazolinyl, 3,4-dihydro-2H-1-oxo-isoquinolinyl, 2,3-dihydro-isoindolinone, 1,2,3,4-tetrahydroquinolinyl, 5,6,7,8-tetrahydroquinolinyl, 1,2,3,4-tetrahydroisoquinolinyl, 5,6,7,8-tetrahydroisoquinolinyl, quinazolinyl, and phthalazinyl.

In another aspect, the present invention provides includes compounds of Formula (I) or stereoisomers, pharmaceutically acceptable salts, solvates, or prodrugs thereof, wherein:

A is 4-aminomethyl-cyclohexyl, 4-amidino-phenyl, 4-methyl-cyclohexyl, 4-aminomethyl-phenyl, 4-aminomethyl-naphth-1-yl, 4 aminomethyl-2-fluoro-phenyl, 2-fluoro-4-methyl-phenyl, 4-amino-2-fluoro-phenyl, 2,6-difluoro-4-methoxy-phenyl, 2,6-difluoro-4-methyl-phenyl, 4-amino-2,6-difluoro-phenyl, 4-carbamoyl-2-fluoro-phenyl, 3-chloro-phenyl, 3-chloro-2,6-difluoro-phenyl, 2-amino-pyridin-5-yl, 1-aminoisoquinolin-6-yl, 1-amino-5,6,7,8-tetrahydroisoquinolin-6-yl, 3-amino-benzisoxazol-6-yl, 3-amino-indazol-6-yl, quinolin-2-yl, 1-amino-isoquinolin-6-yl, or 1,2,3,4-tetrahydroisoquinolin-6-yl.

In another aspect, the present invention provides includes compounds of Formula (I) or stereoisomers, pharmaceutically acceptable salts, solvates, or prodrugs thereof, wherein: A is 4-aminomethyl-cyclohexyl, 2-amino-pyridin-5-yl, or quinolin-2-yl.

In another aspect, the present invention provides includes compounds of Formula (I) or stereoisomers, pharmaceutically acceptable salts, solvates, or prodrugs thereof, wherein: A is 4-aminomethyl-cyclohexyl.

In another aspect, the present invention provides includes compounds of Formula (I) or stereoisomers, pharmaceutically acceptable salts, solvates, or prodrugs thereof, wherein: L is —C(O)NR$^{10}$—, —NR$^{10}$C(O)—.

In another aspect, the present invention provides includes compounds of Formula (I) or stereoisomers, pharmaceutically acceptable salts, solvates, or prodrugs thereof, wherein: L is —C(O)NR$^{10}$—.

In another aspect, the present invention provides includes compounds of Formula (I) or stereoisomers, pharmaceutically acceptable salts, solvates, or prodrugs thereof, wherein: wherein: R$^{10}$ is H.

In another aspect, the present invention provides includes compounds of Formula (I) or stereoisomers, pharmaceutically acceptable salts, solvates, or prodrugs thereof, wherein: R$^3$ is phenyl substituted with 0-3 R$^{3a}$ and 0-1 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3a}$ and 0-1 R$^{3d}$.

In another aspect, the present invention provides includes compounds of Formula (I) or stereoisomers, pharmaceutically acceptable salts, solvates, or prodrugs thereof, wherein: R$^3$ is phenyl substituted with 0-2 R$^{3a}$, naphthyl substituted with 0-2 R$^{3a}$, or a 5- to 10-membered heterocycle substituted with 0-2 R$^{3a}$, wherein said heterocycle is selected from: thiophene, furan, thiazole, tetrazole, pyridine, pyridinone, pyrimidine, pyrrole, pyrazole, indole, 2-oxoindole, isoindolin-1-one, indazole, benzofuran, benzothiophene, benzoimidazole, benzisoxazole, quinazoline, phthalazine, quinoline, isoquinoline, 3H-quinazolin-4-one, 2H-phthalazin-1-one, 2H-3,4-dihydrophthalazin-1-one, 1H-quinolin-4-one, 2H-3,4-dihydroisoquinolin-1-one, 3,4-dihydro-1H-quinolin-2-one, 1H-quinolin-2-one, 1,3-dihydroindol-2-one, 3H-benzoxazol-2-one, 1,3-dihydrobenzinidazol-2-one, 1,4-dihydro-3,1-benzoxazin-2-one, 3,4-dihydro-1H-quinazolin-2-one, 4H-benzothiazin-3-one, 4H-1,4-benzoxazin-3-one, 1,3,4,5-tetrahydro-1-benzazepin-2-one, 1,3,4,5-tetrahydro-1,3-benzodiazepin-2-one, 8,9-dihydro-5H-7-oxa-5-aza-benzocyclohepten-6-one, 1,3-dihydro-indol-2-one, benzimidazol-2-one, 1,3-dihydro-benzimidazol-2-one, 3H-benzoxazol-2-one, and 1,2,3,4-tetrahydroquinoline.

In another aspect, the present invention provides includes compounds of Formula (I) or stereoisomers, pharmaceutically acceptable salts, solvates, or prodrugs thereof, wherein: R$^3$ is Ph, 3-F-Ph, 4-F-Ph, 4-Br-Ph, 3-CF$_3$-Ph, 3-NH$_2$-Ph, 4-NH$_2$-Ph, 2-CH$_2$NH$_2$-Ph, 3-CH$_2$NH$_2$-Ph, 4-CH$_2$NH$_2$-Ph, 2-CH$_2$NMe$_2$-Ph, 3-CH$_2$NMe$_2$-Ph, 4-CH$_2$NMe$_2$-Ph, 3-OH-Ph, 4-OH-Ph, 3-OMe-Ph, 4-OMe-Ph, 3-CH$_2$OH-Ph, 4-CH$_2$OH-Ph, 3-CH$_2$OMe-Ph, 4-CH$_2$OMe-Ph, 4-COMe-Ph, 3-CO$_2$H-Ph, 4-CO$_2$H-Ph, 3-CH$_2$CO$_2$H-Ph, 4-CH$_2$CO$_2$H-Ph, 2-(CH$_2$)$_2$CO$_2$H-Ph, 3-(CH$_2$)$_2$CO$_2$H-Ph, 4-(CH$_2$)$_2$CO$_2$H-Ph, 3-CH$_2$CO$_2$Et-Ph, 4-CH$_2$CO$_2$Et-Ph, 3-CN-Ph, 4-CN-Ph, 3-CH$_2$CN-Ph, 4-CH$_2$CN-Ph, 3-CONH$_2$-Ph, 4-CONH$_2$-Ph, 3-CH$_2$CONH$_2$-Ph, 4-CH$_2$CONH$_2$-Ph, 3-CONHMe-Ph, 4-CONHMe-Ph, 3-NHCOMe-Ph, 4-NHCOMe-Ph, 2-NHCO$_2$Me-Ph, 3-NHCO$_2$Me-Ph, 4-NHCO$_2$Me-Ph, 4-NHCO$_2$Et-Ph, 4-NHCO$_2$Bn-Ph, 4-CH$_2$NHCO$_2$Me-Ph, 2-NHSO$_2$Me-Ph, 3-NHSO$_2$Me-Ph, 4-NHSO$_2$Me-Ph, 3-(1H-tetrazol-5-yl)-Ph, 4-(N-morpholinyl)-Ph, 4-[(1H-imidazol-2-yl)amino)]-Ph, 2,4-diF-Ph, 3,4-diCl-Ph, 3-CN-4-F-Ph, 4-CN-3-F-Ph, 3-CO$_2$H-4-NH$_2$-Ph, 3-CO$_2$H-5-NH$_2$-Ph, 3-CO$_2$Me-4-NH$_2$-Ph, 3-CO$_2$H-4-NHCOMe-Ph, 3-CO$_2$H-4-NHCO$_2$Me-Ph, 2-naphthyl, 2-CO$_2$H-thien-5-yl, 2-CO$_2$Me-thien-5-yl, 2-CONH$_2$-thien-5-yl, 2-(1H-tetrazol-5-yl)-thien-5-yl, pyrrol-3-yl, 2-NH$_2$-thiazol-4-yl, pyrid-2-yl, pyrid-3-yl, pyrid-4-yl, 2-NH$_2$-pyrid-3-yl, 2-NH$_2$-pyrid-5-yl, 2-NH$_2$-pyrid-6-yl, 2-CONH$_2$-pyrid-5-yl, 2-NHCO$_2$Me-pyrid-5-yl, 3-NH$_2$-benzisoxazol-5-yl, 3-NH$_2$-benzisoxazol-6-yl, 3-NH$_2$-indazol-5-yl, 3-NH$_2$-indazol-6-yl, 3-OH-indazol-5-yl, 3-OH-indazol-6-yl, quinolin-5-yl, 1-NH$_2$-phthalazin-6-yl, 4-NH$_2$-quinazolin-7-yl, 2-Me-4-NH$_2$-quinazolin-7-yl, 2,4-di-NH$_2$-quinazolin-7-yl,

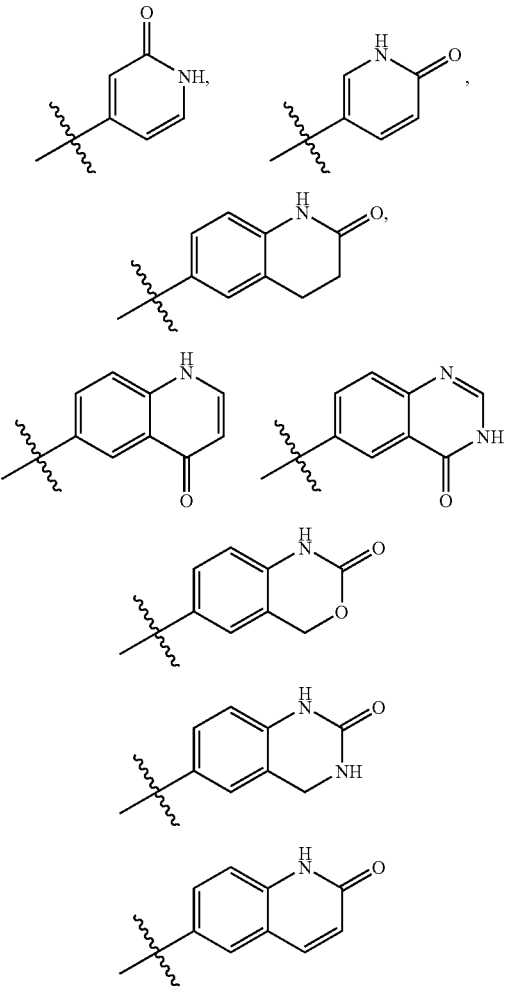

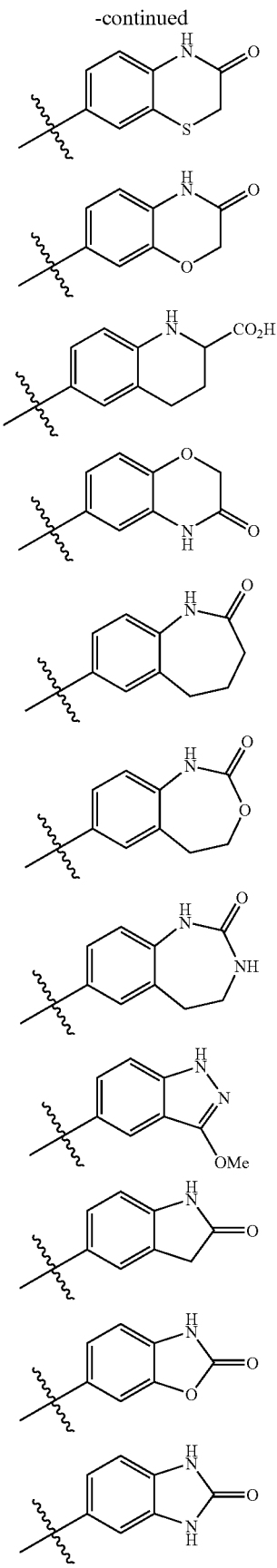

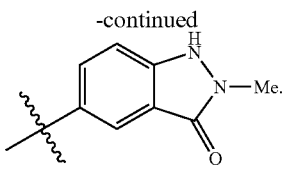

In another aspect, the present invention provides includes compounds of Formula (I) or stereoisomers, pharmaceutically acceptable salts, solvates, or prodrugs thereof, wherein: $R^3$ is Ph, 3-CF$_3$-Ph, 3-NH$_2$-Ph, 4-CH$_2$NH$_2$-Ph, 2-CH$_2$NMe$_2$-Ph, 3-OH-Ph, 3-OMe-Ph, 4-OMe-Ph, 4-CH$_2$OH-Ph, 4-CH$_2$OMe-Ph, 4-COMe-Ph, 3-CO$_2$H-Ph, 4-CO$_2$H-Ph, 4-CH$_2$CO$_2$H-Ph, 2-(CH$_2$)$_2$CO$_2$H-Ph, 3-(CH$_2$)$_2$CO$_2$H-Ph, 4-(CH$_2$)$_2$CO$_2$H-Ph, 3-CN-Ph, 4-CH$_2$CN-Ph, 3-CONH$_2$-Ph, 4-CONH$_2$-Ph, 3-CH$_2$CONH$_2$-Ph, 4-CH$_2$CONH$_2$-Ph, 3-NHCOMe-Ph, 4-NHCOMe-Ph, 2-NHCO$_2$Me-Ph, 3-NHCO$_2$Me-Ph, 4-NHCO$_2$Me-Ph, 4-CH$_2$NHCO$_2$Me-Ph, 2-NHSO$_2$Me-Ph, 3-NH SO$_2$Me-Ph, 4-NH SO$_2$Me-Ph, 3-(1H-tetrazol-5-yl)-Ph, 4-(N-morpholinyl)-Ph, 4-[(1H-imidazol-2-yl)amino)]-Ph, 3,4-diCl-Ph, 3-CO$_2$H-4-NH$_2$-Ph, 3-CO$_2$H-5-NH$_2$-Ph, 3-CO$_2$Me-4-NH$_2$-Ph, 3-CO$_2$H-4-NHCOMe-Ph, 3-CO$_2$H-4-NHCO$_2$Me-Ph, 2-NH$_2$-pyrid-5-yl, 2-NHCO$_2$Me-pyrid-5-yl, 2-CO$_2$H-thien-5-yl, 2-CO$_2$Me-thien-5-yl, 2-CONH$_2$-thien-5-yl, 2-(1H-tetrazol-5-yl)-thien-5-yl, 2-NH$_2$-thiazol-4-yl, pyrrol-3-yl, pyrid-4-yl, 3-NH$_2$-indazol-6-yl, 3-NH$_2$-benzisoxazol-6-yl, 2-naphthyl, quinolin-5-yl, 3-OH-indazol-5-yl, or

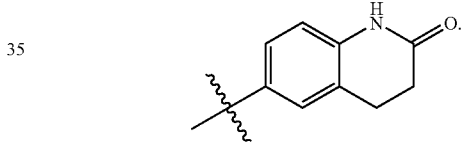

In another aspect, the present invention provides includes compounds of Formula (I) or stereoisomers, pharmaceutically acceptable salts, solvates, or prodrugs thereof, wherein: $R^{3a}$ is, independently at each occurrence, F, Cl, Br, Me, CN, OH, OMe, CH$_2$OH, CH$_2$OMe, CF$_3$, COMe, CO$_2$H, CO$_2$Me, —CH$_2$CO$_2$H, —(CH$_2$)$_2$CO$_2$H, —CH$_2$CO$_2$Me, —CH$_2$CO$_2$Et, —CH$_2$CN, —NHC(O)Me, —NHC(O)R$^{3b}$, —NHSO$_2$R$^{3c}$, —NHCO$_2$R$^{3c}$, —CH$_2$NHCO$_2$R$^{3c}$, —NHC(O)NR$^8$R$^9$, —NR$^7$R$^8$, —CH$_2$NR$^7$R$^8$, —S(O)$_p$NR$^8$R$^9$, —C(O)NR$^8$R$^9$, —CH$_2$C(O)NR$^8$R$^9$, —C(O)NHOR$^{3b}$, —C(=NH)NH$_2$, or —(CH$_2$)$_r$-5- to 6-membered heterocycle comprising: carbon atoms and 1-4 heteroatoms selected from N, O, and S(O)$_p$, wherein said heterocycle is substituted with 0-1 R$^{3d}$.

In another aspect, the present invention provides includes compounds of Formula (I) or stereoisomers, pharmaceutically acceptable salts, solvates, or prodrugs thereof, wherein: $R^{3a}$ is, independently at each occurrence, F, Cl, Br, Me, CN, OH, OMe, CH$_2$OH, CH$_2$OMe, CF$_3$, COMe, CO$_2$H, CO$_2$Me, —CH$_2$CO$_2$H, —(CH$_2$)$_2$CO$_2$H, —CH$_2$CO$_2$Me, —CH$_2$CO$_2$Et, —CH$_2$CN, NH$_2$, —CH$_2$NH$_2$, —CH$_2$NMe$_2$, —NHC(O)Me, —NHCO$_2$Me, —NHCO$_2$Et, —NHCO$_2$Bn, —NHCO$_2$iBu, —CH$_2$NHCO$_2$Me, —NHC(O)NH$_2$, —NHC(O)NHMe, —NHC(O)N(Me)$_2$, —NHSO$_2$Me, —SO$_2$NH$_2$, —SO$_2$NHMe, —CONH$_2$, —CONHMe, —CON(Me)$_2$, —CH$_2$CONH$_2$, —C(=NH)NH$_2$, —NH(1H-imidazol-2-yl), 1H-tetrazol-5-yl, or N-morpholinyl.

In another aspect, the present invention provides includes compounds of Formula (I) or stereoisomers, pharmaceutically acceptable salts, solvates, or prodrugs thereof, wherein: $R^4$ is, independently at each occurrence, H, F, Cl, Br, I, $CF_3$, $OCF_3$, CN, $NO_2$, $OR^a$, $SR^a$, —$C(O)R^a$, —$C(O)OR^a$, —$NR^7R^8$, —$C(O)NR^8R^9$, —$NR^8C(O)R^b$, —$NR^8C(O)OR^b$, —$NR^8C(O)NR^8$, —$S(O)_pNR^8R^9$, —$NR^8S(O)_pR^c$, —$S(O)R^c$, —$S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, —$(CH_2)_r$-phenyl substituted with 0-3 $R^{4b}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{4b}$.

In another aspect, the present invention provides includes compounds of Formula (I) or stereoisomers, pharmaceutically acceptable salts, solvates, or prodrugs thereof, wherein: $R^{11}$ is —$(CH_2)_rC(O)NR^7R^8$, —$C_{1-6}$ alkyl substituted with 0-2 $R^{11a}$, —$(CH_2)_s$-cyclohexyl substituted with 0-1 $R^{11b}$, —$(CH_2)_s$-phenyl substituted with 0-2 $R^{11b}$, —$(CH_2)_s$-naphthyl substituted with 0-2 $R^{11b}$, or —$(CH_2)_s$-heteroaryl substituted with 0-2 $R^{11b}$; wherein said heteroaryl is selected from: thienyl, furanyl, imidazolyl, thiazolyl, pyrrolyl, pyrazolyl, pyridyl, pyrimidyl, indolyl, indazolyl, benzofuranyl, benzothienyl, benzthiazolyl, benzimidazolyl, benzisoxazolyl, benzoxazolyl, quinazolinyl, phthalazinyl, 1,3-benzodioxolyl, oxazolyl, isoxazolyl, triazolyl, quinolinyl, and isoquinolinyl.

In another aspect, the present invention provides includes compounds of Formula (I) or stereoisomers, pharmaceutically acceptable salts, solvates, or prodrugs thereof, wherein: $R^{11}$ is —$(CH_2)_rC(O)NR^7R^8$, $C_{1-4}$ alkyl substituted with 0-2 $R^{11a}$, —$CH_2$-cyclohexyl substituted with 0-1 $R^{11b}$, —$CH_2$-phenyl substituted with 0-2 $R^{11b}$, —$CH_2$-naphthyl substituted with 0-2 $R^{11b}$, or —$(CH_2)_s$-heteroaryl substituted with 0-2 $R^{11b}$; wherein said heteroaryl is selected from: imidazol-4-yl, thiazol-4-yl, triazol-3-yl, oxazol-2yl, pyrid-2-yl, pyrid-3-yl, pyrid-4-yl, benzthiazol-2-yl, indol-3-yl, indol-5-yl, indol-6-yl, indazol-6-yl, indazol-5-yl, benzimidazol-6-yl, and benzimidazol-2-yl.

In another aspect, the present invention provides includes compounds of Formula (I) or stereoisomers, pharmaceutically acceptable salts, solvates, or prodrugs thereof, wherein: $R^{11}$ is —$(CH_2)_s$-cyclohexyl substituted with 0-1 $R^{11b}$, —$(CH_2)_s$-phenyl substituted with 0-2 $R^{11b}$, —$(CH_2)_s$-naphthyl substituted with 0-2 $R^{11b}$, or —$(CH_2)_s$-heteroaryl substituted with 0-2 $R^{11b}$; wherein said heteroaryl is selected from: thienyl, furanyl, imidazolyl, thiazolyl, pyrrolyl, pyrazolyl, pyridyl, pyrimidyl, indolyl, indazolyl, benzofuranyl, benzothienyl, benzthiazolyl, benzimidazolyl, benzisoxazolyl, benzoxazolyl, quinazolinyl, phthalazinyl, 1,3-benzodioxolyl, oxazolyl, isoxazolyl, triazolyl, quinolinyl, and isoquinolinyl.

In another aspect, the present invention provides includes compounds of Formula (I) or stereoisomers, pharmaceutically acceptable salts, solvates, or prodrugs thereof, wherein: $R^{11}$ is —$CH_2$-phenyl substituted with 0-2 $R^{11b}$, —$CH_2$-naphthyl substituted with 0-2 $R^{11b}$, or —$(CH_2)_s$-heteroaryl substituted with 0-2 $R^{11b}$; wherein said heteroaryl is selected from: imidazol-4-yl, thiazol-4-yl, triazol-3-yl, oxazol-2yl, pyrid-2-yl, pyrid-3-yl, pyrid-4-yl, benzthiazol-2-yl, indol-3-yl, indol-5-yl, indol-6-yl, indazol-6-yl, indazol-5-yl, benzimidazol-6-yl, and benzimidazol-2-yl.

In another aspect, the present invention provides includes compounds of Formula (I) or stereoisomers, pharmaceutically acceptable salts, solvates, or prodrugs thereof, wherein: $R^{11}$ is benzyl, —$C(O)NHCH_2$-pyrid-2-yl, or 3-[C(O)NMePh]-benzyl.

In another embodiment, the present invention provides a novel pharmaceutical composition, comprising: a pharmaceutically acceptable carrier and a therapeutically effective amount of a compound of the present invention.

In another embodiment, the present invention provides a novel process for making a compound of the present invention.

In another embodiment, the present invention provides a novel intermediate for making a compound of the present invention.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In a preferred embodiment, the present invention provides a pharmaceutical composition wherein the additional therapeutic agent is an antihypertensive agent selected from ACE inhibitors, AT-1 receptor antagonists, ET receptor antagonists, dual ET/AII receptor antagonists, and vasopepsidase inhibitors, an antiarrythmic agent selected from IKur inhibitors, or an antithrombotic agent selected from anticoagulants selected from thrombin inhibitors, other factor XIa inhibitors, other kallikrein inhibitors, factor VIIa inhibitors and factor Xa inhibitors, and antiplatelet agents selected from GPIIb/IIIa blockers, $P2Y_1$ and $P2Y_{12}$ antagonists, thromboxane receptor antagonists, and aspirin, or a combination thereof.

In a preferred embodiment, the present invention provides pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent clopidogrel.

In another embodiment the present invention provides a method for modulation of the coagulation cascade and/or contact activation system comprising administering to a patient in need of such treatment a therapeutically effective amount of at least one of the compounds of the present invention.

In another embodiment, the present invention provides a novel method for treating thromboembolic disorders comprising: administering to a patient in need of such treatment a therapeutically effective amount of at least one of the compounds of the present invention.

In another embodiment, the present invention provides a novel method, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the present invention provides a novel method, wherein the thromboembolic disorder is selected unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention.

In another embodiment, the present invention provides a method, wherein the inflammatory disorder is selected from the group consisting of sepsis, acute respiratory distress syndrome, and systemic inflammatory response syndrome.

In another embodiment, the present invention provides a novel method of treating a patient in need of thromboembolic disorder treatment, comprising: administering a compound of the present invention in an amount effective to treat a thromboembolic disorder.

In another embodiment, the present invention provides a method of treating a patient in need of inflammatory disorder treatment, comprising: administering a compound of the present invention in an amount effective to treat an inflammatory disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a thromboembolic and/or inflammatory disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a thromboembolic and/or inflammatory disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel method, comprising: administering a compound of the present invention in an amount effective to treat a thromboembolic and/or inflammatory disorder.

In another embodiment, the present invention provides a compound of the present invention for use in therapy.

In another embodiment, the present invention also provides the use of a compound of the present invention for the manufacture of a medicament for the treatment of a thromboembolic and/or inflammatory disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

Compounds of this invention may have one or more asymmetric centers. Unless otherwise indicated, all chiral (enantiomeric and diastereomeric) and racemic forms of compounds of the present invention are included in the present invention. Many geometric isomers of olefins, $C=N$ double bonds, and the like can also be present in the compounds, and all such stable isomers are contemplated in the present invention. Accordingly, the present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo. "Haloalkyl" refers to branched and straight-chained, having one or more halogen substituents. Example haloalkyl groups include, but are not limited to, $CF_3$, $C_2F_5$, $CHF_2$, $CCl_3$, $CHCl_2$, $C_2Cl_5$, and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy, and the like. Similarly, "alkylthio" or "thioalkoxy" represents an alkyl group as defined above with the indicated number of carbon atoms attached through a sulfur bridge; for example methyl-S—, ethyl-S—, and the like.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulfur bridge; for example trifluoromethyl-S—, pentafluoroethyl-S—, and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (retrain). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, phenanthranyl, and the like.

Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., $N \rightarrow O$ and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, sulfate, and the like.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide ($N \rightarrow O$) derivative. In cases wherein there are quaternary carbon atoms on compounds of the present invention, these may be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^2$, then said group may optionally be substituted with up to three $R^2$ groups and $R^2$ at each occurrence is selected independently from the definition of $R^2$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to acid or base salts of the compounds described herein. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference in its entirety. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs,* edited by H. Bundgaard, (Elsevier, 1985), and *Methods in Enzymology,* Vol. 42, at pp. 309-396, edited by K. Widder, et. al. (Academic Press, 1985);

b) *A Textbook of Drug Design and Development,* edited by Krosgaard-Larsen and H. Bundgaard, Chapter 5, "Design and Application of prodrugs," by H. Bundgaard, at pp. 113-191 (1991);

c) H. Bundgaard, *Advanced Drug Delivery Reviews,* Vol. 8, p. 1-38 (1992);

d) H. Bundgaard, et al., *Journal of Pharmaceutical Sciences,* Vol. 77, p. 285 (1988); and e) N. Kakeya, et. al., *Chem Phar Bull.,* Vol. 32, p. 692 (1984).

Preparation of prodrugs is well known in the art and described in, for example, *Medicinal Chemistry: Principles and Practice,* ed. F. D. King, The Royal Society of Chemistry, Cambridge, UK, 1994, which is incorporated herein by reference in its entirety.

Isotopically labeled compounds of the present invention, i.e., wherein one or more of the atoms described are replaced by an isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

It should further be understood that solvates (e.g., hydrates) of the compounds of the present invention are also with the scope of the present invention. Methods of solvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor XIa and/or plasma kallikrein. "Therapeutically effective amount" is also intended to include an amount of the combination of compounds claimed that is effective to inhibit factor XIa and/or plasma kallikrein. The combination of compounds is preferably a synergistic combination. Synergy, as described, for example, by Chou and Talalay, *Adv. Enzyme Regul.* 1984, 22:27-55, occurs when the effect (in this case, inhibition of factor XIa and/or plasma kallikrein) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., Mack Publishing Company, Easton, Pa., 1985, which is incorporated herein by reference in its entirety.

"α", "β", "R", "S", "E", and "Z" are stereochemical designations familiar to one skilled in the art. One stereoisomer of a compound of Formula I may display superior activity compared with the others. Thus, each stereoisomer of a compound of Formula I is considered to be a part of the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. Enantiomerically pure compounds of this invention can be prepared by asymmetric synthesis.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "atm" for atmosphere, "psi" for pounds per square inch, "conc." for concentrate, "sat" or "sat'd " for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LC-MS" for liquid chromatography mass spectrometry, "HPLC" for high pressure liquid chromatography, "RP HPLC" for reverse phase HPLC, "TLC" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "tlc" for thin layer chromatography.

| | |
|---|---|
| Me | methyl |
| Et | ethyl |
| AcOH | acetic acid |
| MeOH | methanol |
| EtOH | ethanol |
| EtOAc | ethyl acetate |
| Et$_2$O | diethyl ether |
| i-PrOH or IPA | isopropanol |
| HOAc | acetic acid |
| Ph | phenyl |
| Bn | benzyl |
| t-Bu | tertiary butyl |
| BOP reagent | benzotriazol-1-yloxytris (dimethylamino)phosphonium hexafluorophosphate |
| BBr$_3$ | boron tribromide |
| BINAP | rac-2,2'-Bis(diphenylphosphino)-1,1'-binaphthyl |
| Boc | tert-butyloxycarbonyl |
| 2MeS-ADP | 2 methylthio adenosine diphosphate |
| cDNA | complimentary DNA |
| CH$_2$Cl$_2$ | dichloromethane |
| CH$_3$CN | acetonitrile |
| Cs$_2$CO$_3$ | cesium carbonate |
| DBAD | Di-tert-butylazodicarboxylate |
| DCE | 1,2 dichloroethane |
| DCM | dichloromethane |
| DCC | dicyclohexylcarbodiimide |
| DEAD | Diethylazodicarboxyalte |
| DIBAL-H | diisobutylaluminum hydride |
| DIC or DIPCDI | diisopropylcarbodiimide |
| DIEA | diethylpropyl amine |
| DIPEA | N,N,-diisopropylethylamine |
| DMEM | Dulbecco's modified Eagle media |
| DME | 1,2-dimethoxyethane |
| DMF | dimethyl formamide |
| DMSO | dimethyl sulfoxide |
| EDC (or EDC•HCl) or EDCI (or EDCI•HCl) or EDAC | 3-ethyl-3'-(dimethylamino)propyl-carbodiimide hydrochloride (or 1-(3-dimethylamino-propyl)-3-ethylcarbodiimide hydrochloride) |
| EDTA | ethylenediaminetetraacetic acid |
| FBS | Fetal Bovine Serum |
| HCl | hydrochloric acid |
| HEPES | 4-(2-hydroxyethyl)piperaxine-1-ethanesulfonic acid |
| Hex | hexane |
| HOBt | 1-hydroxybenzotriaole hydrate |
| Hunig's base | N,N-diisopropylethyl amine |
| LDA | Lithium diisopropylamide |
| LiHMDS | Lithium bis(trimethylsilyl amide) |
| mCPBA | meta-chloroperbenzoic acid |
| D-PBS | Dulbecco's Phosphate Buffered Saline |
| Pd/C | palladium on carbon |
| PCy$_3$ | tricyclohexyl phosphine |
| SCX | Strong Cation Exchanger |
| TFA | trifluoroacetic acid |
| THF | tetrahydrofuran |
| TRIS | tris (hydroxymethyl) aminomethane |
| KOAc | potassium acetate |
| K$_3$PO$_4$ | potassium phosphate |
| LiHMDS | lithium hexamethyldisilazide |
| MgSO$_4$ | magnesium sulfate |
| Na$_2$SO$_3$ | sodium sulfite |
| Na$_2$SO$_4$ | sodium sulfate |
| NH$_4$Cl | ammonium chloride |
| NH$_4$OH | ammonium hydroxide |
| Pd$_2$(dba)$_3$ | tris(dibenzylideneacetone)dipalladium (0) |
| Pd(dppf)Cl$_2$•CH$_2$Cl$_2$ | [1,1'-bis(diphenylphosphino)ferrocene]dichloropalladium(II), complex with dichloromethane |
| Pd(Ph$_3$P)$_4$ | tetrakis(triphenylphosphine) palladium (0) |
| (Ph$_3$P)$_2$PdCl$_2$ | bis(triphenylphosphme)palladium dichloride |

Solution ratios express a volume relationship, unless stated otherwise. NMR chemical shifts ($\delta$) are reported in parts per million. Flash chromatography was carried out on silica gel according to Still's method (Still, W. C. et al. *J. Org. Chem.* 1978, 43, 2923).

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis,* Wiley-Interscience, 3$^{rd}$ Edition, 1999).

All references cited herein are hereby incorporated in their entirety herein by reference.

Representative biaryl compounds of this invention can be prepared as shown in Scheme 1. Using a modification of the procedure described by Hart, D. J. et al. (*J. Org. Chem.,* 1983, 48(3), 289-294), in situ generation of N-trimethylsilylaldimines from appropriately substituted benzaldehydes (1a) and lithium bis(trimethylsilyl)amide, followed by the addition of Grignard or alkyllithium reagents (1b) gives, after aqueous work, up the primary amine 1c. Alternately, organozinc reagents can be used for the addition to the N-trimethylsilylaldimines. (see: Miginiac, L. et al., *J. Organometallic Chem.,* 1997, 548, 269., Miginiac, L. et al., *J. Organometallic Chem.,* 1991, 420, 155; Katritzky, A. R. et al., *J. Org. Chem.,* 1995, 60, 3405.; Umani-Ronchi, A. et al., *J. Org. Chem.,* 1994, 59, 7766.; Villieras, J. et al., *Tetrahedron Asymmetry,* 1996, 7(6), 1835.; and Staas, D. D. et al., *J. Org. Chem.,* 2002, 67, 8276.) Amide coupling between 1c and appropriately substituted carboxylic acids (1d), for example Boc-tranexamic acid, employing suitable coupling reagents, such as EDCI, HOBt, and base, generates 1e (for other suitable coupling conditions see: Han, S-Y; Kim, Y-A. *Tetrahedron,* 2004, 60, 2447). Suzuki coupling between 1e and an appropriately substituted aryl or heteroarylboronic acid or ester 1f in the presence of a base such as anhydrous potassium phosphate, cesium carbonate, aqueous sodium carbonate, or aqueous potassium carbonate, in a solvent such as DMSO, dioxane, DME, or toluene, using a catalyst such as $Pd_2(dba)_3$/tri-t-butylphosphonium tetrafluoroborate, $Pd(Ph_3P)_4$, or $Pd(dppf)Cl_2 \cdot CH_2Cl_2$, provides biaryl compounds of formula 1g. Further manipulation of functional groups on A using methods known to one skilled in the art of organic synthesis will give additional compounds 1g of the invention. For instance, when A is a Boc-tranexamic acid moiety, the Boc group can be deprotected with TFA to give the aminomethylcyclohexyl derivative. Likewise, further manipulation of functional groups on $R^3$ and $R^4$ using methods known to one skilled in the art of organic synthesis will give additional compounds of the invention.

is also understood that further manipulation of functional groups on A, $R^3$ and $R^4$ using methods known to one skilled in the art of organic synthesis provides additional compounds of this invention.

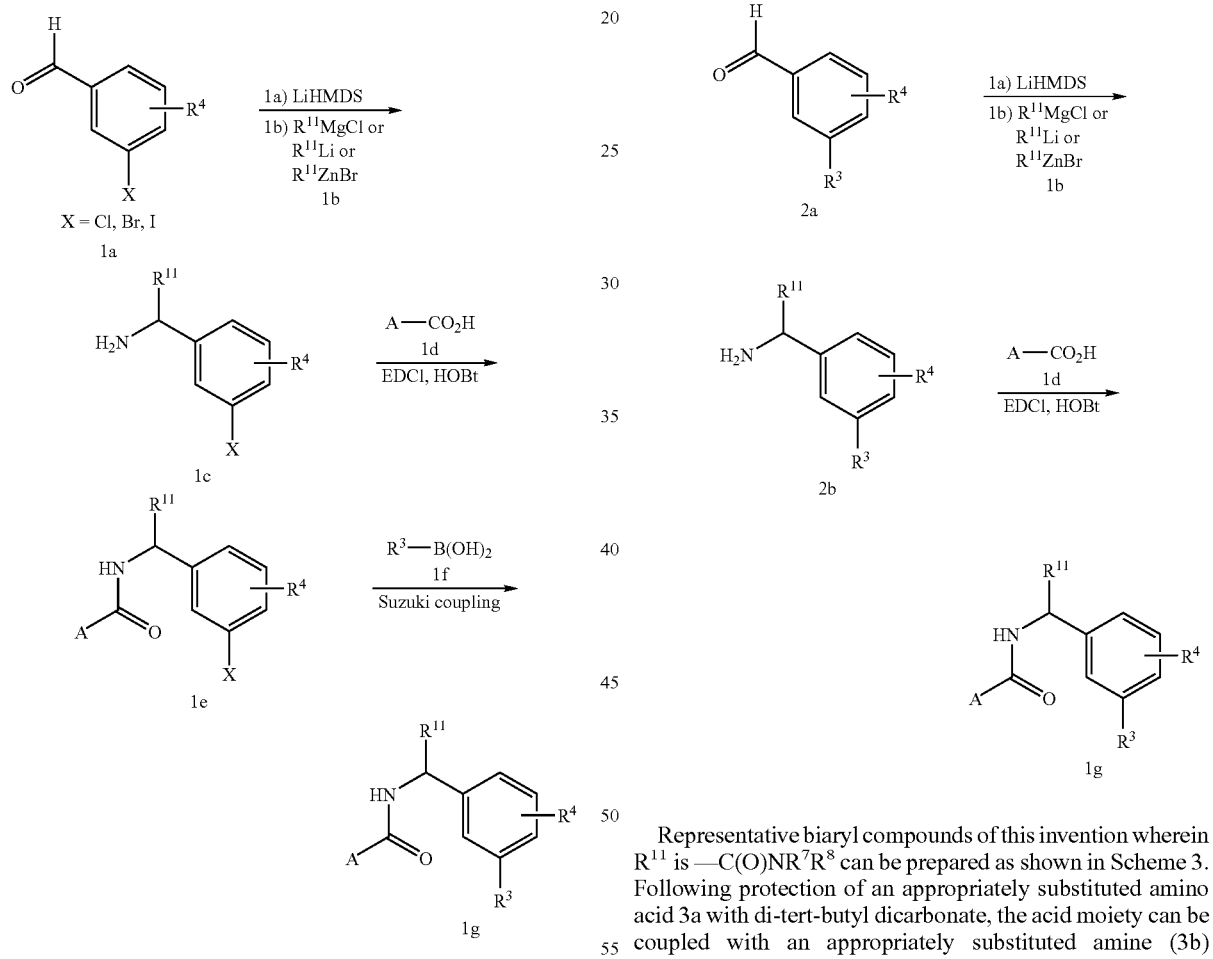

Alternately, the $R^3$ moiety can be introduced earlier in the synthesis as shown in Scheme 2. A Suzuki coupling between appropriately substituted benzaldehydes 1a and an appropriately substituted aryl or heteroarylboronic acid or ester 1f, using conditions described above for the conversion of 1e to 1g, provides compounds of formula 2a which can be converted to primary amines 2b using the methods described for the conversion of 1a to 1c. Amide coupling between 2b and appropriately substituted carboxylic acids (1d), employing suitable coupling reagents, as previously described for the conversion of 1c to 1e, generates compounds of formula 1g. It Representative biaryl compounds of this invention wherein $R^{11}$ is $—C(O)NR^7R^8$ can be prepared as shown in Scheme 3. Following protection of an appropriately substituted amino acid 3a with di-tert-butyl dicarbonate, the acid moiety can be coupled with an appropriately substituted amine (3b) employing suitable coupling reagents, as previously described for the conversion of 1c to 1e, to give amide 3c. Deprotection with TFA and coupling of the resulting amine with appropriately substituted carboxylic acids (1d) employing suitable coupling reagents as previously described for the conversion of 1c to 1e, gives 3d. Suzuki coupling between 3d and an appropriately substituted aryl or heteroarylboronic acid or ester 1f using conditions described above for the conversion of 1e to 1g, provides compounds of formula 3e. Further manipulation of functional groups on A, $R^3$ and $R^4$ using methods known to one skilled in the art of organic synthesis will give additional compounds of the invention.

33

Scheme 3

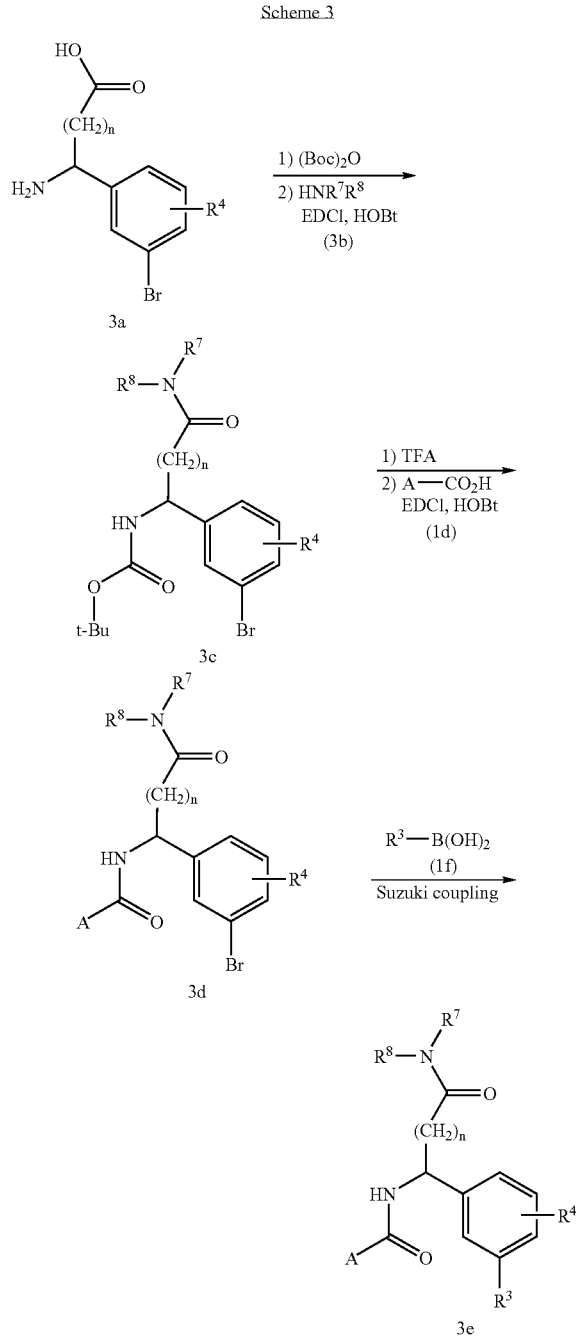

34

In cases where suitably substituted aldehydes are not commercially available, additional aldehydes useful for the synthesis of compounds in Scheme 1 and 2 are accessible from a variety of straightforward chemical transformations known to one skilled in the art. As outlined in Scheme 4, aldehydes 4c suitable for use in preparing compounds of this invention may be obtained through oxidation of the corresponding alcohols or halides 4a as taught in "*Advanced Organic Chemistry*" (Jerry March, Wiley Interscience, 4th Edition, p 1167-1171, 1190, and 1193 and references therein). Alternatively, suitable aldehydes may be prepared by hydrogenation of the corresponding carboxylic acids 4b in the presence of palladium complexes and pivalic anhydride (Nagayama et al. *Chemistry Letters* 1998, 27, 1143-1144) or by reduction of the corresponding carboxylic acid 4b with borane followed by oxidation of the intermediate alcohol with manganese dioxide or Dess-Martin periodinane. In addition, the ester (4b; R=alkyl) can be reduced with DIBAL-H (Chandrasekhar et al. *Tetrahedron Letters* 1998, 39, 909-910) to give the aldehyde 4c. Additional aryl aldehydes may be obtained from the corresponding toluene derivatives 4d by direct oxidation or by a two step procedure which involves formation of the dibromide intermediate and subsequent conversion to the aldehyde with a silver salt, hexamethylenetetramine, or morpholine (with silver: Demir, A. S.; Reis, O. *Tetrahedron*, 2004, 60, 3803; hexamethylenetetramine: Tidwell, R. R.; et al. *J. Med. Chem.*, 1978, 21(7), 613; morpholine: published PCT application WO 2002/32884). Additional suitable aldehydes may be prepared through formylation of the aromatic ring of 4e as taught in "*Advanced Organic Chemistry*" (Jerry March, Wiley Interscience, 4th Edition, p 542-546 and references therein).

Scheme 4

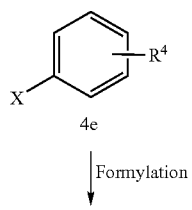

4e

Formylation

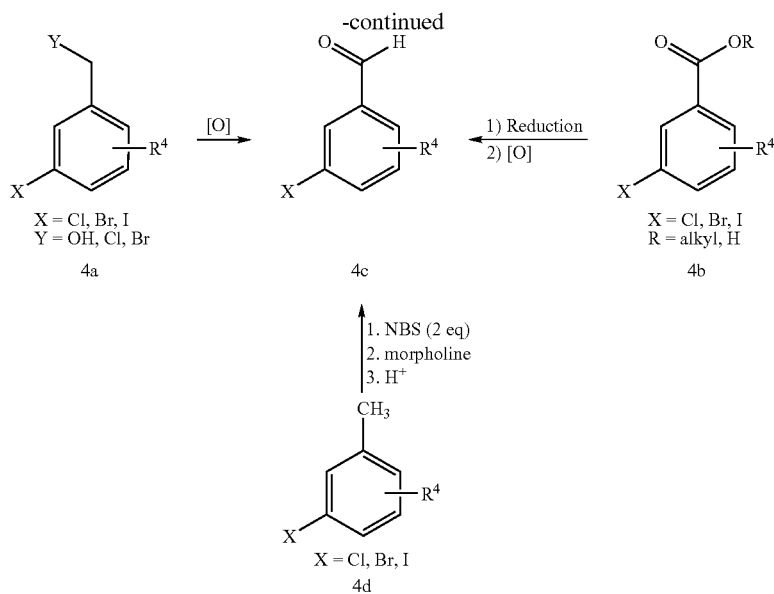

A suitably substituted carboxylic acid (A-CO$_2$H, 1d) is used in the amide coupling shown in Scheme 1-3. Many of these carboxylic acids are commercially available. In cases where the carboxylic acids are not commercially available, they can be prepared using methods known in the art (Scheme 5). Carboxylic acids suitable for use in preparing compounds of this invention may be obtained through oxidation of the corresponding alcohol 5a or aldehyde 5b as taught in "Advanced Organic Chemistry" (Jerry March, Wiley Interscience, 4$^{th}$ Edition, p 1196 and 701-703 and references therein). Alternately, oxidation of aromatic side chains in 5c gives aromatic carboxylic acids as taught in "Advanced Organic Chemistry" (Jerry March, Wiley Interscience, 4$^{th}$ Edition, p 1183-1184 and references therein). Alternately, hydrolysis of esters 5d or nitriles 5e yields the carboxylic acid as taught in "Advanced Organic Chemistry" (Jerry March, Wiley Interscience, 4$^{th}$ Edition, p 378-383 and 887-889 and references therein). Alternately, carbonylation of bromide 5f gives the carboxylic acid as taught in "Advanced Organic Chemistry" (Jerry March, Wiley Interscience, 4$^{th}$ Edition, p 484-486, 546-547, and 664-665 and references therein). The R$^1$ and R$^2$ groups can be further manipulated using methods known in the art to provide additional compounds of this invention. For example, when R$^1$ is a cyano group, it can be reduced to give CH$_2$NH$_2$ with a suitable reducing agent. The cyano can also be converted to an amidine by reaction with either hydroxylamine followed by hydrogenolysis with a palladium catalyst under a hydrogen atmosphere or via a Pinner reaction followed by ammonolysis.

Scheme 5

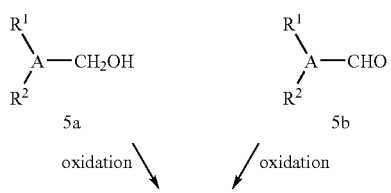

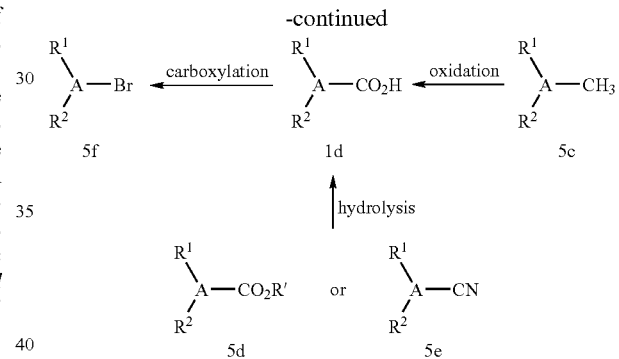

Schemes 6 and 7 describe the synthesis of specific examples of A-CO$_2$H (1d) useful for preparing compounds of this invention. When A is an isoquinoline moiety a modification of the procedure from published U.S. patent application US2004/77865 is followed. Heating 2-methyl benzonitrile derivative 6a with 1-(t-butoxy)-N—N—N'—N'-tetramethylmethanediamine in a suitable solvent such as DMF gives the enamine 6b. Condensation of enamine 6b and 2,4-dimethoxybenzylamine in DMPU at elevated temperatures gives the 1-imino-1,2-dihydroisoquinoline skeleton and subsequent hydrolysis provides 6c. Debenzylation of 6c with anisole in TFA at elevated temperatures provides 1-amino-isoquinoline 6d. When A is a 5,6,7,8-tetrahydroisoquinoline moiety, a modified procedure described by McEachem is followed (McEachem, E. J. et al. *J. Org. Chem.* 2002, 67, 7890). Acid 6c is converted to the ester 6e. Debenzylation of 6e with anisole in TFA at elevated temperatures and acetylation with acetyl chloride and triethylamine yields 6f. Hydrogenation over platinum oxide in the presence of TFA provides the 1-amino-5,6,7,8-tetrahydroisoquinoline. Saponification of the ester with NaOH and hydrolysis of the amide under acidic conditions gives 6g.

Scheme 6

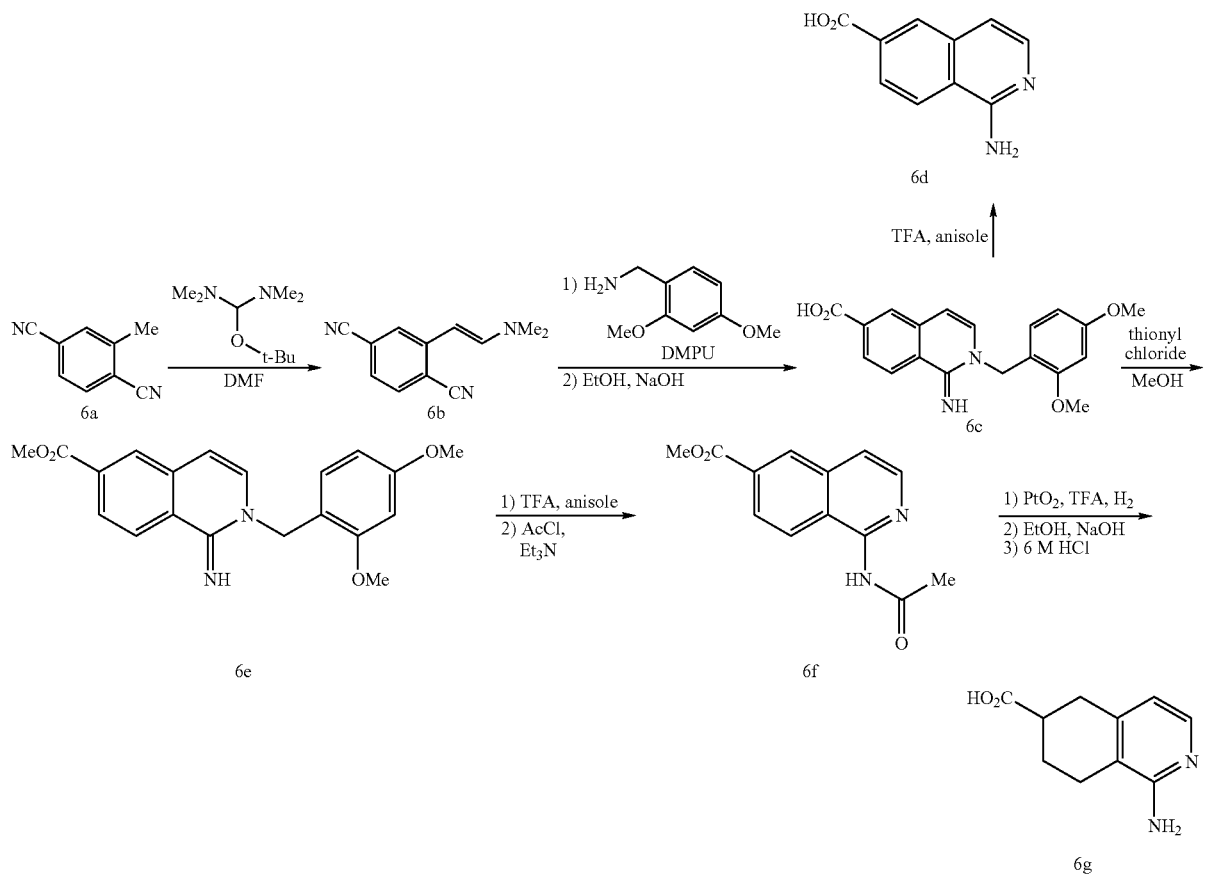

Scheme 7 describes the synthesis of specific examples of A-CO$_2$H (1d) when A is a 4-amino-quinazoline moiety. Heating an appropriately substituted ortho-fluoro benzonitrile such as 7a with either formamidine acetate or acetamidine acetate in DMA, according to a modification of the procedure described by Lam et al. (*J. Med. Chem.* 2003, 46, 440 5) gives 4-amino quinazoline 7b and 7c, respectively. Saponification of the ester under basic conditions provides 7d and 7e.

Scheme 7

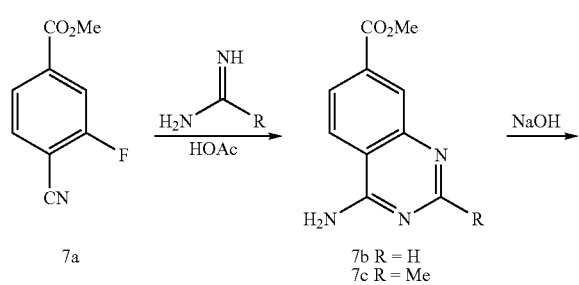

-continued

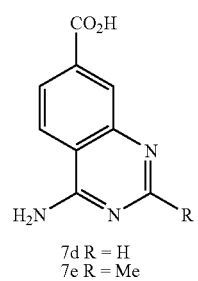

7d R = H
7e R = Me

In cases where suitably substituted boronic acids are not commercially available, a modification to this approach may be adopted wherein an aryl halide is subjected to a palladium mediated coupling with a diboron species such as bis(pinacolato) diboron to provide the corresponding 4,4,5,5-tetramethyl-[1,3,2]dioxaborolane intermediate using the method of Ishiyama, T. et al. (*J. Org. Chem.* 1995, 60(23), 7508-7510). Alternately, this same intermediate can be prepared by reaction of the intermediate halide with the corresponding dialkoxyhydroborane as described by Murata, M. et al. (*J. Org. Chem.* 1997, 62(19), 6458-6459). The boron pinacolate intermediates can be used in place of boronic acids for coupling to the aryl halides or triflates or the boron pinacolate intermediate can be converted to the corresponding boronic acids. Alternately, the requisite boronic acids can be prepared by metal-halogen exchange of suitably substituted aryl halides followed by quenching with a trialkoxyborate reagent, followed by aqueous workup to provide the boronic acid (Miyaura, N.; Suzuki, A. *Chem. Review,* 1995, 95, 2457).

It is also realized that the scope of intermediate synthesis can be further extended outside the use of Suzuki methodology since the precursor aryl halides or triflates described above are also precursors for Stille, Negishi, Hiyama, and Kumada-type cross coupling methodologies (Tsuji, J. *Transition Metal Reagents and Catalysts: Innovations in Organic Synthesis,* John Wiley & Sons, 2000; Tsuji, J. *Palladium Reagents and Catalysts: Innovations in Organic Synthesis,* John Wiley & Sons, 1996.)

The synthesis of specific examples of biaryl compounds of this invention are depicted in Scheme 8-10. In situ generation of N-trimethylsilylaldimines from appropriately substituted benzaldehydes 8a and lithium bis(trimethylsilyl)amide, followed by the addition of benzylmagnesium chloride gives, after aqueous work up, the primary amine 8b. Amide coupling between 8b and Boc-tranexamic acid employing EDCI, HOBt, and base in DMF generates 8c. Suzuki coupling between 8c and 4-cyano-3-fluorophenylboronic acid, or 4-CO$_2$Me-3-fluorophenylboronic acid, or 4-CO$_2$H-3-fluorophenylboronic acid provides the biaryl scaffold. Deprotection with TFA provides 8d-f. Heating 8d and 8e/8f with hydrazine monohydrate in n-butanol gives the 3-aminoindazole 8g and the 3-hydroxy indazole 8h, respectively. Reacting 8d with acetohydroxamic acid and potassium tert-butoxide in DMF according to a modification of the procedure described by Palermo, M. G. (*Tetrahedron Letters,* 1996, 37(17), 2885) provides 3-aminobenzisoxazole 8i. Alternately, heating the Boc-protected precursor of 8d with formamidine acetate or acetamidine acetate in DMA, according to a modification of the procedure described by Lam (Lam, P. Y. S. et al, *J. Med. Chem.* 2003, 46, 4405.) and then deprotection with TFA gives 4-amino quinazolines 8j and 8k. Alternately, heating 8m with formamide, according to a modification of the procedure described in patent application EP 30156, gives 8j. Quinazolinone 8l may be prepared similarly by heating the corresponding anthranilic acid derivatives 8n with formamide as described by Alexandre et al. (*Tetrahedron. Lett.* 2002 43, 3911) followed by deprotection with TFA. Alternatively, quinazolinone 8l can be prepared in two steps by heating 8o with ammonium acetate and trimethylorthoformate, according to a modification of the procedure described in published PCT application WO2005/012264, followed by deprotection with TFA.

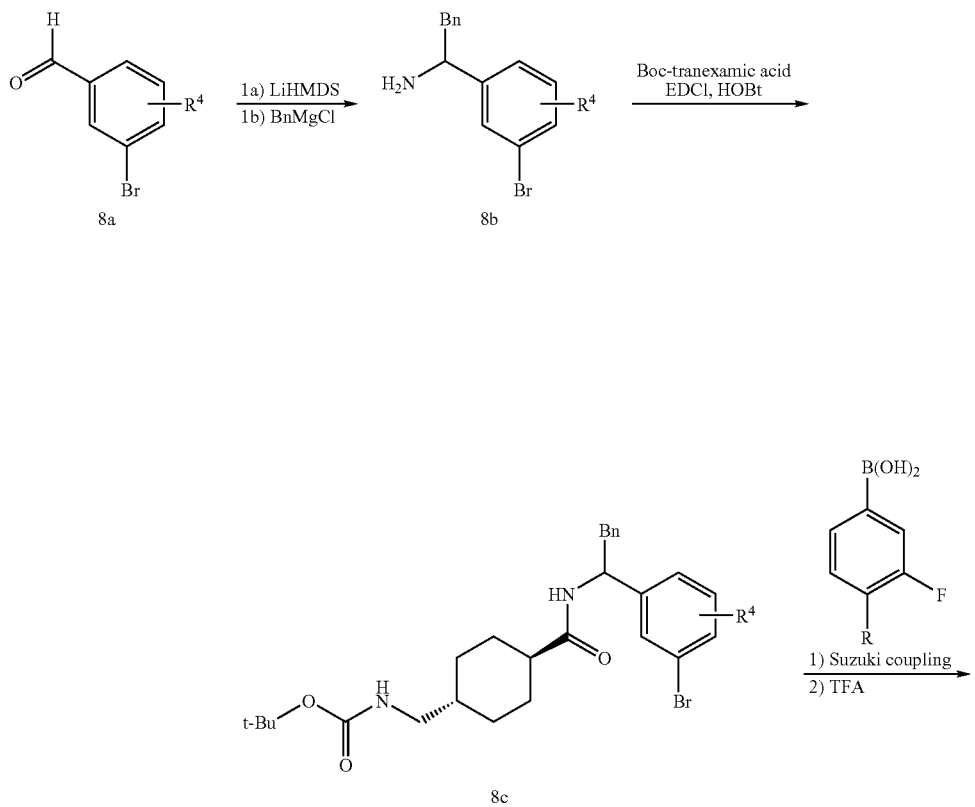

-continued

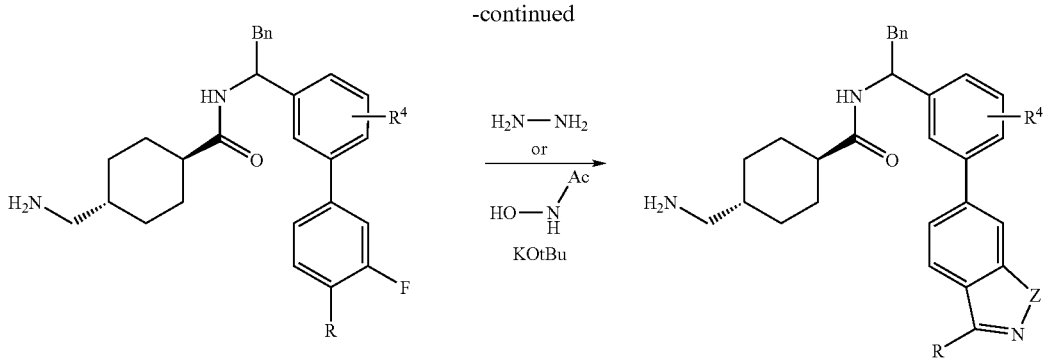

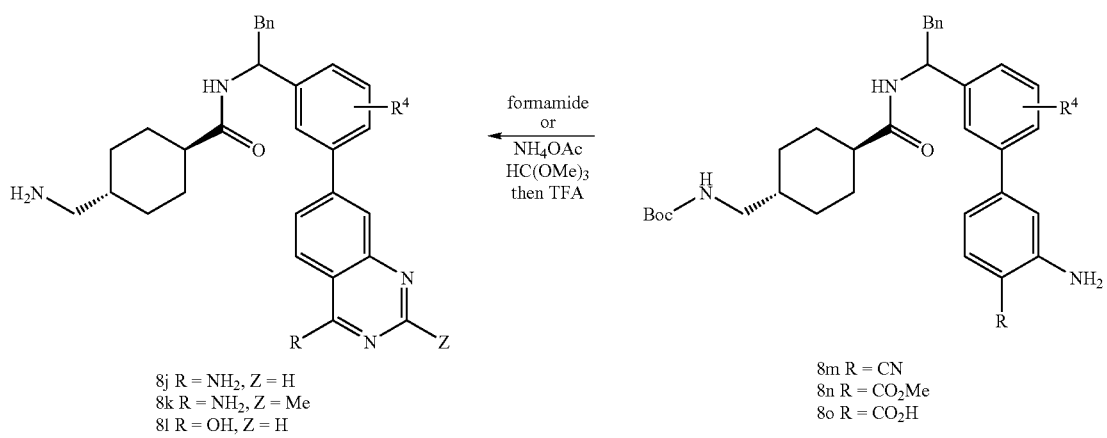

Alternatively, in situ generation of N-trimethylsilylaldimines from substituted 3-phenylbenzaldehydes 9a and lithium bis(trimethylsilyl)amide (Scheme 9), followed by the addition of benzylmagnesium chloride gives, after aqueous work up, the primary amine 9b. Amide coupling between 9b and Boc-tranexamic acid employing EDCI, HOBt, and base in DMF generates 9c. Deprotection with TFA provides 9d.

Scheme 9

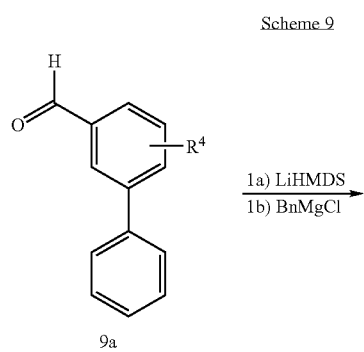

-continued

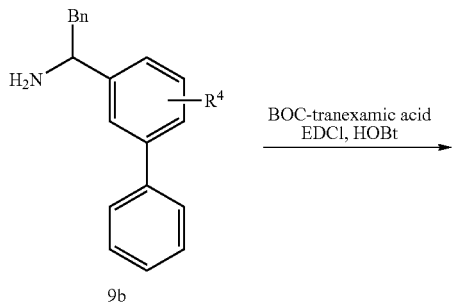

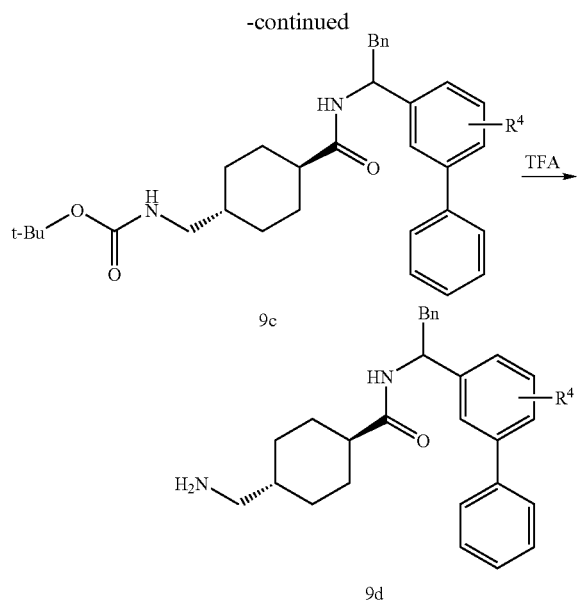

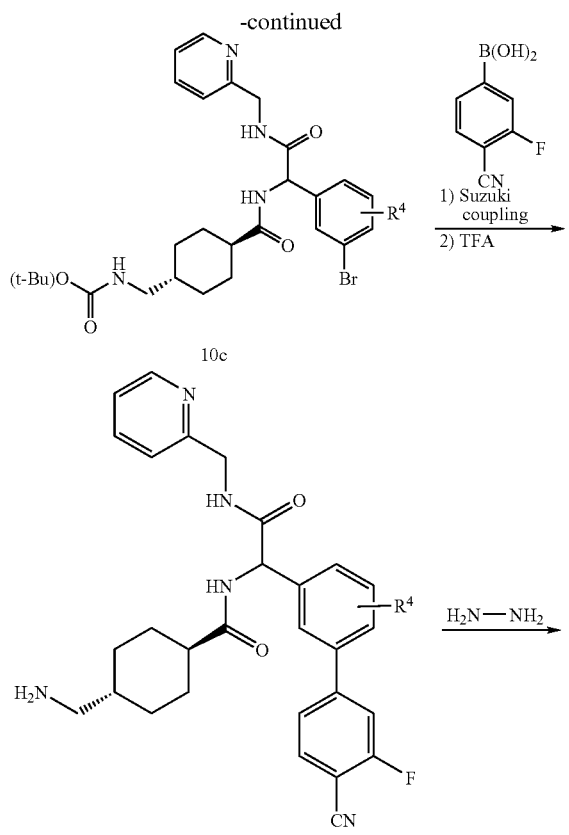

The specific preparation of compounds of the current invention wherein $R^{11}$ is —C(O)NR$^7$R$^8$ is depicted in Scheme 10. Following protection of amino acid 10a with di-tert-butyl dicarbonate, the acid moiety was coupled with 2-aminomethyl pyridine employing EDCI, HOBt, and Hunig's base in DMF to give 10b. Deprotection with TFA and coupling of the resulting amine with Boc-tranexamic acid as described above generates amide 10c. Suzuki coupling between 10c and 4-cyano-3-fluorophenylboronic acid in the presence of Pd(Ph$_3$P)$_4$ and aqueous sodium carbonate in dimethoxyethane provides the biaryl scaffold. Deprotection with TFA provides 10d. Heating 10d and hydrazine monohydrate in n-butanol gives the 3-amino indazole 10e. The 2-fluorobenzonitrile 10d can also be converted to the 3-amino benzisoxazole and 4-amino quinazoline moieties are described previously in Scheme 8.

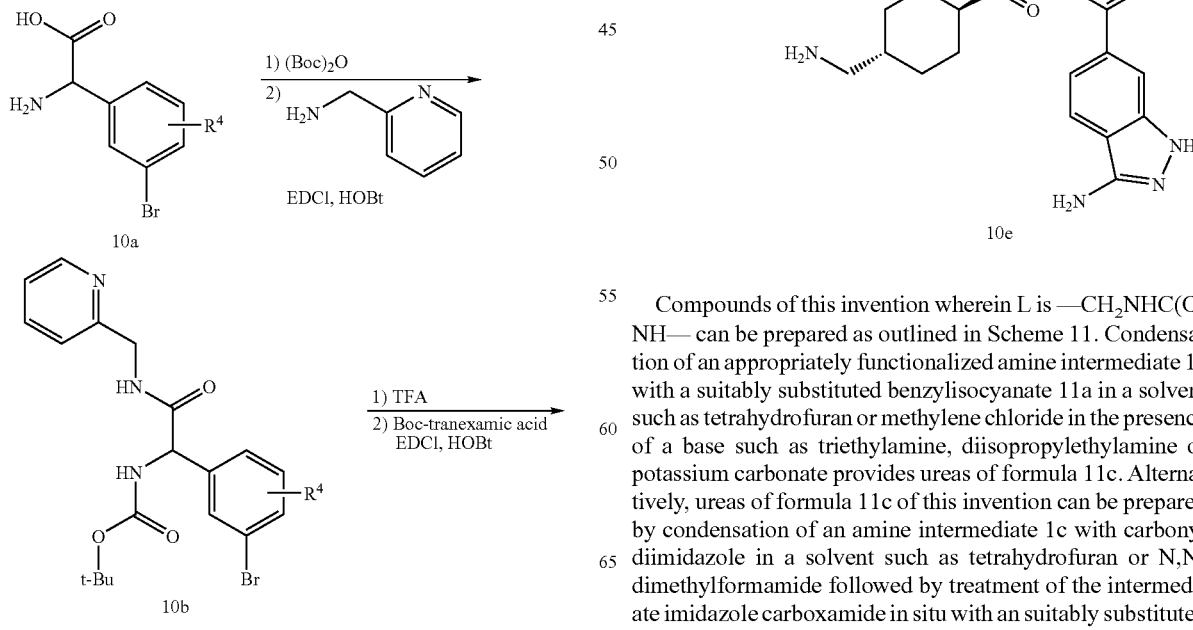

Compounds of this invention wherein L is —CH$_2$NHC(O)NH— can be prepared as outlined in Scheme 11. Condensation of an appropriately functionalized amine intermediate 1c with a suitably substituted benzylisocyanate 11a in a solvent such as tetrahydrofuran or methylene chloride in the presence of a base such as triethylamine, diisopropylethylamine or potassium carbonate provides ureas of formula 11c. Alternatively, ureas of formula 11c of this invention can be prepared by condensation of an amine intermediate 1c with carbonyl diimidazole in a solvent such as tetrahydrofuran or N,N-dimethylformamide followed by treatment of the intermediate imidazole carboxamide in situ with an suitably substituted benzyl amine 11b. Urea linked compounds of this invention of formula 11c can also be prepared by condensation of amine intermediate 1c with p-nitrophenylchloroformnate in the presence of a suitable base such as triethylamine, followed by treatment of the resulting p-nitrophenylcarbamate with an appropriate substituted amine 11b. It is understood that amine intermediate 1c can be replaced with either amine intermediates 2b or the Boc-deprotected derivative of 3c to afford additional compounds of the invention.

Scheme 11

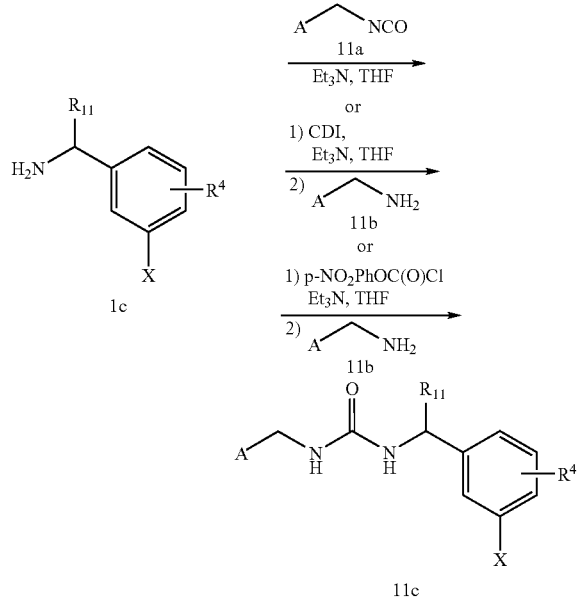

Isocyanates of formula 11a used in Scheme 11 above are either commercially available or can be readily prepared from the corresponding amines 11b by treatment with phosgene or by various other methods known in the art (see for example, H. Eckert & B. Forster, *Angew. Chem. Int. Ed.* 1987, 26, 894; H. Knolker & T. Braxmeier, *Synlett*, 1997, 925; S. Porwanski et al. *Tetrahedron Lett.* 2004, 45, 5027). Amines of formula 11b are also available commercially or can be prepared by those knowledgeable in the art from a variety of easily accessible starting materials such as nitrites, aldehydes, alcohols, halides, acids and esters by methods including, but not limited to those outlined in Scheme 12.

Scheme 12

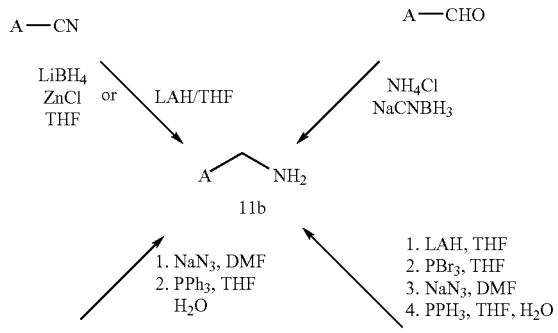

-continued

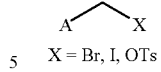

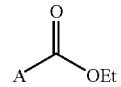

Other features of the invention will become apparent in the course of the following descriptions of exemplary embodiments that are given for illustration of the invention and are not intended to be limiting thereof.

The following Examples have been prepared, isolated and characterized using the methods disclosed herein. The following Examples demonstrate a partial scope of the invention and are not meant to be limiting of the scope of the invention.

EXAMPLES

Example 1

4-Aminomethyl-cyclohexanecarboxylic acid (1-biphenyl-3-yl-2-phenyl-ethyl)-amide 1A. 1-Biphenyl-3-yl-2-phenyl-ethylamine: To a cooled (0° C.), clear, colorless solution of 3-phenylbenzaldehyde (0.500 g, 2.74 mmol) in THF (5.5 mL) was added dropwise 1.0 M LiHMDS (3.0 mL, 3.01 mmol) in THF. After 15 min., a solution of 2.0 M benzylmagnesium chloride (1.6 mL, 3.30 mmol) in THF was added dropwise. After 15 min, the reaction was quenched with sat. NH$_4$Cl and the reaction was warmed to rt. The reaction was extracted with diethyl ether. The combined organic layers were washed with sat. NaHCO$_3$, brine, dried over Na$_2$SO$_4$, filtered and concentrated to give 0.930 g of compound 1A as a clear, yellow oil. Prep HPLC [Phenomenex Luna 30×250 mm; 20 min. grad.; 40-100% B; 30 mL/min.; Solvent A: 90% H$_2$O, 10% methanol, 0.1% TFA; Solvent B: 10% H$_2$O, 90% methanol, 0.1% TFA] gave 0.636 g (60%, clear, colorless oil) of the benzylamine as the TFA salt. $^1$H NMR (400 MHz, MeOD$_4$) δ: 7.65-7.62 (m, 1H), 7.56-7.54 (m, 3H), 7.49 (d, J=7.9 Hz, 1H), 7.46-7.41 (m, 2H), 7.38-7.32 (m, 2H), 7.29-7.20 (m, 3H), 7.15-7.13 (m, 2H), 4.60 (dd, J=8.8, 6.6 Hz, 1H), 3.35 (dd, J=13.6, 7.2 Hz, 1H), 3.24 (dd, J=13.6, 8.8 Hz, 1H).

HRMS m/z calc'd. for C$_{20}$H$_{20}$N (M+H)$^+$=274.1596. Found 274.1604.

1B. Example 1: To a cooled (0° C.), clear, colorless solution of compound 1A (0.228 g, 0.59 mmol) in DMF (1.96 mL) was added Hunig's base (0.22 mL, 1.3 mmol). Next BOC-tranexamic acid (0.166 g, 0.65 mmol), HOBt (0.119 g, 0.88 mmol), and EDC (0.169, 0.88 mmol) were added sequentially. After 15 min., the reaction was warmed to rt. After 6 h, water (4 mL) was added to the reaction to give a white suspension and the reaction was extracted with CH$_2$Cl$_2$ (2×). The combined organic layers were washed with 1.0 N HCl, sat. NaHCO$_3$, brine, dried over MgSO$_4$, filtered, and concentrated to give a white solid. Methylene chloride (7 mL) was added to give a white suspension and then TFA (3 mL) was added. The resulting clear, colorless solution was stirred at rt for 30 min. and then concentrated. Prep HPLC [Phenomenex Luna 21.2×100 mm; 8 min. grad.; 40-100% B; 20 mL/min.; Solvent A: 90% H$_2$O, 10% methanol, 0.1% TFA; Solvent B: 10% H$_2$O, 90% methanol, 0.1% TFA] gave 0.206 g (66%, white solid) of Example 1 as the TFA salt. $^1$H NMR (500 MHz, MeOD$_4$) δ: 8.45 (d, J=8.2 Hz, 1H), 7.56 (d, J=7.2 Hz, 2H), 7.52 (s, 1H), 7.48 (d, J=7.7 Hz, 1H), 7.41 (t, J=8.2 Hz, 2H), 7.38 (t, J=7.7 Hz, 1H), 7.34-7.29 (m, 2H), 7.25-7.20 (m, 4H), 7.18-7.15 (m, 1H), 5.24-5.19 (m, 1H), 3.12 (dd, J=13.8, 6.6 Hz, 1H), 3.04 (dd, J=13.8, 9.4 Hz, 1H), 2.75 (d, 7.2 Hz, 2H), 2.18 (tt, J.=12.0, 3.30 Hz, 1H), 1.83-1.75 (m, 3H), 1.65-1.62 (m, 1H), 1.57-1.52 (m, 1H), 1.44-1.29 (m, 2H), 1.06-0.99 (m, 2H). HRMS m/z calc'd. for $C_{28}H_{33}N_2O$ $(M+H)^+$ =413.2593. Found 413.2595.

Example 2

4-Aminomethyl-cyclohexanecarboxylic acid {1-[3-(3-amino-1H-indazol-6-yl)-phenyl]-2-phenyl-ethyl}-amide 2A. 1-(3-Bromo-phenyl)-2-phenyl-ethylamine: The benzylamine was prepared following the procedure for compound 1A by replacing 3-phenylbenzaldehyde with 3-bromobenzaldehyde. Chiral separation of 1.0 g of benzylamine on Chiralcel OJ (5% IPA in Heptane) gave 0.414 g (99% ee) of enantiomer A and 0.393 g (97% ee) of enantiomer B. Each enantiomer was reacted with (S)-(+)-α-methoxyphenyl acetic acid according to Trost (Trost, B. M. et al., *J. Org. Chem.* 1994, 59, 4202.) for determination of the absolute stereochemistry of each. Enantiomer A possessed the (R)-absolute stereochemistry and enantiomer B possessed the (S)-absolute stereochemistry. $^1$H NMR (500 MHz, CDCl$_3$) δ: 7.54 (t, J=1.6 Hz, 1H), 7.38-7.37 (m, 1H), 7.30 (t, J=7.2 Hz, 2H), 7.26-7.21 (m, 2H), 7.19 (d, J=7.7 Hz, 1H), 7.16 (d, J=7.2 Hz, 2H), 4.16 (dd, J=8.8, 5.0 Hz, 1H), 2.98 (dd, J=13.2, 5.0 Hz, 1H), 2.78 (dd, J=13.2, 8.8 Hz, 1H), 1.46 (bs, 2H). LCMS m/z $(M-NH_3+H)^+$=259.1 and $(M+2-NH_3+H)^+$=261.1. Enantiomer A: $[α]_D^{25}$=−13.7 (c=1.04; CHCl$_3$). Enantiomer B: $[α]_D^{25}$=+12.8 (c=1.01; CHCl$_3$)

2B. {4-[1-(3-Bromo-phenyl)-2-phenyl-ethylcarbamoyl]-cyclohexylmethyl}-carbamic acid tert-butyl ester: To a cooled (0° C.), clear, colorless solution of racemic benzylamine from 2A (1.0 g, 3.62 mmol) in DMF (12 mL) was added BOC-tranexamic acid (1.02 g, 3.98 mmol), HOBt (0.734 g, 5.43 mmol), and EDC (1.04 g, 5.43 mmol). After 15 min., the reaction was warmed to rt. After 4 h, water (25 mL) was added to the reaction to give a white suspension and the reaction was extracted with CH$_2$Cl$_2$ (2×). The combined organic layers were washed with 1.0 N HCl, sat. NaHCO$_3$, brine, dried over MgSO$_4$, filtered, and concentrated to give a white solid weighing 2.0 g. The crude material was triturated with MeOH. The solid was collected to give 1.51 g (80%) of compound 2B as a white solid. $^1$H NMR (500 MHz, CDCl$_3$) δ: 7.38-7.35 (m, 2H), 7.27-7.19 (m, 3H), 7.16 (t, J=7.4 Hz, 1H), 7.12 (d, J=7.7 Hz, 1H), 7.05 (d, J=6.6 Hz, 2H), 5.71 (d, J=7.7 Hz, 1H), 5.23 (q, J=7.7 Hz, 1H), 4.59-4.55 (m, 1H), 3.11 (dd, J=14.0, 6.4 Hz, 1H), 3.00 (dd, J=14.0, 8.0 Hz, 1H), 2.95 (t, J=6.3 Hz, 2H), 1.96 (tt, J=12.1, 3.4 Hz, 1H), 1.83-1.72 (m, 4H), 1.43 (s, 9H), 1.43-1.29 (m, 3H), 0.94-0.87 (m, 2H). LCMS m/z $(M−C_4H_9+H)^+$=459 and $(M+2−C_4H_9+H)^+$=461.1.

2C. 4-Aminomethyl-cyclohexanecarboxylic acid [1-(4'-cyano-3'-fluoro-biphenyl-3-yl)-2-phenyl-ethyl]-amide: To a flame-dried 1 dram vial was placed compound 2B (0.250 g, 0.485 mmol), Pd$_2$(dba)$_3$ (0.0220 g, 0.024 mmol), tri-tert-butylphosphonium tetrafluoroborate (0.0168 g, 0.058 mmol), Cs$_2$CO$_3$ (0.316 g, 0.97 mmol), and 4-cyano-3-fluorophenylboronic acid (0.199 g, 0.97 mmol). The vial was purged with argon for several minutes and then degassed dioxane (2.5 mL) was added. The vial was sealed with a teflon-lined cap. The suspension was stirred at rt for 1 h and then the vial was placed in a preheated oil bath (90° C.). After 22 h, the reaction was cooled to rt and diluted with CH$_2$Cl$_2$. The reaction was filtered through a nylon filter (0.45 μm) and the filtrate was concentrated. The residue was dissolved in CH$_2$Cl$_2$, 28% NH$_4$OH was added, and the biphasic mixture was stirred vigorously for 15 min. The layers were separated and the organic layer was washed with brine, dried over MgSO$_4$, filtered, and concentrated to give the biphenyl compound as a yellow solid.

BOC-deprotection: The yellow solid was dissolved in 30% TFA in CH$_2$Cl$_2$ (15 mL) to give an orange solution. After 30 min., the reaction was concentrated. Purification by Prep HPLC [Phenomenex Luna 30×250 mm; 20 min. grad.; 30-100% B; 30 mL/min.; Solvent A: 90% H$_2$O, 10% methanol, 0.1% TFA; Solvent B: 10% H$_2$O, 90% methanol, 0.1% TFA] gave 0.020 g (7.2%, white solid) of the biphenyl cyclohexyl methyl amine derivative as the TFA salt. $^1$H NMR (500 MHz, MeOD$_4$) δ: 8.47 (d, J=8.8 Hz, 1H), 7.79 (dd, J=8.0, 6.9 Hz, 1H), 7.59-7.53 (m, 4H), 7.47-7.42 (m, 2H), 7.25-7.22 (m, 2H), 7.20-7.16 (m, 3H), 5.25-5.20 (m, 1H), 3.11 (dd, J=13.7, 6.6 Hz, 1H), 3.06 (dd, J=13.7, 9.4 Hz, 1H), 2.76 (d, J=7.1 Hz, 2H), 2.19 (tt, J=12.1, 3.6 Hz, 1H), 1.84-1.75 (m, 3H), 1.67-1.64 (m, 1H), 1.60-1.52 (m, 1H), 1.44-1.30 (m, 2H), 1.07-0.99 (m, 2H). LCMS m/z $(M+H)^+$=456.4.

2D. Example 2: Indazole formation: A suspension of compound 2C (0.020 g, 0.035 mmol), n-butanol (0.35 mL), and hydrazine monohydrate (0.13 mL, 4.2 mmol) was microwaved in a Personal Chemistry Emrys™ Optimizer microwave at 150° C. for 10 min. The resulting clear, colorless solution was concentrated to give Example 2 as a white solid. Purification by Prep HPLC [Phenomenex Luna 21.2×100 mm; 8 min. grad.; 20-100% B; 20 mL/min.; Solvent A: 90% H$_2$O, 10% methanol, 0.1% TFA; Solvent B: 10% H$_2$O, 90% methanol, 0.1% TFA] gave 0.0183 g (90%, white solid) of the title compound as the TFA salt. $^1$H NMR (500 MHz, MeOD$_4$) δ: 8.51 (d, J=8.25 Hz, 1H), 7.96 (d, J=8.8 Hz, 1H), 7.57-7.54 (m, 3H), 7.47 (m, 3H), 7.26-7.16 (m, 5H), 5.26-5.21 (m, 1H), 3.13 (dd, J=14.0, 6.9 Hz, 1H), 3.08 (dd, J=14.0, 9.1 Hz, 1H), 2.76 (d, J=7.1 Hz, 2H), 2.20 (tt, J=12.0, 3.3 Hz, 1H), 1.84-1.76 (m, 3H), 1.68-1.65 (m, 1H), 1.59-1.53 (m, 1H), 1.45-1.31 (m, 2H), 1.07-0.99 (m, 2H).

HRMS m/z calc'd. for $C_{29}H_{34}N_5O$ $(M+H)^+$=468.2763. Found 468.2754.

Example 3

4-Aminomethyl-cyclohexanecarboxylic acid {1-[3-(3-amino-1H-indazol-6-yl)-5-bromo-phenyl]-2-phenyl-ethyl}-amide 3A. {4-[1-(3,5-Dibromo-phenyl)-2-phenyl-ethylcarbamoyl]-cyclohexylmethyl}-carbamic acid tert-butyl ester. The benzylamine was prepared following the procedure from 1A by replacing 3-phenylbenzaldehyde with 3,5-dibromobenzaldehyde. The benzylamine was coupled with the BOC-tranexamic acid according to the procedure from 2B to give the amide. $^1$H NMR (500 MHz, CDCl$_3$) δ: 7.52 (t, J=1.6 Hz, 1H), 7.29-7.21 (m, 5H), 7.04 (d, J=7.2 Hz, 2H), 5.78 (d, J=7.7 Hz, 1H), 5.16 (dd, J=14.3, 7.7 Hz, 1H), 4.58 (bs, 1H), 3.08 (dd, J=14.3, 6.0 Hz, 1H), 2.95-2.88 (m, 3H), 1.95 (tt, J=12.1, 3.3 Hz, 1H), 1.78-1.76 (m, 3H), 1.71-1.66 (m, 1H), 1.42 (s, 9H), 1.41-1.24 (m, 3H), 0.93-0.84 (m, 2H). LCMS m/z $(M−C_4H_9+H)^+$=537.2 and $(M+2−C_4H_9+H)^+$=539.2 and $(M+4−C_4H_9+H)^+$=541.2.

3B. {4-[1-(5-Bromo-4'-cyano-3'-fluoro-biphenyl-3-yl)-2-phenyl-ethylcarbamoyl]-cyclohexylmethyl}-carbamic acid tert-butyl ester: To a flame-dried flask was added compound 1A (0.750 g, 1.26 mmol), Pd(Ph$_3$P)$_4$ (0.0728 g, 0.063 mmol), and 4-cyano-3-fluorophenyl boronic acid (0.208 g, 1.26 mmol). The flask was purged with argon for several minutes and then degassed toluene (6.4 mL) and degassed 2.0 M Na$_2$CO$_3$ (3.8 mL) were added. The suspension was warmed to reflux to give a biphasic solution. After 30 min., the reaction became a viscous, milky white suspension so additional degassed toluene (3.2 mL) and degassed 2.0 M $Na_2CO_3$ (1.9 mL) were added. After 18.5 h, the reaction was cooled to rt and diluted with water and EtOAc. The layers were separated and the organic layer which contained solid was filtered through a Buchner funnel. The solid was rinsed with EtOAc to give a gray solid weighing 0.450 g. Trituration from $CH_2Cl_2$ (20 mL) gave 0.387 g of the biphenyl compound as a gray solid. The crude material was used without further purification. LCMS m/z $(M+H)^+$=578.3 and $(M+2+H)^+$=580.3.

3C. Example 3. BOC-deprotection and indazole formation: Compound 3B (0.0257 g, 0.040 mmol) was dissolved in 30% TFA in $CH_2Cl_2$ (4 mL) to give a clear, colorless solution. After 1 h, the reaction was concentrated to give a clear, brown oil. A mixture of the brown oil, hydrazine monohydrate (0.4 mL) and n-butanol (1.0 mL) was microwaved in a Personal Chemistry Emrys™ Optimizer microwave at 150° C. for 10 min. The reaction was concentrated. Purification by Prep HPLC [Phenomenex Luna 21.2×100 mm; 8 min. grad.; 30-100% B; 20 mL/min.; Solvent A: 90% $H_2O$, 10% methanol, 0.1% TFA; Solvent B: 10% $H_2O$, 90% methanol, 0.1% TFA] gave 0.0147 g (55%, white solid) of Example 3 as the TFA salt. $^1H$ NNR (500 MHz, $MeOD_4$) δ: 8.52 (d, J=8.3 Hz, 1H), 7.97 (d, J=8.3 Hz, 1H), 7.72 (s, 1H), 7.58 (s, 1H), 7.53 (s, 1H), 7.50 (s, 1H), 7.39 (dd, J=8.5, 1.4 Hz, 1H), 7.27-7.24 (m, 2H), 7.21-7.18 (m, 3H), 5.22-5.17 (m, 1H), 3.13-3.05 (m, 2H), 2.76 (d, J=7.2 Hz, 2H), 2.20 (tt, J=12.1, 3.4 Hz, 1H), 1.85-1.77 (m, 3H), 1.68-1.65 (m, 1H), 1.59-1.53 (m, 1H), 1.46-1.30 (m, 2H), 1.09-1.00 (m, 2H). HRMS m/z calc'd. for $C_{29}H_{33}N_5OBr$ $(M+H)^+$=546.1868. Found 546.1874.

Example 4

4-Aminomethyl-cyclohexanecarboxylic acid {1-[3-(3-amino-1H-indazol-6-yl)-5-methyl-phenyl]-2-phenyl-ethyl}-amide To a flame-dried 1-dram vial was placed compound 3B (0.075 g, 0.118 mmol), $Pd(dppf)Cl_2 \cdot CH_2Cl_2$ (0.0048 g, 0.0059 mmol), $K_3PO_4$ (0.100 g, 0.472 mmol), and methyl boronic acid (0.0282 g, 0.472 mmol). The vial was purged with argon for several minutes and then degassed DMSO (0.78 mL) was added. The vial was sealed with a Teflon-lined screw cap and the vial was placed in a preheated oil bath (85° C.). After 8 h, the reaction was cooled to rt. The reaction was diluted with $CH_2Cl_2$ (75 mL), washed with water, brine, dried over $MgSO_4$, filtered, and concentrated to give a yellow-brown residue weighing 0.071 g. Boc-deprotection followed by indazole formation according to 3C gave 0.0172 g (24%, white solid) of Example 4 as the TFA salt. $^1H$ NMR (500 MHz, $MeOD_4$) δ: 8.47 (d, J=8.3 Hz, 1H), 7.97 (d, J=8.3 Hz, 1H), 7.53 (s, 1H), 7.45 (dd, J=8.8, 1.1 Hz, 1H), 7.39 (s, 1H), 7.36 (s, 1H), 7.28-7.16 (m, 6H), 5.22-5.18 (m, 1H), 3.11 (dd, J=13.7, 6.6 Hz, 1H), 3.06 (dd, J=13.7, 9.4 Hz, 1H), 2.76 (d, J=6.6 Hz, 2H), 2.42 (s, 3H), 2.20 (tt, J=12.0, 3.3 Hz, 1H), 1.84-1.76 (m, 3H), 1.67-1.64 (m, 1H), 1.60-1.52 (m, 1H), 1.46-1.30 (m, 2H), 1.08-0.99 (m, 2H). HRMS m/z calc'd. for $C_{30}H_{36}N_5O$ $(M+H)^+$=482.2920. Found 482.2906.

Example 5

4-Aminomethyl-cyclohexanecarboxylic acid {1-[3-(3-amino-1H-indazol-6-yl)-5-ethyl-phenyl]-2-phenyl-ethyl}-amide Example 5 was prepared as the TFA salt starting with compound 3B and following the procedure from Example 4, replacing methyl boronic acid with triethylborane. $^1H$ NMR (500 MHz, $MeOD_4$) δ: 8.48 (d, J=8.3 Hz, 1H), 7.94 (d, J=8.8 Hz, 1H), 7.53 (s, 1H), 7.44 (dd, J=8.5, 1.4 Hz, 1H), 7.40 (s, 1H), 7.38 (s, 1H), 7.26-7.23 (m, 3H), 7.21-7.16 (m, 3H), 5.22-5.18 (m, 1H), 3.12-3.04 (m, 2H), 2.76 (d, J=7.1 Hz, 2H), 2.72 (q, J=7.7 Hz, 2H), 2.24-2.16 (m, 1H), 1.84-1.76 (m, 3H), 1.67-1.64 (m, 1H), 1.60-1.50 (m, 1H), 1.46-1.34 (m, 2H), 1.28 (t, J=7.7 Hz, 3H), 1.09-0.99 (m, 2H). HRMS m/z calc'd. for $C_{31}H_{38}N_5O$ $(M+H)^+$=496.3076. Found 496.3064.

Example 6

4-Aminomethyl-cyclohexanecarboxylic acid {1-[3-amino-5-(3-amino-1H-indazol-6-yl)-phenyl]-2-phenyl-ethyl}-amide To a flame-dried 1 dram vial was placed compound 3B (0.075 g, 0.118 mmol), palladium acetate (0.0026 g, 0.0118 mmol), BINAP (0.0110 g, 0.0177 mmol), and $Cs_2CO_3$ (0.0992 g, 0.283 mmol). The vial was purged with argon for several minutes and then degassed DMSO (0.80 mL) was added followed by benzophenone imine (0.040 mL, 0.236 mmol). The vial was sealed with a teflon cap and placed in a preheated oil bath (85° C.). After 16.5 h, the reaction was stopped, cooled to rt, poured into water and extracted with $CH_2Cl_2$ (5×10 mL). The combined organic layers were washed with brine, dried over $MgSO_4$, filtered, and concentrated to give 0.118 g of the imine as a yellow residue. The residue was dissolved in THF (1 mL) and 4.0 M HCl in dioxane (1.0 mL) was added followed by water (0.5 mL). After 17.5 h, the reaction was concentrated to give the crude aniline derivative. The residue was dissolved in 30% TFA in $CH_2Cl_2$ (5 mL) to give a clear, yellow solution. After 1 h, the reaction was concentrated. Purification by Prep HPLC [Phenomenex Luna 21.2×100 mm; 8 min. grad.; 30-100% B; 20 mL/min.; Solvent A: 90% $H_2O$, 10% methanol, 0.1% TFA; Solvent B: 10% $H_2O$, 90% methanol, 0.1% TFA] gave 0.034 g (off-white solid) of the cyclohexyl methyl amine derivative as the TFA salt. LCMS m/z $(M+H)^+$=471.4. Indazole formation was accomplished following the procedure from 2D to give 0.0204 g (24%, off-white solid) of Example 6 as the bis-TFA salt. $^1H$ NMR (500 MHz, $MeOD_4$) δ: 8.03 (d, J=8.8 Hz, 1H), 7.62 (d, J=1.1 Hz, 1H), 7.59 (s, 1H), 7.54 (d, J=1.6 Hz, 1H). 7.46 (d, J=8.8 Hz, 1H), 7.38 (d, J=1.6 Hz, 1H), 7.26-7.18 (m, 5H), 5.24 (t, J=7.7 Hz, 1H), 3.14 (d, J=7.7 Hz, 2H), 2.76 (d, J=7.2 Hz, 2H), 2.23 (tt, J=12.1, 3.3 Hz, 1H), 1.85-1.77 (m, 3H), 1.70-1.67 (m, 1H), 1.60-1.54 (m, 1H), 1.45-1.31 (m, 2H), 1.08-1.00 (m, 2H). HRMS m/z calc'd. for $C_{29}H_{35}N_6O$ $(M+H)^+$=483.2872. Found 483.2883.

Example 7

4-Aminomethyl-cyclohexanecarboxylic acid {1-[3-(3-amino-1H-indazol-6-yl)-5-hydroxy-phenyl]-2-phenyl-ethyl}-amide To a flame-dried 1 dram vial was placed compound 3B (0.075 g, 0.118 mmol), $Pd(dppf)Cl_2 \cdot 9CH_2Cl_2$ (0.0048 g, 0.0059 mmol), KOAc (0.0347 g, 0.354 mmol), and bis(pinacolato)diboron (0.0329 g, 0.130 mmol). The vial was purged with argon for several minutes and then degassed DMSO (0.80 mL) was added, the vial was sealed with a Teflon-lined cap and then placed in a preheated oil bath (85° C.). After 8 h, the reaction was stopped, cooled to rt, poured into water and extracted with $CH_2Cl_2$ (5×). The combined organic layers were washed with brine, dried over $MgSO_4$, filtered, and concentrated to give 0.107 g of the boronate as a brown solid.

The boronate was oxidized to the phenol according to a modified procedure from Maleczka (Maleczka et al. *J. Am. Chem. Soc.*, 2003, 125, 7792.). Acetone (0.80 mL) was added to give a brown solution. A minor suspension of Oxone® in water (0.0725 g in 0.40 mL in water) was added. An exotherm was observed. Added additional Oxone® in water (2×0.0725 g in 0.40 mL in water) over the course of 1 h. The reaction was quenched with sat. $Na_2SO_3$ and extracted with $CH_2Cl_2$ (3×). The combined organic layers were washed with brine, dried over $MgSO_4$, filtered and concentrated to give 0.075 g of the crude phenol as a brown residue.

BOC-deprotection and indazole formation was accomplished following the procedure from 3C to give 0.0174 g (31%, off-white solid) of Example 7 as the TFA salt. $^1$H NMR (500 MHz, $MeOD_4$) δ: 8.44 (d, J=8.8 Hz, 1H), 7.95 (d, J=8.8 Hz, 1H), 7.51 (s, 1H), 7.42 (dd, J=8.5, 1.4 Hz, 1H), 7.26-7.16 (m, 5H), 7.05 (s, 1H), 6.97 (s, 1H), 6.86 (s, 1H), 5.17-5.14 (m, 1H), 3.12 (dd, J=13.8, 6.0 Hz, 1H), 3.04 (dd, J=13.8, 9.4 Hz, 1H), 2.76 (d, J=6.6 Hz, 2H), 2.22-2.17 (m, 1H), 1.84-1.78 (m, 3H), 1.66-1.63 (m, 1H), 1.57-1.54 (m, 1H), 1.44-1.33 (m, 2H), 1.07-1.00 (m, 2H). LCMS m/z $(M+H)^+$=484.5.

Example 8

4-Aminomethyl-cyclohexanecarboxylic acid {1-[5-(3-amino-1H-indazol-6-yl)-2-methoxy-phenyl]-2-phenyl-ethyl}-amide 8A. {4-[1-(5-Bromo-2-methoxy-phenyl)-2-phenyl-ethylcarbamoyl]-cyclohexylmethyl}-carbamic acid tert-butyl ester: The benzylamine was prepared following the procedure from 1A by replacing 3-phenylbenzaldehyde with 5-bromo-2-methoxybenzaldehyde. The benzylamine was coupled with the BOC-tranexamic acid according to the procedure from 2B to give the amide. $^1$H NMR (500 MHz, DMSO-$d_6$) δ: 8.14 (d, J=8.8 Hz, 1H), 7.42 (d, J=2.2 Hz, 1H), 7.37 (dd, J=8.8, 2.2 Hz, 1H), 7.25 (t, J=7.4 Hz, 2H), 7.18-7.15 (m, 3H), 6.94 (d, J=8.8 Hz, 1H), 6.77 (t, J=5.5 Hz, 1H), 5.30-5.26 (m, 1H), 3.80 (s, 3H), 2.87 (dd, J=13.8, 3.8 Hz, 1H), 2.73 (t, J=6.0 Hz, 2H), 2.67 (dd, J=13.8, 10.4 Hz, 1H), 2.03 (t, J=12.1 Hz, 1H), 1.67-1.61 (m, 3H), 1.49-1.47 (m, 1H), 1.35 (s, 9H), 1.22-1.08 (m, 3H), 0.85-0.76 (m, 2H).

LCMS m/z $(M+H)^+$=545 and $(M+2+H)^+$=547.4.

8B. 4-Aminomethyl-cyclohexanecarboxylic acid [1-(4'-cyano-3'-fluoro-4-methoxy-biphenyl-3-yl)-2-phenyl-ethyl]-amide: Compound 8A was converted to the TFA salt of the biphenyl cyclohexyl methyl amine derivative according to the procedure from 2C, where $Pd_2(dba)_3$, tri-tert-butylphosphonium tetrafluoroborate, $Cs_2CO_3$, and dioxane were replaced with $Pd(dppf)Cl_2.CH_2Cl_2$, $K_3PO_4$, and DMSO. LCMS m/z $(M+H)^+$=486.4.

8C. Example 8: Compound 8B was converted to Example 8 as the TFA salt following the procedure from 2D. $^1$H NMR (500 MHz, $MeOD_4$) δ: 8.31 (d, J=8.8 Hz, 1H), 7.94 (d, J=8.8 Hz, 1H), 7.60 (dd, J=8.5, 2.5 Hz, 1H), 7.54 (d, J=2.2 Hz, 1H), 7.50 (s, 1H), 7.44 (dd, J=8.8, 1.1 Hz, 1H), 7.25-7.20 (m, 4H), 7.18-7.15 (m, 1H), 7.11 (d, J=8.8 Hz, 1H), 5.53-5.50 (m, 1H), 3.94 (s, 3H), 3.17 (dd, J=13.8, 5.5 Hz, 1H), 2.93 (dd, J=13.8, 9.4 Hz, 1H), 2.75 (d, J=7.1 Hz, 2H), 2.22 (tt, J=12.0, 3.3 Hz, 1H), 1.83-1.76 (m, 3H), 1.67-1.65 (m, 1H), 1.57-1.53 (m, 1H), 1.45-1.30 (m, 2H), 1.07-0.99 (m, 2H). HRMS m/z calc'd. for $C_{30}H_{36}N_5O_2$ $(M+H)^+$=498.2869. Found 498.2848.

Example 9

4-Aminomethyl-cyclohexanecarboxylic acid {1-[5-(3-amino-1H-indazol-6-yl)-2-hydroxy-phenyl]-2-phenyl-ethyl}-amide To a cooled (0° C.) suspension of compound 8B (0.034 g, 0.070 mmol) in $CH_2Cl_2$ (1.4 mL) was added $BBr_3$ (0.066 mL, 0.70 mmol). Following the addition, the reaction was warmed to rt. After 1 h, the reaction was cooled to 0° C. and quenched with MeOH. The clear, yellow solution was concentrated to give the crude phenol as a yellow-brown residue. Indazole formation was accomplished following the procedure from 2D to give 0.0207 g (50%, off-white solid) of Example 9 as the TFA salt. $^1$H NMR (500 MHz, $MeOD_4$) δ: 8.25 (d, J=9.3 Hz, 1H), 7.91 (d, J=8.8 Hz, 1H), 7.45-7.42 (m, 3H), 7.41 (dd, J=8.8 Hz, 1H), 7.25-7.22 (m, 4H), 7.17-7.15 (m, 1H), 6.94 (d, J=7.7 Hz, 1H), 5.46-5.43 (m, 1H), 3.26 (dd, J=13.8, 5.5 Hz, 1H), 2.98 (dd, J=13.8, 9.4 Hz, 1H), 2.75 (d, J=7.1 Hz, 2H), 2.23-2.18 (m, 1H), 1.83-1.78 (m, 3H), 1.68-1.65 (m, 1H), 1.57-1.54 (m, 1H), 1.42-1.32 (m, 2H), 1.07-1.00 (m, 2H).

HRMS m/z calc'd. for $C_{29}H_{34}N_5O_2$ $(M+H)^+$=484.2713. Found 484.2714.

Example 10

4-Aminomethyl-cyclohexanecarboxylic acid {1-[3-(3-amino-1H-indazol-6-yl)-4-methoxy-phenyl]-2-phenyl-ethyl}-amide 10A. {4-[1-(3-Bromo-4-methoxy-phenyl)-2-phenyl-ethylcarbamoyl]-cyclohexylmethyl}-carbamic acid tert-butyl ester: The benzylamine was prepared following the procedure from 1A by replacing 3-phenylbenzaldehyde with 3-bromo-p-anisaldehyde. The benzylamine was coupled with the BOC-tranexamic acid according to the procedure from 2B to give the amide. $^1$H NMR (500 MHz, $CDCl_3$) δ: 7.39 (d, J=2.2 Hz, 1H), 7.23 (t, J=7.2 Hz, 2H), 7.18 (t, J=7.2 Hz, 1H), 7.07 (dd, J=8.2, 2.2 Hz, 1H), 7.04 (d, J=7.2 Hz, 2H), 6.78 (d, J=9.1 Hz, 1H), 5.83 (d, J=7.7 Hz, 1H), 5.16 (q, J=7.4 Hz, 1H), 4.60 (bs, 1H), 3.84 (s, 3H), 3.05 (dd, J=14.0, 6.8 Hz, 1H), 2.99 (dd, J=13.8, 7.7 Hz, 1H), 2.94-2.92 (m, 2H), 1.94 (tt, J=12.1, 3.3 Hz, 1H), 1.80-1.70 (m, 4H), 1.42 (s, 9H), 1.41-1.28 (m, 3H), 0.92-0.83 (m, 2H). LCMS m/z $(M-C_4H_9+H)^+$=489.3 and $(M+2-C_4H_9+H)^+$=491.3.

10B. {4-[1-(4'-Cyano-3'-fluoro-6-methoxy-biphenyl-3-yl)-2-phenyl-ethylcarbamoyl]-cyclohexylmethyl}-carbamic acid tert-butyl ester: Compound 10A was converted to the biphenyl derivative according to the procedure from 3B. The crude product was carried on to the next step without further purification.

10C. Example 10: Compound 10B was converted to Example 10 as the TFA salt following the procedure from 3C. $^1$H NMR (500 MHz, $MeOD_4$) δ: 8.41 (d, J=8.8 Hz, 1H), 7.88 (d, J=8.2 Hz, 1H), 7.43 (s, 1H), 7.36 (dd, J=8.8, 2.2 Hz, 1H), 7.29 (dd, J=8.8, 1.1 Hz, 1H), 7.25-7.22 (m, 3H), 7.19-7.16 (m, 3H), 7.08 (d, J=8.8 Hz, 1H), 5.16-5.12 (m, 1H), 3.80 (s, 3H), 3.10-3.02 (m, 2H), 2.75 (d, J=7.1 Hz, 2H), 2.19-2.14 (m, 1H), 1.83-1.75 (m, 3H), 1.66-1.64 (m, 1H), 1.57-1.53 (m, 1H), 1.43-1.33 (m, 2H), 1.06-0.99 (m, 2H). HRMS m/z calc'd. for $C_{30}H_{36}N_5O_2$ $(M+H)^+$=498.2869. Found 498.2855.

Example 11

4-Aminomethyl-cyclohexanecarboxylic acid {1-[3-(3-amino-1H-indazol-6-yl)-4-hydroxy-phenyl]-2-phenyl-ethyl}-amide To a cooled (0° C.) suspension of compound 10B (0.039 g, 0.066 mmol) in $CH_2Cl_2$ (0.70 mL) was added 1.0 M $BBr_3$ in dichloromethane (0.070 mL, 0.070 mmol). The resulting clear, yellow solution stirred at 0° C. Additional 1.0 M $BBr_3$ in dichloromethane (0.070 mL, 0.070 mmol) was added and the reaction warmed to rt. After 3 h, the reaction was cooled to 0° C. and neat $BBr_3$ (0.10 mL, 1.0 mmol) was added to give a brown suspension. After 30 min., 30% TFA in $CH_2Cl_2$ (2 mL) was added. After 30 min., the reaction was warmed to rt and concentrated. Purification by Prep HPLC [Phenomenex Luna 21.2×100 mm; 8 min. grad.; 30-100% B; 20 mL/min.; Solvent A: 90% H$_2$O, 10% methanol, 0.1% TFA; Solvent B: 10% H$_2$O, 90% methanol, 0.1% TFA] gave 0.0160 g (white solid) of the crude phenol as the TFA salt. Indazole formation was accomplished following the procedure from 2D to give 0.0129 g (32%, off-white solid) of Example 11 as the TFA salt. $^1$H NMR (500 MHz, MeOD$_4$) δ: 7.90 (d, J=8.8 Hz, 1H), 7.54 (s, 1H), 7.40 (dd, J=8.5, 1.4 Hz, 1H), 7.24-7.15 (m, 7H), 6.89 (dd, J=7.2, 2.2 Hz, 1H), 5.11 (t, J=7.7 Hz, 1H), 3.09-3.00 (m, 2H), 2.75 (d, J=7.2 Hz, 2H), 2.16 (tt, J=12.1, 3.6 Hz, 1H), 1.83-1.74 (m, 3H), 1.65-1.63 (m, 1H), 1.58-1.52 (m, 1H), 1.45-1.29 (m, 2H), 1.05-0.98 (m, 2H).

HRMS m/z calc'd. for C$_{29}$H$_{34}$N$_5$O$_2$ (M+H)$^+$=484.2713. Found 484.2701.

Example 12

4-Aminomethyl-cyclohexanecarboxylic acid {1-[3-(3-amino-1H-indazol-6-yl)-4-chloro-phenyl]-2-phenyl-ethyl}-amide 12A. 3-Bromo-4-chloro-benzaldehyde: To a cooled (0° C.), clear, colorless solution of 3-bromo-4-chlorobenzoic acid (1.0 g, 4.25 mmol) in THF (43 mL) was added dropwise a 1.0 M borane-THF complex (12.7 mL, 12.7 mmol). After 15 min, the reaction was warmed to rt and then to reflux. After 2 h, the reaction was cooled to rt, then to 0° C., and then quenched with MeOH (10 mL). The reaction was warmed to rt and after 15 min., the reaction was concentrated. The residue was dissolved in EtOAc and washed with 1.0 N HCl, sat. NaHCO$_3$, brine, dried over Na$_2$SO$_4$, filtered and concentrated to give a clear, colorless liquid. The liquid was dissolved in CH$_2$Cl$_2$ (17 mL) and cooled to 0° C. Next Dess-Martin periodinane (2.16 g, 5.10 mmol) was added. The resulting cloudy pale orange suspension was stirred for 30 min. and then diluted with Et$_2$O (50 mL). The reaction was filtered through a plug of silica gel and the filtrate was concentrated to give an off-white solid. Column chromatography on silica gel (gradient elution 0-25% EtOAc in Hex) gave 0.815 g (87%) of the aldehyde as a white solid. $^1$H NMR (400 MHz, CDCl$_3$) δ: 9.94 (s, 1H), 8.13 (d, J=1.8 Hz, 1H), 7.77 (dd, J=8.1, 2.0 Hz, 1H), 7.63 (d, J=7.9 Hz, 1H).

12B. Example 12: The benzylamine was prepared following the procedure from 1A by replacing 3-phenylbenzaldehyde with the aldehyde from 12A. The benzylamine was coupled with the BOC-tranexamic acid according to the procedure from 2B to give the amide. The amide derivative was converted to the TFA salt of the biphenyl cyclohexyl methyl amine derivative according to the procedure from 2C, where Pd$_2$(dba)$_3$, tri-tert-butylphosphonium tetrafluoroborate, Cs$_2$CO$_3$, and dioxane were replaced with Pd(dppf)Cl$_2$·CH$_2$Cl$_2$, K$_3$PO$_4$, and DMSO. The biphenyl cyclohexyl methyl amine derivative was converted to Example 12 as the TFA salt according to the procedure from 2D. $^1$H NMR (400 MHz, MeOD$_4$) δ: 8.48 (d, J=8.4 Hz, 1H), 7.95 (d, J=8.8 Hz, 1H), 7.48 (d, J=7.9 Hz, 1H), 7.37 (dd, J=8.3, 2.2 Hz, 1H), 7.35 (s, 1H), 7.26-7.23 (m, 3H), 7.20-7.16 (m, 4H), 5.19-5.14 (m, 1H), 3.07 (d, J=7.9 Hz, 2H), 2.76 (d, J=7.0 Hz, 2H), 2.19 (tt, J=12.1, 3.5 Hz, 1H), 1.85-1.75 (m, 3H), 1.68-1.64 (m, 1H), 1.60-1.52 (m, 1H), 1.46-1.29 (m, 2H), 1.07-0.98 (m, 2H). HRMS m/z calc'd. for C$_{29}$H$_{33}$N$_5$OCl (M+H)$^+$=502.2374. Found 502.2391.

Example 13

4-Aminomethyl-cyclohexanecarboxylic acid {(S)-1-[3-(3-amino-1H-indazol-6-yl)-phenyl]-2-phenyl-ethyl}-amide 13A. {4-[(S)-1-(3-Bromo-phenyl)-2-phenyl-ethylcarbamoyl]-cyclohexylmethyl}-carbamic acid tert-butyl ester. Enantiomer B of benzylamine from 2A was coupled with the BOC-tranexamic acid according to the procedure from 2B to give the amide. [α]$_D^{25}$=−12.66 (c=0.89; CHCl$_3$)

13B. Example 13: To a flame-dried sealed tube apparatus was placed compound 13A (0.344 g, 0.667 mmol), Pd(dppf)Cl$_2$·CH$_2$Cl$_2$ (0.0545 g, 0.0667 mmol), K$_3$PO$_4$ (0.283 g, 1.33 mmol), and 3-fluoro-4-cyanophenyl boronic acid (0.220 g, 1.33 mmol). The tube was purged with argon for several minutes and then degassed DMSO (4.4 mL) was added, the tube was sealed with a Teflon screw cap and the vial was placed in a preheated oil bath (90° C.). After 14.5 h, the reaction was stopped and cooled to rt. The reaction was diluted with CH$_2$Cl$_2$ (300 mL), washed with water, brine, dried over MgSO$_4$, filtered, and concentrated to give a red-brown solid weighing 0.671 g.

Boc-deprotection: The solid was dissolved in 30% TFA in CH$_2$Cl$_2$ (30 mL). After 1h, the reaction was concentrated. Purification by Prep HPLC [Phenomenex Luna 30×250 mm; 30 min. grad.; 30-100% B; 30 mL/min.; Solvent A: 90% H$_2$O, 10% methanol, 0.1% TFA; Solvent B: 10% H$_2$O, 90% methanol, 0.1% TFA] gave an off-white solid weighing 0.117 g.

Indazole formation: A suspension of the solid in n-butanol (3.0 mL) and hydrazine monohydrate (1.0 mL) was microwaved in a Personal Chemistry Emrys™ Optimizer microwave at 150° C. for 10 min. The resulting clear, biphasic solution was concentrated. Purification by Prep HPLC [Phenomenex Luna 21.2×100 mm; 8 min. grad.; 20-100% B; 20 mL/min.; Solvent A: 90% H$_2$O, 10% methanol, 0.1% TFA; Solvent B: 10% H$_2$O, 90% methanol, 0.1% TFA] gave 0.0725 g (19%, off-white solid) of Example 13 as the TFA salt. $^1$H NMR (500 MHz, MeOD$_4$) δ: 8.51 (d, J=8.25 Hz, 1H), 7.96 (d, J=8.8 Hz, 1H), 7.57-7.54 (m, 3H), 7.47-7.41 (m, 3H), 7.26-7.16 (m, 5H), 5.26-5.21 (m, 1H), 3.13 (dd, J=14.0, 6.9 Hz, 1H), 3.08 (dd, J=14.0, 9.1 Hz, 1H), 2.76 (d, J=7.1 Hz, 2H), 2.20 (tt, J=12.0, 3.3 Hz, 1H), 1.84-1.76 (m, 3H), 1.68-1.65 (m, 1H), 1.59-1.53 (m, 1H), 1.45-1.31 (m, 2H), 1.07-0.99 (m, 2H).

HRMS m/z calc'd. for C$_{29}$H$_{34}$N$_5$O (M+H)$^+$=468.2763. Found 468.2754. [α]$_D^{237}$=+7.68 (c=0.8; MeOH)

Example 14

4-Aminomethyl-cyclohexanecarboxylic acid {(R)-1-[3-(3-amino-1H-indazol-6-yl)-phenyl]-2-phenyl-ethyl}-amide 14A. {4-[(R)-1-(3-Bromo-phenyl)-2-phenyl-ethylcarbamoyl]-cyclohexylmethyl}-carbamic acid tert-butyl ester: Enantiomer A of benzylamine from 2A was coupled with the BOC-tranexamic acid according to the procedure from 2B to give the amide. [α]$_D^{25}$=+13.13 (c=0.78; CHCl$_3$).

14B. Example 14: The title compound was prepared as the TFA salt following the procedures from 13B by replacing compound 13A with the compound from Example 14, Part A Example 15

4-Aminomethyl-cyclohexanecarboxylic acid {[3-(3-amino-1H-indazol-6-yl)-phenyl]-[(pyridin-2-ylmethyl)-carbamoyl]-methyl}-amide 15A. (3-Bromo-phenyl)-tert-butoxycarbonylamino-acetic acid: α-Amino-3-Bromobenzeneacetic acid (1.35g, 5.9 mmol), Et$_3$N (3.42 g, 4.71 mL, 33.8 mmol), water (20 mL) and dioxane (20 mL) were stirred at ambient temperature. A solution of di-tert-butyl dicarbonate (1.84 g, 8.44 mmol) in dioxane (5 mL) was added in one portion. A mild exotherm ensued. Stirring was continued for 39 h. Solvent was removed in vacuo to afford a yellow oil. The oil was dissolved in EtOAc (100 mL) and the solution was washed three times with a 0.01 N HCl solution (10 mL). Drying over MgSO$_4$, filtration and removal of solvent in vacuo provided 1.72 g (88%, yellow oil) of the acid, which was used without further purification. $^1$H NMR (CDCl$_3$, 400 MHz): 7.55 (s, 1H), 7.37 (t, 2H, J=8), 7.17 (t, 1H, J=8), 5.13 (d, 1H, J=7), 2.9 (m, 2H), 1.42 (s, 9H). LCMS m/z (M−H)$^-$=328 and (M+2−H)$^-$=330.

15B. {(3-Bromo-phenyl)-[(pyridin-2-ylmethyl)-carbamoyl]-methyl}-carbamic acid tert-butyl ester: Compound 15A (1.72 g, 5.23 mmol), HOBt (0.76 g, 5.64 mmol), EDC (1.08 g, 5.64 mmol) and DMF (10 mL) were stirred at rt. Hunig's base (3.64 g, 4.91 mL, 28.2 mmol) was added in one portion and stirring was continued for 15 min. A solution of 2-aminomethyl pyridine (0.61 g, 5.64 mmol) in DMF (10 mL) was added dropwise. Stirring was continued for 27 h. The reaction mixture was diluted with EtOAc (200 mL) and the resulting solution was washed three times with a 10% LiCl solution (35 mL) and three times with a saturated Na$_2$CO$_3$ solution (30 mL). Drying over MgSO$_4$, filtration and removal of solvent in vacuo gave 0.600 g (27%, yellow oil) of the amide. $^1$H NMR (CDCl$_3$, 400 MHz): 8.51 (d, 1H, J=4), 7.64 (t, 1H, J=8), 7.56 (s, 1H), 7.44 (d, 1H, J=8), 7.23 (m, 4H), 7.06 (s, 1H), 5.86 (s, 1H), 5.21 (s, 1H), 4.59 (dd, 1H, J=17, 5), 4.51 (d, 1H, J=17, 5), 1.42 (s, 9H). LCMS m/z (M+H)$^+$=420 and (M+2+H)$^+$=422.

15C. 2-Amino-2-(3-bromo-phenyl)-N-pyridin-2-ylmethyl-acetamide: Compound 15B (600 mg, 1.43 mmol), trifluoroacetic acid (2 mL) and DCM (2 mL) were stirred at rt for 22.5 h. Solvent was removed in vacuo to provide a brown oil. The oil was treated with a saturated Na$_2$CO$_3$ solution (20 mL) and extracted with EtOAc three times (20 mL). The combined organic layers were dried over MgSO$_4$ and filtered. The filtrate was concentrated in vacuo to provide 0.460 g (100%, pale yellow oil) of the amine. $^1$H NMR (CDCl$_3$, 400 MHz): 8.56 (d, 1H, J=5), 8.1 (s, 1H), 7.63 (m, 2H), 7.42 (d, 1H, J=8), 7.38 (d, 1H, J=8), 7.20 (m, 2H), 4.58 (s, 2H), 1.78 (s, 4H). LCMS m/z (M+H)$^+$=320 and (M+2+H)$^+$=322.

15D. [4-({(3-Bromo-phenyl)-[(pyridin-2-ylmethyl)-carbamoyl]-methyl}-carbamoyl)-cyclohexylmethyl]-carbamic acid tert-butyl ester: Compound 15C (460 mg, 1.43 mmol), N-Boc-tranexamic acid (420 mg, 1.62 mmol), HOBt (240 mg, 1.78 mmol), EDC (340 mg, 1.78 mmol), Hunig's base (950 mg, 1.28 mL, 7.36 mmol) and DMF (4 mL) were stirred at ambient temperature for 19.5 h. The reaction mixture was diluted with EtOAc (100 mL) and the resulting solution was washed three times with a 10% LiCl solution (20 mL). The organic layer was dried over MgSO$_4$ and filtered. Solvent was removed in vacuo to provide a dark tan solid. Trituration with copious amounts of ether. Filtration and drying in vacuo afforded 0.322 g (40%, off-white powder) of the amide. $^1$H NMR (CDCl$_3$, 400 MHz): 8.88 (t, 1H, J=6), 8.47 (dd, 2H, J=8, 5), 7.68 (m, 2H), 7.48 (dd, 1H, J=8), 7.42 (d, 1H, J=8), 7.30 (t, 1H, J=8), 7.26 (dd, 1H, J=8, 5), 7.11 (d, 1H, J=8), 6.79 (m, 1H), 5.51 (d, 1H, J=8), 4.34 (d, 2H, J=6), 2.74 (t, 2H, J=6), 2.27 (m, 1H), 1.68 (m, 4H), 1.35 (s, 9H), 1.24 (m, 3H), 0.82 (m, 2H). LCMS m/z (M+H)$^+$=559 and (M+2+H)$^+$=561.

15E. [4-({(4'-Cyano-3'-fluoro-biphenyl-3-yl)-[(pyridin-2-ylmethyl)-carbamoyl]-methyl}-carbamoyl)-cyclohexylmethyl]-carbamic acid tert-butyl ester: Compound 15D (322 mg, 0.58 mmol), 3-fluoro-4-cyanobenzeneboronic acid (96 mg, 0.58 mmol), Na$_2$CO$_3$ (307 mg, 2.9 mmol), Pd(PPh$_3$)$_4$ (69 mg, 0.06 mmol), water (2 mL) and DME (2 mL) were stirred at rt. The reaction was subjected to mild vacuum and a nitrogen atmosphere was then introduced. The process was repeated twice. The reaction mixture was heated to 80° C. and stirred for 15 h. After being cooled to rt, the reaction mixture was partitioned between EtOAc (10 mL) and water (10 mL). The layers were separated and the organic layer was extracted with EtOAc three times. The combined organic layers were dried over MgSO$_4$ and filtered. Solvent was removed in vacuo to give a tan solid. Recrystallization from acetone, filtration, and drying in vacuo provided 0.067 g (19%, tan solid) of the biphenyl derivative. $^1$H NMR (DMSO-d$_6$, 400 MHz): 8.87 (t, 1H, J=6), 8.47 (m, 2H), 8.07 (t, 1H, J=7), 7.90 (s, 1H), 7.86 (d, 1H, J=11), 7.74 (m, 2H), 7.65 (m, 1H), 7.51 (m, 2H), 7.23 (t, 1H, J=6), 7.11 (d, 1H, J=9), 6.79 (m, 1H), 5.62 (d, 1H, J=6), 4.37 (d, 2H, J=6), 2.77 (t, 2H, J=7), 2.31 (m, 1H), 1.73 (m, 4H), 1.37 (s, 9H), 1.3 (m, 4H), 0.86 (m, 2H). HRMS m/z calc'd for C$_{34}$H$_{39}$FN$_5$O$_4$ (M+H)$^+$: 600.2986. Found: 600.2983.

15F. 4-Aminomethyl-cyclohexanecarboxylic acid {(4'-cyano-3'-fluoro-biphenyl-3-yl)-[(pyridin-2-ylmethyl)-carbamoyl]-methyl}-amide: Compound 15E (30 mg, 0.05 mmol), trifluoracetic acid (0.3 mL) and DCM (0.7 mL) were stirred at rt for 15 h. Solvent was removed in vacuo to provide 0.080 g (100%, brown oil) of the amine as the bis-TFA salt. $^1$H NMR (DMSO-d$_6$, 400 MHz): 8.92 (t, 1H, J=6), 8.50 (m, 2H), 8.07 (t, 1H, J=7), 7.89 (d, 1H, J=10), 7.85 (dd, 1H, J=11, 2), 7.75 (m, 2H), 7.74 (m, 2H), 7.70 (s, 1H), 7.33 (m, 1H), 7.18 (d, 1H, J=8), 5.61 (d, 1H, J=8), 4.40 (d, 2H, J=6), 2.67 (m, 2H), 2.55 (m, 3H), 2.35 (m, 1H), 1.79 (m, 4H), 1.35 (M, 2H), 0.95 (m, 2H). HRMS calc'd for C$_{29}$H$_{31}$FN$_5$O$_2$ (M+H)$^+$: 500.2462. Found: 500.2450.

15G. Example 15: Compound 15F (80 mg, 0.11 mmol), hydrazine hydrate (0.8 mL) and n-butanol (2 mL) were subjected to microwave irradiation in a sealed tube at 150° C. for 10 min. After being cooled to rt, the layers were separated. The organic layer was concentrated in vacuo to give a pale yellow viscous oil. Trituration with ether, filtration and drying in vacuo provided 0.075 g (93%, pale yellow solid) of Example 15 as the bis-TFA salt. $^1$H NMR (DMSO-d$_6$, 400 MHz): 8.89 (t, 1H, J=7), 8.53 (d, 1H, J=8), 8.45 (d, 1H, J=4), 7.77 (m, 2H), 7.43 (m, 4H), 7.16 (m, 5H), 5.58 (d, 1H, J=8), 5.39 (s, 2H), 4.36 (m, 3H), 3.37 (m, 3H), 2.65 (d, 2H, J=6), 1.75 (m, 4H), 1.37 (m, 4H). HRMS calc'd for C$_{29}$H$_{34}$N$_7$O$_2$ (M+H)$^+$: 512.2774. Found: 512.2788.

Example 16

4-Aminomethyl-cyclohexanecarboxylic acid {1-[3-(3-amino-1H-indazol-6-yl)-2-hydroxy-phenyl]-2-phenyl-ethyl}-amide 16A. 3-Bromo-2-methoxy-benzaldehyde: (WO 2004/050637 and Duffy, K. J. et al., *J. Med. Chem.*, 2002, 45(17), 3573) To a clear, colorless solution of 2-bromophenol (2.0 g, 11.56 mmol) in CH$_3$CN (25.7 mL) was added anhydrous MgCl$_2$ (4.40 g, 46.2 mmol) followed by Et$_3$N (12.1 mL, 86.7 mmol). After 5 min., paraformaldehyde (2.77 g, 92.5 mmol) was added and the reaction was heated to a gentle reflux. After 1.5 h, the yellow suspension was cooled to rt and poured into a mixture of Et$_2$O (400 mL)/5% citric acid (500 mL). Manual stirring gave two layers. The layers were separated and the organic layer was washed with water, brine, dried over Na$_2$SO$_4$, filtered and concentrated to give 2.12 g of a clear, orange-yellow liquid which solidified upon standing.

To a solution of the above solid in DMF (58 mL) was added MeI (0.86 mL, 13.9 mmol) and K$_2$CO$_3$ (4.80 g, 34.7 mmol). After 18 h, the reaction was filtered, the filtrate was poured into water (250 mL), and compound 16A was extracted with CH$_2$Cl$_2$. The organic layer was washed with brine, dried over MgSO$_4$, and concentrated to give a clear, light-brown liquid. Column chromatography on silica gel (gradient elution 0-20% EtOAc/Hex) gave 1.58 g (64%) of the aldehyde as a clear, colorless liquid. $^1$H NMR (500 MHz, CDCl$_3$) δ: 10.35 (d, J=1.0 Hz, 1H), 7.80 (dd, J=7.7, 1.6 Hz, 1H), 7.79 (dd, J=7.7, 1.6 Hz, 1H), 7.13 (t, J=7.7 Hz, 1H), 3.98 (s, 3H).

16B. 4-Aminomethyl-cyclohexanecarboxylic acid [1-(4'-cyano-3'-fluoro-2-methoxy-biphenyl-3-yl)-2-phenyl-ethyl]-amide: The benzylamine was prepared following the procedure from 1A by replacing 3-phenylbenzaldehyde with the aldehyde from 16A. The benzylamine was coupled with the BOC-tranexamic acid according to the procedure from 2B to give the amide. The amide derivative was converted to the TFA salt of the biphenyl cyclohexyl methyl amine derivative according to the procedure from 2C, where Pd$_2$(dba)$_3$, tri-tert-butylphosphonium tetrafluoroborate, Cs$_2$CO$_3$, and dioxane were replaced with Pd(dppf)Cl$_2$.CH$_2$Cl$_2$, K$_3$PO$_4$, and DMSO. $^1$H NMR (500 MHz, MeOD$_4$) δ: 8.40 (d, J=8.2 Hz, 1H), 7.80 (t, J=7.4 Hz, 1H), 7.55 (d, J=8.8 Hz, 2H), 7.48 (dd, J=7.7, 1.6 Hz, 1H), 7.31 (dd, J=7.7, 1.6 Hz, 1H), 7.27-7.16 (m, 6H), 5.62-5.57 (m, 1H), 3.38 (s, 3H), 3.09 (dd, J=13.7, 5.5 Hz, 1H), 2.96 (dd, J=13.7, 9.9 Hz, 1H), 2.76 (d, J=7.2 Hz, 2H), 2.22-2.17 (m, 1H), 1.85-1.76 (m, 4H), 1.68-1.65 (m, 1H), 1.58-1.53 (m, 1H), 1.44-1.31 (m, 2H), 1.08-1.00 (m, 2H). HRMS calc'd for C$_{30}$H$_{33}$N$_3$O$_2$F (M+H)$^+$: 486.2557. Found: 486.2545.

16C. Example 16: The title compound was prepared as the TFA salt according to the procedures for Example 9 by replacing the compound from 8B with compound 16B. $^1$H NMR (500 MHz, MeOD$_4$) δ: 7.96 (d, J=8.8 Hz, 1H), 7.55 (s, 1H), 7.41 (dd, J=8.8, 1.6 Hz, 1H), 7.37 (dd, J=7.6, 1.6 Hz, 1H), 7.30-7.23 (m, 5H), 7.19 (t, J=7.1 Hz, 1H), 7.00 (t, J=7.7 Hz, 1H), 5.48 (dd, J=10.4, 4.9 Hz, 1H), 3.25 (dd, J=13.8, 4.9 Hz, 1H), 3.10 (dd, J=13.8, 10.4 Hz, 1H), 2.75 (d, J=6.5 Hz, 2H), 2.18-2.14 (m, 1H), 1.83-1.74 (m, 3H), 1.59-1.52 (m, 2H), 1.39 (dq, J=12.6, 3.3 Hz, 1H), 1.28 (dq, J=12.6, 3.3 Hz, 1H), 1.05-0.98 (m, 2H). HRMS calc'd for C$_{29}$H$_{34}$N$_5$O$_2$ (M+H)$^+$: 484.2713. Found: 494.2733.

Example 17

4-Aminomethyl-cyclohexanecarboxylic acid {(S)-1-[3-(3-amino-1,2-benzisoxazol-6-yl)-phenyl]-2-phenyl-ethyl}-amide To a clear solution of acetohydroxamic acid (0.0133 g, 0.18 mmol) in DMF (0.5 mL) was added tBuOK (0.020 g, 0.18 mmol). The resulting white suspension was stirred for 30 min., and then a solution of the compound from the Boc-deproctection step in 13B (0.0180 g, 0.032 mmol) in DMF (0.5 mL) was added. After 24 h, the reaction was quenched with water and then brine was added. The reaction was extracted with ethyl acetate (3×). The combined organic layers were washed with brine, dried over Na$_2$SO$_4$, filtered and concentrated. Purification by Prep HPLC [Phenomenex Luna 21.2×100 mm; 8 min. grad.; 30-100% B; 20 mL/min.; Solvent A: 90% H$_2$O, 10% methanol, 0.1% TFA; Solvent B: 10% H$_2$O, 90% methanol, 0.1% TFA] gave 0.0025 g (13%, white solid) of Example 17 as the TFA salt. $^1$H NMR (400 MHz, MeOD$_4$) δ: 8.45 (d, J=8.8 Hz, 1H), 7.80 (d, J=8.4 Hz, 1 H), 7.58-7.53 (m, 3H), 7.48 (dd, J=8.4, 1.3 Hz, 1H), 7.43 (t, J=7.5 Hz, 1H), 7.38-7.36 (m, 3H), 7.26-7.18 (m, 5H), 5.27-5.21 (m, 1H), 3.14 (dd, J=13.6, 6.4 Hz, 3.06 (dd, J=13.6, 9.2 Hz, 1H), 2.75 (d, J=7.0 Hz, 2H), 2.22-2.16 (m, 1H), 1.84-1.77 (m, 3H), 1.67-1.64 (m, 1H), 1.56-1.52 (m, 1H), 1.43-1.33 (m, 2H), 1.07-1.01 (m, 2H), LCMS m/z (M+H)$^+$=469.3.

Example 24

(3'-{1-[(4-Aminomethyl-cyclohexanecarbonyl)-amino]-2-phenyl-ethyl}-biphenyl-4-yl)-carbamic acid methyl ester To compound 2B (50 mg, 0.097 mmol) in a 20 mL screw-cap vial in Ar degassed 4:1 DME/H$_2$O (2 mL) were added K$_2$CO$_3$ (53 mg, 0.38 mmol), (4-methoxycarbonylaminophenyl) boronic acid (24 mg, 0.123 mmol), and Pd(Ph$_3$P)$_4$ (11 mg, 0.0096 mmol). The vial was sealed and heated to 60° C. for 48 h. The solvents were concentrated and the residue suspended in Et$_2$O and filtered to remove triphenylphosphine oxide. The solid residue collected was treated with 25% TFA/CH$_2$Cl$_2$ (10 ml) for 1 h, then concentrated. The crude product was taken up in CH$_3$CN/H$_2$O, filtered and purified by reverse phase HPLC (CH$_3$CN:H$_2$O:TFA) and freeze-dried to afford 27 mg (46.5%, white solid) of Example 24 as the TFA salt. $^1$H NMR (MeOD 400) δ 7.50 (5H, s), 7.47-7.45 (1H, d, J=7.58 Hz), 7.38 (1H, t, J=7.59 Hz), 7.27-7.15 (6H, m), 5.22 (1H, m), 3.75 (3H, s), 3.15-3.02 (2H, m), 2.76 (2H, d, J=7 Hz), 2.21-2.15 (1H, m), 1.84-1.76 (3H, m), 1.68 (1H, d, J=13.69 Hz), 1.56-1.54 (1H, m), 1.43-1.37 (2H, m), 1.07-1.01 (2H, m). HRMS m/z calc'd for C$_{23}$H$_{36}$N$_3$O$_3$ 486.2757. Found 486.2762.

Example 41

4-Aminomethyl-cyclohexanecarboxylic acid {2-phenyl-1-[3'-(1H-tetrazol-5-yl)-biphenyl-3-yl]-ethyl}-amide 41A. {4-[1-(3'-Cyano-biphenyl-3-yl)-2-phenyl-ethylcarbamoyl]-cyclohexylmethyl}-carbamic acid tert-butyl ester: Compound 2B was converted to 41A according to the procedure described in Example 24, by replacing 4-(methoxy-carbonylamino) phenyl boronic acid with 3-cyanophenyl boronic acid. LC/MS m/z (M+H—C$_4$H$_8$)$^+$482.4.

41B. Example 41: Compound 41A (60 mg, 0.111 mmol) was heated with NaN$_3$ (18 mg, 0.27 mmol) in DMF (2 mL) at 85° C. for 72 h. The reaction was cooled, partioned with EtOAc/H$_2$O separated and extracted with EtOAc, washed with brine and dried (MgSO$_4$). The crude product was treated with 25% TFA in CH$_2$Cl$_2$ (15 ml) for 3 h. The reaction was concentrated and purified by reverse phase HPLC (MeOH/H$_2$O/TFA) and desired fractions were concentrated to afford 52 mg (78%, white solid) of Example 41 as the TFA salt. $^1$H NMR (MeOD 400) δ 8.0-7.82 (2H, m), 7.68-7.6 (4H, m), 7.5-7.38 (2H, m), 7.24-7.15 (5H, m), 5.27-5.21 (m, 1H), 3.11-3.0 (2H, m), 2.77-2.75 (2H, d, J=7.1 Hz), 2.24-2.18 (1H, m), 1.85-1.81 (3H, m), 1.67-1.65 (1H, d, J=12.3 Hz), 1.54 (1H, brds), 1.41-1.35 (2H, m), 1.07-0.99 (2H, m).

HRMS m/z calc'd for C$_{29}$H$_{32}$N$_6$O 481.2707. Found 481.2707.

Example 62

4-Amino-3'-{1-[(4-aminomethyl-cyclohexanecarbonyl)-amino]-2-phenyl-ethyl}-biphenyl-3-carboxylic acid 62A. 4-Amino-3'-(1-{[4-(tert-butoxycarbonylamino-methyl)-cyclohexanecar-bonyl]-amino}-2-phenyl-ethyl)-biphenyl-3-carboxylic acid methyl ester: Compound 2B was converted to compound 62A according to the procedure described in Example 24, by replacing 4-(methoxy-carbonylamino) phenyl boronic acid with 2-amino-5-(5,5-dimethyl-[1,3,2]dioxaborinan-2-yl)-benzoic acid methyl ester. LC/MS m/z (M+H-tBoc)+486.41.

62B. Example 62: Compound 62A and excess LiOH was stirred for 18 h. The reaction was concentrated, acidified with TFA and purified by reverse phase HPLC (CH$_3$CN/H$_2$O/TFA) to afford 2.87 mg (5%) of Example 62 as the bis-TFA salt. $^1$H NMR (MeOD 400) δ 8.07 (1H, s), 7.52-7.50 (1H, dd, J=8.6,2.2 Hz), 7.46 (1H, s), 7.43-7.41 (1H, d, J=8.6 Hz), 7.34-7.32 (1H, t, J=7.6 Hz), 7.24-7.14 (6H, m), 6.83-6.81 (1H, d, J=8.6 Hz), 5.22-5.18 (1H, m), 3.11-3.0 (2H, m), 2.76-2.75 (2H, d, J=6.8 Hz), 2.19 (1H, m), 1.86-1.81 (3H, m), 1.67-1.64 (1H, m), 1.54 (1H, m), 1.41-1.35 (2H, m), 1.07-0.98 (2H, m). HRMS m/z calc'd for C$_{29}$H$_{34}$N$_3$O$_3$ 472.2600. Found 472.2596.

Example 66

4-Aminomethyl-cyclohexanecarboxylic acid {1-[3-(6-amino-pyridin-3-yl)-phenyl]-2-phenyl-ethyl}-amide 66A. (4-{1-[3-(6-Amino-pyridin-3-yl)-phenyl]-2-phenyl-ethylcarbamoyl}-cyclohexylmethyl)-carbamic acid tert-butyl ester: Compound 2B was converted to compound 66A according to the procedure described in Example 24, by replacing 4-(methoxy-carbonylamino) phenyl boronic acid with 5-(4,4,5,5-Tetramethyl-[1,3,2]dioxaborolan-2-yl)-pyridin-2-ylamine. LC/MS m/z (M+H)+=529.4.

Example 66. To compound 66A (30 mg, 0.056 mmol) was added 30% TFA/CH$_2$Cl$_2$ (2 mL) and the reaction was stirred 30 min. The reaction was concentrated, dissolved in CH$_3$CN and filtered. Purification by reverse phase HPLC and freeze-drying afforded 8 mg (26%) of Example 66 as the bis-TFA salt. $^1$H NMR (MeOD 400) δ 8.13-8.10 (1H, dd, J=9.2,2.2 Hz), 7.95 (1H, s), 7.40-7.34 (4H, m), 7.17-7.10 (5H, m), 7.03-7.01 (1H, d, J=9.23 Hz), 5.15-5.09 (1H, m), 3.04-2.97 (2H, m), 2.69-2.67 (2H, d, J=7.03 Hz), 2.11-2.10 (1H, m), 1.76-1.73 (2H, d, J=11.43 Hz), 1.72-1.70 (1H, d, J=13.19 Hz), 1.69-1.66 (1H, d, J=12.3 Hz), 1.48-1.46 (1H, m), 1.33-1.20 (2H, m), 1.00-0.93 (2H, m). HRMS m/z calc'd for C$_{27}$H$_{33}$N$_4$O 429.2654. Found 429.2645.

Example 67

[5-(3-{1-[(4-Aminomethyl-cyclohexanecarbonyl)-amino]-2-phenyl-ethyl}-phenyl)-pyridin-2-yl]-carbamic acid methyl ester To compound 66A (90 mg, 0.13 mmol) in a separatory funnel in CH$_2$Cl$_2$ (50 mL) and 1N NaOH (10 mL) was added methyl chloroformate (0.5 mL, 5.3 mmol). The funnel was shaken for 10 min and the layers were separated. The CH$_2$Cl$_2$ layer was washed with water and brine and then concentrated. The residue was treated with 30% TFA/CH$_2$Cl$_2$ (10 mL) for 30 min and concentrated to give the bis-carbamate. Hydrolysis was performed with EtOH (10 mL) with 1N NaOH (5 mL) for 18 h. The solvents were removed and the residue acidified with TFA and dissolved in CH$_3$CN/H$_2$O and filtered. Purification by reverse phase HPLC (CH$_3$CN/H$_2$O/TFA) and freeze-drying afforded 18 mg (19%) of Example 67 as the bis-TFA salt. $^1$H NMR (MeOD 400) δ 8.49 (1H, s), 8.47-8.45 (1H, m), 8.22-8.20 (1H, dd, J=2.2,9.2 Hz), 7.78-7.75 (1H, d, J=9.2 Hz), 7.51-7.45 (4H, m), 725-7.10 (4H, m), 5.25-5.15 (m, 1H), 3.85 (3H, s), 3.18-3.0 (2H, m), 2.69-2.67 (2H, d, J=7.03 Hz), 2.11-2.10 (1H, m), 1.76-1.73 (2H, d, J=11.43 Hz), 1.72-1.70 (1H, d, J=13.19 Hz), 1.69-1.66 (1H, d, J=12.3 Hz), 1.48-1.46 (1H, m), 1.33-1.20 (2H, m), 1.00-0.93 (2H, m). HRMS m/z calc'd for C$_{29}$H$_{35}$N$_4$O$_3$ 487.2709. Found 487.2704.

Example 72

4-Aminomethyl-cyclohexanecarboxylic acid {1-[3-(2-amino-thiazol-4-yl)-phenyl]-2-phenyl-ethyl}-amide 72A. {4-[1-(3-Acetyl-phenyl)-2-phenyl-ethylcarbamoyl]-cyclohexylmethyl}-carbamic acid tert-butyl ester: To compound 2B (0.47 g, 0.91 mmol) in dioxane (8 mL) was added tributyl(1-ethoxyvinyl)tin (0.46 mL, 1.36 mmol) and (Ph$_3$P)$_2$PdCl$_2$ (15 mg) and the reaction was heated to 100° C. for 2 h. The reaction was cooled and partioned with EtOAc/1N HCl. The EtOAc layers were washed with sat'd NaHCO$_3$, brine and dried (MgSO$_4$). Purification by silica gel chromatography (hexanes/ethyl acetate) afforded 0.28 g (67%) of compound 72A as a dark solid.

LC/MS m/z (M+H-tBoc)+379.37 and (M+Na)+501.39.

B. Example 72: Compound 72A (0.2 g, 0.417 mmol) was treated with bromine (70 mg, 0.44 mmol) in CHCl$_3$(10 mL) open to air 18 h. TLC indicated starting material was still present. An additional drop of bromine stirred 1 h had no effect. The reaction was concentrated. To the crude bromide was added EtOH (5 mL), thiourea (50 mg, 0.65 mmol) and pyridine (0.05 mL). The reaction was heated to reflux 2 h. The reaction was concentrated and residue taken up in CH$_2$Cl$_2$ (w/1 mL MeOH), washed with H$_2$O, brine and dried (MgSO$_4$). The MgSO$_4$ cake was washed with EtOAc/MeOH to recover product. LC/MS indicated the Boc protecting group had been removed in the reaction. The material was purified by HPLC (CH$_3$CN/H$_2$O/TFA, 2x) to afford 18 mg (7.8%, white solid) of Example 72 as the bis-TFA salt. $^1$H NMR (MeOD 400) δ 8.35-8.33 (1H, d, J=8.06 Hz), 7.62 (1H, s), 7.57-7.56 (1H, d, J=8.8 Hz), 7.43-7.41 (2H, m), 7.25-7.17 (5H, m), 6.95 (1H, s), 5.24-5.20 (1H, m), 3.13-3.0 (2H, m), 2.76-2.75 (2H, d, J=6.6 Hz), 2.20-2.16 (1H, m), 1.84-1.81 (2H, d, J=10.7Hz), 1.77-1.74 (1H, d, J=13.21 Hz), 1.66-1.63 (1H, d, J=13.94 Hz), 1.58 (1H, m), 1.42-1.35 (2H, m), 1.07-1.01 (2H, m). HRMS m/z calc'd for C$_{25}$H$_{31}$N$_4$OS 435.2219. Found 435.2225.

Example 75

4-Aminomethyl-cyclohexanecarboxylic acid {(S)-1-[3-(3-hydroxy-1H-indazol-5-yl)-phenyl]-2-phenyl-ethyl}-amide Compound 2B was reacted with 3-carboxy-4-fluorophenylboronic acid according to the procedure described in Example 24. The reaction was concentrated and the crude material was taken up in n-butanol (2 ml) with hydrazine hydrate (0.25 ml) and heated in a microwave 2 h at 150° C. The reaction was concentrated and the residue treated with 30% TFA/CH$_2$Cl$_2$ for 24 h. Purification by HPLC (CH$_3$CN/H$_2$O/TFA) and freeze-drying afforded 8 mg (14%, white solid) of Example 75 as the TFA salt. $^1$H NMR (MeOD 400) δ 7.84 (1H,s), 7.65-7.63 (1H, d, J=8.84 Hz), 7.48 (1H, s), 7.43-7.41 (1H, d, J=7.83 Hz), 7.31-7.30 (1H, d, J=7.6 Hz), 7.28-7.25 (1H, d, J=8.6 Hz), 7.2-7.18 (1H, d, J=7.6 Hz), 7.15-7.07 (5H, m), 5.16-5.12 (1H, dd, J=6.31, 9.35 Hz), 3.06-3.03 (1H, dd, J=6.31, 13.69 Hz), 2.99-2.94 (1H, dd, J=9.34, 13.89 Hz), 2.67-2.65 (2H, d, J=7.1 Hz), 2.11-2.07 (1H, m),1.77-1.74 (3H, m), 1.58-1.56 (1H, d, J=13.65 Hz), 1.48-

1.44 (1H, m), 1.34-1.20 (2H, m), 0.95-0.89 (2H, m). HRMS m/z calc'd for $C_{29}H_{33}N_4O_2$ 469.2604. Found 469.2619.

Example 77

3-{2-[3-(3-Amino-1H-indazol-6-yl)-phenyl]-2-[(4-aminomethyl-cyclohexanecarbonyl)-amino]-ethyl}-N-methyl-N-phenyl-benzamide 77A: Methyl 3-(2-amino-2-(3-bromophenyl)ethyl)benzoate: Compound 77A was prepared as the TFA salt according to the procedure from 1A by replacing benzylmagnesium chloride with the benzyl zinc bromide reagent prepared from methyl-3-bromomethylbenzoate and zinc metal. $^1$H NMR (CDCl$_3$ 400): 7.70 (2H, m), 7.30 (1H, s), 7.21 (5H, m), 4.08 (1H, t), 3.73 (3H, s), 2.86 (2H, m). LC/MS m/z 356.16(M+Na), 317.19 (M−NH$_3$).

77B: 3-[2-tert-Butoxycarbonylamino-2-(4'-cyano-3'-fluoro-biphenyl-3-yl)-ethyl]-benzoic acid methyl ester: Compound 77A (0.54 g, 1.62 mmol) was treated with di-tert-butyldicarbonate (0.35 g, 1.62 mmol) and triethylamine (1 mL) in anhydrous THF (10 mL). The reaction mixture was allowed to stir at rt for 4 h, quenched with water (100 mL) and organics extracted with ethyl acetate (2×25 mL), dried (MgSO$_4$), filtered and evaporated to afford methyl 3-(2-(3-bromophenyl)-2-(tert-butoxycarbonyl) ethyl) benzoate (oil, 0.48 g). The oil was re-dissolved in dioxane (25 mL) and to this solution was added 2-fluoro-4-(4,4,5,5-tetramethyl-1,3,2-dioxaborolan-2-yl)benzonitrile (0.25 g), potassium phosphate (0.5 g) and degassed for 0.5 h. Tetrakis(triphenylphosphine) palladium (0) catalyst was added and the reaction mixture was heated at 100° C. overnight. The reaction mixture was diluted with water (100 mL) and the organics extracted with ethyl acetate (2×25 mL) dried (MgSO$_4$), filtered and evaporated to a yellow oil. Purification via column chromatography on silica gel (gradient elution 10-100% ethylacetate:hexane) afforded 0.20 g of compound 77B as a colorless solid. $^1$HNMR(CDCl$_3$ 400): 7.83 (1H, J=6.4 Hz, d), 7.80 (1H, s), 7.60 (1H, t), 7.40-7.17 (6H, m), 6.60 (2H, m), 5.10 (1H, bs), 4.90 (1H, bs), 3.85 (3H, s), 3.07 (2H, J=7.1 Hz, d), 1.34 (9H, s). LC/MS m/z 497.30 (M+H)$^+$.

77C. 3-[2-{[4-(tert-Butoxycarbonylamino-methyl)-cyclohexanecarbonyl]-amino}-2-(4'-cyano-3'-fluoro-biphenyl-3-yl)-ethyl]-benzoic acid methyl ester: To a dichloromethane (1 mL) solution of compound 77B (0.18 g) was added TFA (1 mL) and the solution was allowed to stand for 2 h and concentrated.

LCMS 375.21(M+H)$^+$.

The oil was re-dissolved in anhydrous THF and to this solution was added Boc-tranexamic acid (0.07 g), BOP reagent (0.1 g) and triethylamine (0.2 mL). The reaction mixture was stirred at rt overnight, quenched with water (25 mL) and extracted with ethyl acetate (2×25 mL), dried (MgSO$_4$) and evaporated to an oil. The compound was purified via silica gel flash chromatography (gradient elution 20-100% ethylacetate:hexane) to give compound 77C as colorless solid. $^1$HNMR (CDCl$_3$ 400): 7.81 (1H, J=7.6Hz, d), 7.72 (1H, s), 7.60 (1H, m), 7.40-7.20 (9H, m), 5.71 (1H, J=6.5 Hz, d), 5.29 (1H, m), 4.60 (1H, bs), 3.83 (3H, s), 3.15 (2H, m), 2.92 (4H, m), 2.00 (2H, m), 1.65 (2H, m), 1.55 (3H, m), 1.36 (9H, s), 1.49 (2H, m).

LC/MS m/z 636.52 (M+Na)$^+$.

77D. (4-{1-(4'-Cyano-3'-fluoro-biphenyl-3-yl)-2-[3-(methyl-phenyl-carbamoyl)-phenyl]-ethylcarbamoyl}-cyclohexylmethyl)-carbamic acid tert-butyl ester: Approximately 0.1 g of compound 77C was dissolved in a solution of methanol/THF(1:1, 10 mL) and to this solution was added LiOH (0.1 g). The reaction mixture was stirred at rt overnight, quenched with water and extracted with ethylacetate (20 mL) to remove unreacted organics. The aqueous layer was acidified with HCl (1N) and organics were extracted with ethyl acetate (2×50 mL), dried (MgSO$_4$) and evaporated to a colorless solid (0.06 g). LC/MS m/z (543, M-55).

The solid was then coupled with N-methylaniline (0.02 g) in the presence of BOP reagent (0.08 g) and triethylamine (0.5 mL). LCMS determine product formation after 24 h stirring at rt. Concentration followed by purification via prep TLC (hexane:ethyl acetate 1:1, eluted several times) afforded compound 77D. LC/MS m/z 711.63(M+Na)$^+$, 689.62(M+H)$^+$, 633.51(M−55)$^+$, 589.49(M-Boc)$^+$. $^1$HNMR(CDCl$_3$400): 7.62 (1H, t), 7.40-6.85 (15H, m), 5.68 (1H, J=7.5 Hz, d), 5.30 (1H, bs), 5.10 (1H, m), 4.49 (1H, bs), 3.40 (3H, s), 3.35-3.20 (3H, m), 2.92 (6H, m), 1.90 (2H, m), 1.75 (2H, m), 1.36 (9H, s), 0.98 (2H, m). LC/MS m/z 711.63(M+Na)$^+$, 689.62(M+H)$^+$.

77E. Example 77: The title compound was prepared as the TFA salt starting with the compound from compound 77D and following the procedure from 2D. $^1$HNMR(MeOD 400): 8.45(1H, d), 7.96 (2H, d). 7.70-7.10 (14H, m), 5.10 (1H, m), 3.45 (3H, s), 3.20 (1H, m), 3.10 (2H, m), 2.20 (2H, m), 2.00-1.05 (10H, m).

LC/MS m/z 601.56 (M+H)$^+$.

Example 78

4-Aminomethyl-cyclohexanecarboxylic acid {1-[3-(2-oxo-1,2,3,4-tetrahydro-quinolin-6-yl)-phenyl]-2-phenyl-ethyl}-amide 78A. 6-(5,5-Dimethyl-[1,3,2]dioxaborinan-2-yl)-3,4-dihydro-1H-quinolin-2-one: To 6-bromo-1,2,3,4-tetrahydro-2-quinolinone (3 g, 13.0 mmol) in MeOH (65 mL) degassed with Argon was added bis(neopentylglycoloto)boron (3.29 g, 14.5 mmol), KOAc (3.25 g, 33.0 mmol) and PdCl$_2$(dppf) .CH$_2$Cl$_2$ (0.32 g, 0.39 mmol) and the reaction was heated to reflux 24 h. The reaction was concentrated, quenched with water and extracted with EtOAc (2×25 mL), washed with brine and dried (MgSO$_4$). Purification on silica gel (hexane/EtOAc then CH$_2$Cl$_2$/EtOAc) afforded 0.45 g of the boronate as a white solid. LC/MS m/z (M+H−C$_5$H$_8$)$^+$=192.

78B. Example 78: Compound 2B was converted to Example 78 according to the procedure described in Example 24, by replacing 4-(methoxy-carbonylamino) phenyl boronic acid with compound 78A. $^1$H NMR (MeOD 400) δ 8.40-8.37 (1H, d, J=8.50 Hz), 7.48-7.20 (10H, m), 6.95-6.93 (1H, d, J=8.01 Hz), 5.15-5.09 (1H, m), 3.13-3.08 (2H, m), 3.06-3.05 (2H, d, J=7.57 Hz), 2.78-2.77 (2H, d, J=7.02 Hz), 2.62-2.60 (2H, d, J=7.80 Hz), 2.23-2.20 (1H, m), 1.86-1.83 (3H, m), 1.69-1.66 (1H, d, J=13.07 Hz), 1.60 (1H, m), 1.45-1.39 (2H, m), 1.09-1.03 (2H, m).

HRMS m/z calc'd for $C_{31}H_{36}N_3O_2$ 482.2808. Found 482.2818.

Example 79

4-Aminomethyl-cyclohexanecarboxylic acid {1-[4'-(1H-imidazol-2-ylamino)-biphenyl-3-yl]-2-phenyl-ethyl}-amide 79A. {4-[1-(4'-Amino-biphenyl-3-yl)-2-phenyl-ethylcarbamoyl]-cyclohexylmethyl}-carbamic acid tert-butyl ester: Compound 2B was converted to compound 79A according to the procedure described in Example 24, by replacing 4-(methoxy-carbonylamino) phenyl boronic acid with 4-aminophenyl boronic acid.

LC/MS m/z (M+H−C$_4$H$_8$)$^+$=472.4.

79B. Example 79: To compound 79A (70 mg, 0.132 mmol) in EtOH (5 mL) was added a mixture of cyanogen bromide (20 mg) and aminoacetaldehyde diethylacetal (20 mg) and 2 drops of methanesulfonic acid and the reaction was heated to reflux 24 h. 6N HCl (15 mL) was added and the reaction was stirred 24 h and then heated to reflux 6 h. The reaction was concentrated and purified (4×) by HPLC (MeOH/H$_2$O/TFA and then CH$_3$CN/H$_2$O/TFA) to afford 2.4 mg (3%) of Example 79 as the bis-TFA salt. $^1$H NMR (MeOD 400) δ 8.49-8.47 (1H, d, J=8.40 Hz), 7.81-7.79 (2H, d, J=8.80 Hz), 7.59-7.57 (1H, d, J=8.80 Hz), 7.55-7.40 (3H, m), 7.24-7.17 (5H, m), 7.07-7.06 (1H, d, J=2.6 Hz), 7.03-7.02 (1H, d, J=2.7 Hz), 5.23-5.22 (1H, m), 3.13-3.08 (2H, m), 3.12-3.08 (2H, m), 2.76-2.75 (2H, d, J=7.0 Hz), 2.19 (1H, m), 1.84-1.81 (3H, m), 1.64 (1H, d, J=13.07 Hz), 1.60 (1H, m), 1.40-1.33 (2H, m), 1.05-1.01 (2H, m). LC/MS m/z (M+H)$^+$=494.2.

Example 80

6-Amino-N-{1-[3-(3-amino-benzo[d]isoxazol-6-yl)-phenyl]-2-phenyl-ethyl}-nicotinamide 80A. 4-(5,5-Dimethyl-[1,3,2]dioxaborinan-2-yl)-2-fluoro-benzonitrile: To 4-bromo-2-fluorobenzonitrile (15 g, 75.0 mmol) in MeOH (250 mL) were added bis(neopentylglycolato)diboron (18.6 g, 82.5 mmol), KOAc (11.0 g, 112.5 mmol), and Pd(dppf)Cl$_2$.CH$_2$Cl$_2$. The reaction was heated at reflux for 18 h. The reaction was cooled, diluted with Et$_2$O, filtered through Celite® and the filtrate was concentrated. The residue was re-dissolved in Et$_2$O, washed with water, brine and dried (MgSO$_4$). After filtration and concentration 16.89 g (97%) of an orange solid was obtained and used without further purification. $^1$H NMR (400 MHz, CDCl$_3$) δ: 7.65-7.58 (m, 3H), 3.78 (s, 4H), 1.02 (s, 6H).

80B. 3'-(1-Amino-2-phenyl-ethyl)-3-fluoro-biphenyl-4-carbonitrile: To the racemic compound from 2A (15 g, 54.3 mmol) in dioxane (500 mL) was added di-tert-butyl dicarbonate (23.7 g, 108.6 mmol) and 1N NaOH (65 mL, 65.2 mmol) and the reaction was stirred 24 h. The solvent was removed and residue dissolved in Et$_2$O, washed with 1N HCl, and dried (MgSO$_4$). A white solid 28.8 g of [1-(3-Bromo-phenyl)-2-phenyl-ethyl]-carbamic acid tert-butyl ester was obtained. LC/MS M/Z (M−C$_4$H$_8$—CO$_2$—NH$_3$+H)$^+$=259.

To [1-(3-Bromo-phenyl)-2-phenyl-ethyl]-carbamic acid tert-butyl ester (13.6 g, 36.0 mmol) was added compound 80A (16.8 g, 72.1 mmol), K$_3$PO4 (15.3 g, 72.1 mmol), DMSO (240 mL) and Pd(dppf)Cl$_2$.CH$_2$Cl$_2$ (2.6 g, 3.6 mmol). The reaction was heated to 90° C. for 18 h. The reaction was cooled, diluted with EtOAc, and washed with sat'd NaHCO$_3$, brine and dried (Na$_2$SO$_4$). A brown oil was obtained after filtration and concentration. Trituration of the oil with CH$_2$Cl$_2$/MeOH and filtration of a grey precipitate afforded after concentration 34.6 g of a brown oil that was used without further purification. LC/MS m/z (M−C$_4$H$_8$—CO$_2$—NH$_3$+H)$^+$=300.3.

To the brown oil from (34.6 g, 83.1 mmol) was added 30% TFA in CH$_2$Cl$_2$ (160 mL) and the reaction stirred 24 h. The reaction was concentrated and the residue dissolved in EtOAc and washed with sat'd NaHCO$_3$ and dried (MgSO$_4$). After filtration and concentration 15.4 g of 80B as a brown solid was obtained and was carried to next step. LC/MS m/z (M+H—NH$_3$)$^+$=300.1.

80C. 6-[3-(1-Amino-2-phenyl-ethyl)-phenyl]-benzo[d]isoxazol-3-ylamine: Compound 80B was converted to compound 80C according to the procedure described in Example 17. LC/MS m/z (M+H—NH$_3$)$^+$=313.

80D. Example 80: To 6-aminonicotinic acid (34.5 mg, 0.25 mmol), EDCI (67 mg, 0.35 mmol), HOBt (47 mg, 0.35 mmol) in a 2 dram vial was added compound 80C (49.4 mg, 0.15 mmol), TEA (35 μL, 0.25 mmol) and DMF (1 mL). The reaction was shaken 24 h. The reaction was purified by silica gel chromatography (ISCO) to afford Example 80. LC/MS m/z (M+H)$^+$450.

Table 1 and Table 2 below summarize representative examples, the synthesis of which is described above, of the compounds in the present invention. Examples 18-23, 25-40, 42-61, 63-65, 68-71, 73-74, 76, and 81 were prepared using procedures similar to those described above.

TABLE 1

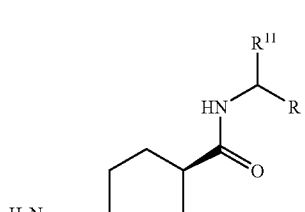

(Id)

| Ex # | R$^{11}$ | R | MS (M + H)$^+$ |
|---|---|---|---|
| 1 | Bn | 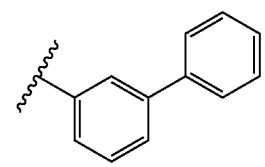 | 413.4 |

TABLE 1-continued (Id)

| Ex # | R[11] | R | MS (M + H)[+] |
|---|---|---|---|
| 2 | Bn | 3-(1H-indazol-3-amin-6-yl)phenyl | 468.4 |
| 3 | Bn | 3-bromo-5-(1H-indazol-3-amin-6-yl)phenyl | 546.4<br>548.4 |
| 4 | Bn | 3-methyl-5-(1H-indazol-3-amin-6-yl)phenyl | 482.5 |
| 5 | Bn | 3-ethyl-5-(1H-indazol-3-amin-6-yl)phenyl | 496.5 |
| 6 | Bn | 3-amino-5-(1H-indazol-3-amin-6-yl)phenyl | 483.5 |

TABLE 1-continued (Id)

| Ex # | R11 | R | MS (M + H)+ |
|---|---|---|---|
| 7 | Bn | 3-hydroxy-5-(3-amino-1H-indazol-6-yl)phenyl | 484.5 |
| 8 | Bn | 4-methoxy-3-(3-amino-1H-indazol-6-yl)phenyl | 498.5 |
| 9 | Bn | 4-hydroxy-3-(3-amino-1H-indazol-6-yl)phenyl | 484.5 |
| 10 | Bn | 2-methoxy-5-(3-amino-1H-indazol-6-yl)phenyl | 498.5 |
| 11 | Bn | 2-hydroxy-5-(3-amino-1H-indazol-6-yl)phenyl | 484.5 |
| 12 | Bn | 2-chloro-5-(3-amino-1H-indazol-6-yl)phenyl | 502.4, 504.4 |

TABLE 1-continued (Id)

| Ex # | R¹¹ | R | MS (M + H)⁺ |
|---|---|---|---|
| 13 | Bn (S-enantiomer) | 3-(3-amino-1H-indazol-6-yl)phenyl | 468.4 |
| 14 | Bn (R-enantiomer) | 3-(3-amino-1H-indazol-6-yl)phenyl | 468.4 |
| 15 | -C(CH₃)₂C(O)NHCH₂-(2-pyridyl) | 3-(3-amino-1H-indazol-6-yl)phenyl | 512.3 |
| 16 | Bn | 3-(3-amino-1H-indazol-6-yl)-2-hydroxyphenyl | 484.3 |
| 17 | Bn (S-enantiomer) | 3-(3-amino-1,2-benzisoxazol-6-yl)phenyl | 469.3 |
| 18 | Bn | 5-(3-amino-1H-indazol-6-yl)-2-fluorophenyl | 486.4 |

TABLE 1-continued
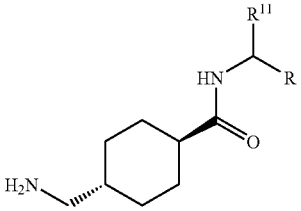
(Id)
| Ex # | R¹¹ | R | MS (M + H)⁺ |
|---|---|---|---|
| 19 | Bn | 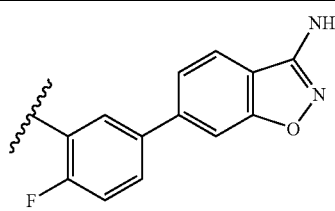 | 487.3 |
| 20 | Bn | 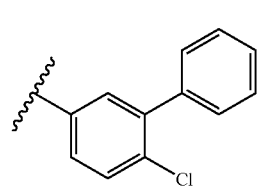 | 431.4 |
| 21 | Bn | 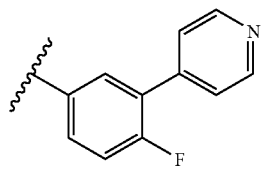 | 447.3<br>449.3 |
| 22 | Bn | 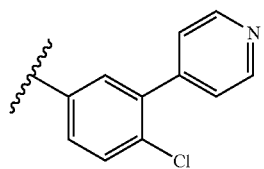 | 432.4 |
| 23 | Bn | 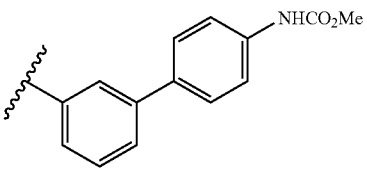 | 448.3<br>450.3 |
| 24 | Bn | 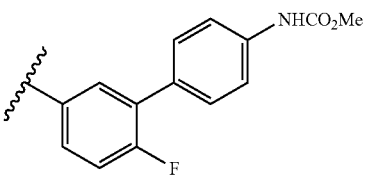 | 486.4 |
| 25 | Bn |  | 504.4 |

TABLE 1-continued
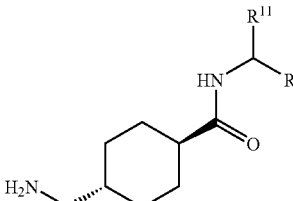
(Id)
| Ex # | R[11] | R | MS (M + H)+ |
|---|---|---|---|
| 26 | Bn | 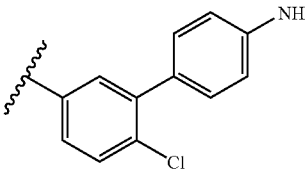 | 520.4<br>522.4 |
| 27 | Bn | 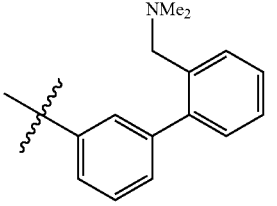 | 436.3<br>438.3 |
| 28 | Bn | 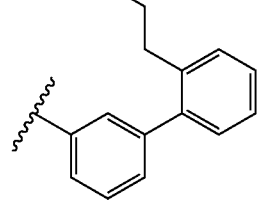 | 470.3 |
| 29 | Bn | 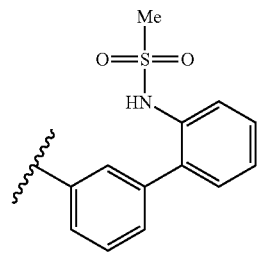 | 485.4 |
| 30 | Bn | 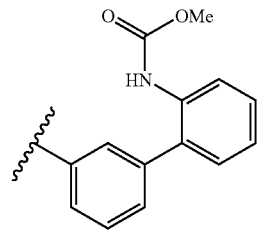 | 506.4 |
| 31 | Bn | | 486.4 |

TABLE 1-continued
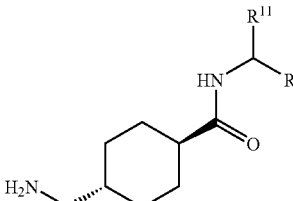
(Id)
| Ex # | R[11] | R | MS (M + H)+ |
|---|---|---|---|
| 32 | Bn | 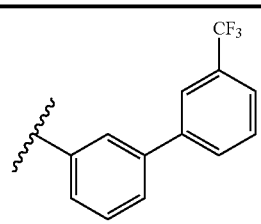 3'-CF3-biphenyl | 481.3 |
| 33 | Bn | 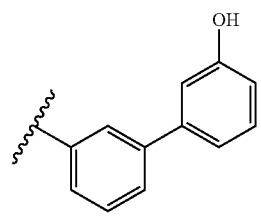 3'-OH-biphenyl | 429.3 |
| 34 | Bn | 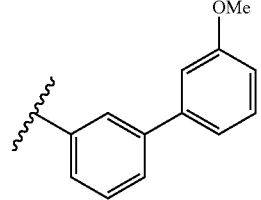 3'-OMe-biphenyl | 443.4 |
| 35 | Bn | 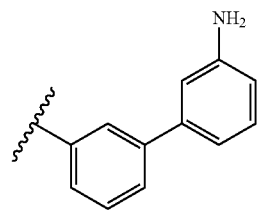 3'-NH2-biphenyl | 428.4 |
| 36 | Bn | 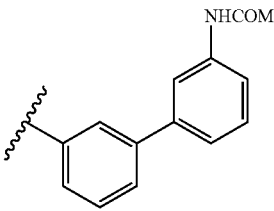 3'-NHCOMe-biphenyl | 470.3 |
| 37 | Bn | 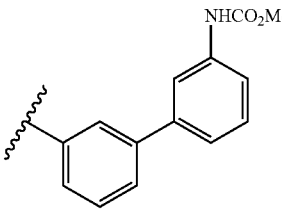 3'-NHCO2Me-biphenyl | 486.4 |

TABLE 1-continued
(Id)
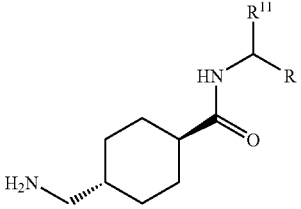
| Ex # | R[11] | R | MS (M + H)+ |
|---|---|---|---|
| 38 | Bn | 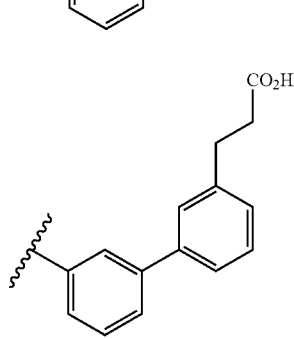 3'-(NHSO$_2$Me)-biphenyl-3-yl | 506.4 |
| 39 | Bn | 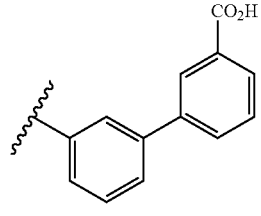 3'-(CH$_2$CH$_2$CO$_2$H)-biphenyl-3-yl | 485.4 |
| 40 | Bn | 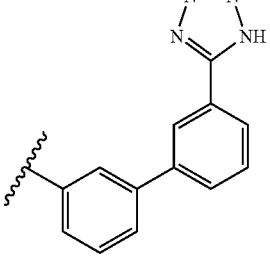 3'-(CO$_2$H)-biphenyl-3-yl | 457.2 |
| 41 | Bn | 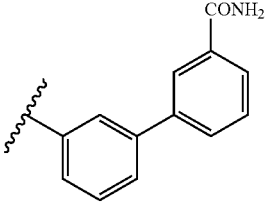 3'-(1H-tetrazol-5-yl)-biphenyl-3-yl | 481.4 |
| 42 | Bn | 3'-(CONH$_2$)-biphenyl-3-yl | 498.3 |

TABLE 1-continued
(Id)
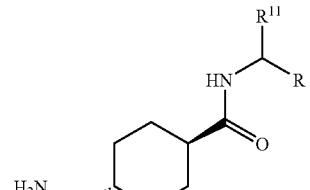
| Ex # | R[11] | R | MS (M + H)+ |
|---|---|---|---|
| 43 | Bn | 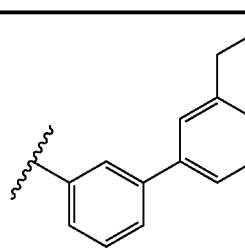 | 470.4 |
| 44 | Bn | 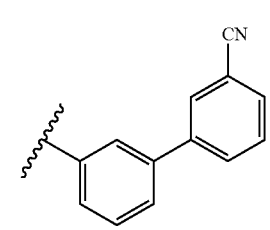 | 438.3 |
| 45 | Bn |  | 443.2 |
| 46 | Bn | 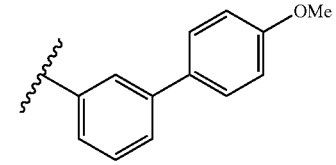 | 443.3 |
| 47 | Bn |  | 457.4 |
| 48 | Bn | 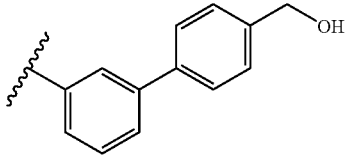 | 442.4 |
| 49 | Bn |  | 500.3 |

TABLE 1-continued
(Id)
| Ex # | R[11] | R | MS (M + H)+ |
|---|---|---|---|
| 50 | Bn | 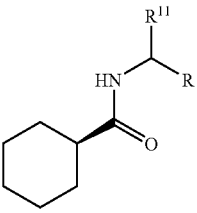 | 452.3 |
| 51 | Bn | 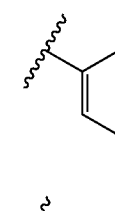 | 470.4 |
| 52 | Bn | 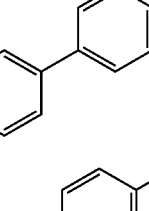 | 471.4 |
| 53 | Bn | 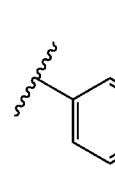 | 485.3 |
| 54 | Bn | 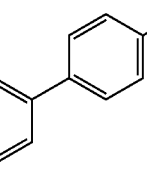 | 498.3 |
| 55 | Bn | 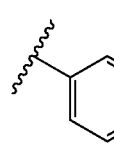 | 491.1 |
| 56 | Bn | 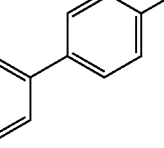 | 470.4 |

TABLE 1-continued
(Id)
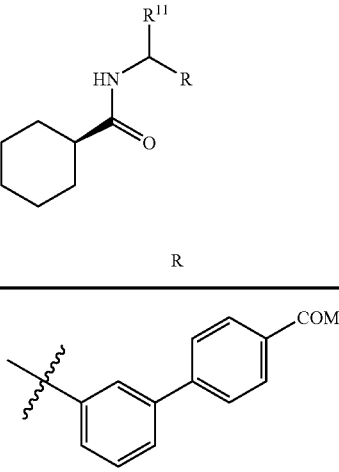
| Ex # | R[11] | R | MS (M + H)[+] |
|---|---|---|---|
| 57 | Bn | 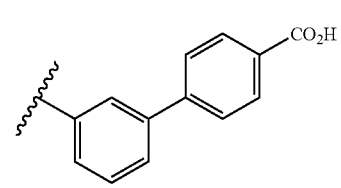 3'-biphenyl-4'-COMe | 455.3 |
| 58 | Bn | 3'-biphenyl-4'-CO₂H | 457.2 |
| 59 | Bn | 3'-biphenyl-4'-CONH₂ | 456.2 |
| 60 | Bn | 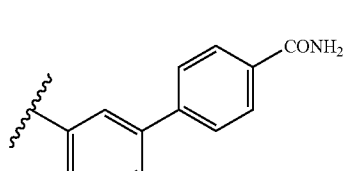 3'-biphenyl-3',4'-diCl | 481.3 |
| 61 | Bn | 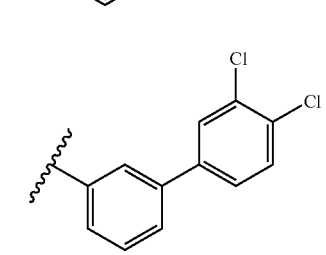 3'-biphenyl-3'-CO₂Me-4'-NH₂ | 486.3 |
| 62 | Bn | 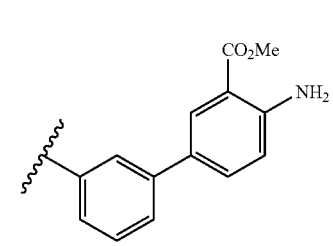 3'-biphenyl-3'-CO₂H-4'-NH₂ | 472.2 |

TABLE 1-continued (Id)

| Ex # | R[11] | R | MS (M + H)+ |
|---|---|---|---|
| 63 | Bn | 3-(3-carboxy-4-(methoxycarbonylamino)phenyl)phenyl | 530.33 |
| 64 | Bn | 3-(3-carboxy-4-(acetylamino)phenyl)phenyl | (M − H)⁻ = 512.4 |
| 65 | Bn | 3-(3-amino-5-carboxyphenyl)phenyl | 472.4 |
| 66 | Bn | 3-(6-aminopyridin-3-yl)phenyl | 429.3 |
| 67 | Bn | 3-(6-(methoxycarbonylamino)pyridin-3-yl)phenyl | 487.4 |
| 68 | Bn | 3-(5-(methoxycarbonyl)thiophen-2-yl)phenyl | 477.4 |
| 69 | Bn | 3-(5-carboxythiophen-2-yl)phenyl | 463.3 |

TABLE 1-continued
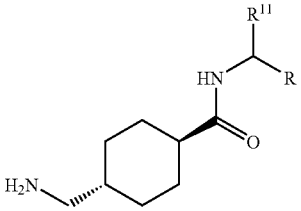
(Id)
| Ex # | R[11] | R | MS (M + H)+ |
|---|---|---|---|
| 70 | Bn | 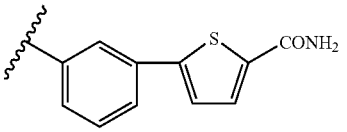 | 462.4 |
| 71 | Bn | 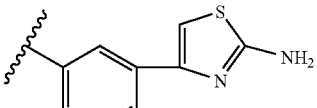 | 487.3 |
| 72 | Bn | 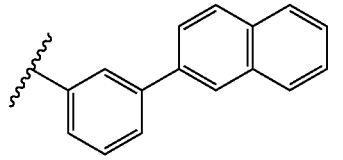 | 435.3 |
| 73 | Bn | 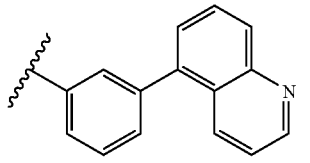 | 436.4 |
| 74 | Bn | 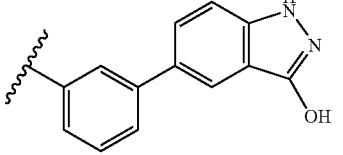 | 463.3 |
| 75 | Bn | 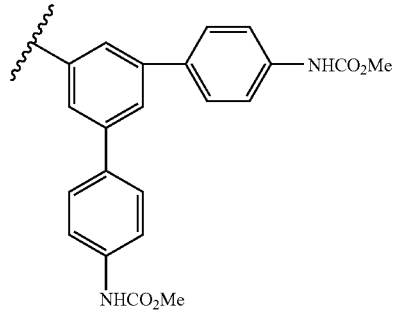 | 469.3 |
| 76 | Bn |  | 635.5 |

TABLE 1-continued (Id)

| Ex # | R¹¹ | R | MS (M + H)⁺ |
|---|---|---|---|
| 77 | N-methyl-N-phenyl-3-(methylene)benzamide | 3-(3-amino-1H-indazol-6-yl)phenyl | 601.6 |
| 78 | Bn | 3-(2-oxo-1,2,3,4-tetrahydroquinolin-6-yl)phenyl | 482.2 |
| 79 | Bn | 4'-(1H-imidazol-2-ylamino)biphenyl-3-yl | 494.2 |

TABLE 2

| Ex # | A | MS (M + H)⁺ |
|---|---|---|
| 80 | 6-amino-pyridin-3-yl | 450 |
| 81 | quinolin-2-yl | 485.3 |

Utility

The compounds of this invention are inhibitors of factor XIa and are useful as anticoagulants for the treatment or prevention of thromboembolic disorders in mammals (i.e., factor XIa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but not limited to: prosthetic valves, indwelling catheters, stents, and vessel grafts. The procedures include, but not limited to: cardiopulmonary bypass and hemodialysis. It is noted that thrombosis includes occlusion (e.g. after a bypass) and reocclusion (e.g., during or after percutaneous transluminal coronary angioplasty). The term "stroke", as used herein, refers to embolic stroke or atherothrombotic stroke arising from occlusive thrombosis in the carotid communis, carotid interna, or intracerebral arteries. The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade and/or contact activation system, more specifically, inhibition of the coagulation factors: factor XIa, factor VIIa, factor IXa, factor Xa, plasma kallikrein or thrombin.

The compounds of this invention also are inhibitors of plasma kallikrein and are useful as anti-inflammatory agents for the treatment or prevention of diseases associated with an activation of the contact activation system (i.e., plasma kallikrein associated disorders). In general, a contact activation system disorder is a disease caused by activation of blood on artificial surfaces, including prosthetic valves or other implants, indwelling catheters, stents, cardiopulmonary bypass, hemodialysis, microorganism (e.g., bacteria, virus), or other procedures in which blood is exposed to an artificial surface that promotes contact activation, blood clots (i.e., diseases involving fibrin formation, platelet activation, and/or platelet aggregation). It also includes systemic inflammatory response syndrome, sepsis, acute respiratory distress syndrome, hereditary angioedema or other inherited or acquired deficiencies of contact activation components or their inhibitors (plasma kallikrein, factor XIIa, high molecular weight kininogen, C1-esterase inhibitor). It may also include acute and chronic inflammations of joints, vessels, or other mammalian organs.

The effectiveness of compounds of the present invention as inhibitors of the coagulation factors XIa, VIIa, IXa, Xa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin, which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. In general, preferred compounds of the present invention, such as the particular compounds disclosed in the above examples, have been identified to be active and exhibit $K_i$'s of equal to or less than 15 µM in the Factor XIa assay, thereby demonstrating the utility of the compounds of the present invention as especially effective inhibitors of coagulation Factor XIa. More preferred compounds have $K_i$'s of equal to or less than 5 µM, preferably equal to or less than 1 µM, more preferably equal to or less than 0.5 µM.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. In general, compounds tested in the Factor VIIa assay are considered to be active if they exhibit a $K_i$ of equal to or less than 15 µM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M. In general, compounds tested in the Factor IXa assay are considered to be active if they exhibit a $K_i$ of equal to or less than 15 µM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.0003 M. In general, compounds tested in the Factor Xa assay are considered to be active if they exhibit a $K_i$ of equal to or less than 15 µM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; Chromogenix) at a concentration of 0.00008-0.0004 M. The Km value used for calculation of Ki was 0.00005 to 0.00007 M. In general, Compounds tested in the plasma kallikrein assay are considered to be active if they exhibit a $K_i$ of equal to or less than 15 µM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. In general, compounds tested in the thrombin assay are considered to be active if they exhibit a $K_i$ of equal to or less than 15 µM.

In general, preferred compounds of the present invention have demonstrated $K_i$ values of equal to or less than 15 µM in at least one of the above assays, thereby confirming the utility of the compounds of the present invention as effective inhibitors of the coagulation cascade and/or contact activation system, and useful as anticoagulants for the prevention or treatment of thromboembolic disorders in mammals and/or as anti-inflammatory agents for the prevention or treatment of inflammatory disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$(v_o-v_s)/v_s=I/(K_i(1+S/K_m))$ for a competitive inhibitor with one binding site; or $v_s/v_o=A+((B-A)/1+((IC_{50}/(I)^n)))$ and $K_i=IC_{50}/(1+S/K_m)$ for a competitive inhibitor where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The effectiveness of compounds of the present invention as inhibitors of the coagulation factors XIa, VIIa, IXa, Xa, or thrombin, can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis Model:

The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-Venous Shunt Thrombosis Model:

The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The anti-inflammatory effect of these compounds can be demonstrated in an Evans Blue dye extravasation assay using C1-esterase inhibitor deficient mice. In this model, mice are dosed with a compound of the present invention, Evans Blue is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The utility of the compounds of the current invention to reduce or prevent the morbidity and/or mortality of sepsis can be assessed by injecting a mammalian host with bacteria or viruses or extracts there of and compounds of the present invention. Typical read-outs of the efficacy include changes in the LD50 and blood pressure preservation.

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents, anti-platelet or platelet inhibitory agents, anti-inflammatory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX™), aprotinin, synthetic pentasaccharide, direct acting thrombin inhibitors including hirudin and argatroban, as well as other factor VIIa, VIIIa, IXa, Xa, XIa, thrombin, TAFI, and fibrinogen inhibitors known in the art.

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril); angiotensin-II receptor antagonists (e.g., irbestatin, losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual ACE/NEP inhibitors, e.g., omapatrilat, gemopatrilat, nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending-upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences,* Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (I):

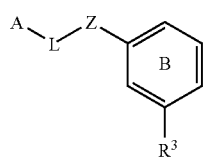

or a stereoisomer, a tautomer, a pharmaceutically acceptable salt thereof, wherein:

A is cyclohexyl substituted with 0-1 $R^1$ and 0-3 $R^2$; provided that A is other than cyclohexyl substituted with CN;

ring B is phenyl optionally further substituted with 0-3 $R^4$;

Z is —$CHR^{11}$—;

L is —$C(O)NR^{10}$—;

$R^1$ is, independently at each occurrence, H, —$NH_2$, —NH($C_{1-3}$ alkyl), —$(CH_2)_rNR^7R^8$, —$CH(C_{1-4}$ alkyl)$NH_2$, —$CH(C_{1-4}$ alkyl)$_2NH_2$, —$N(C_{1-3}$ alkyl)$_2$, —$C(=NH)NH_2$, —$C(O)NH_2$, —$CH_2NH_2$, —$CH_2NH(C_{1-3}$ alkyl), —$CH_2N(C_{1-3}$ alkyl)$_2$, —$CH_2CH_2NH_2$, —$CH_2CH_2NH(C_{1-3}$ alkyl), —$CH_2CH_2N(C_{1-3}$ alkyl)$_2$, $OCF_3$, $CF_3$, $OR^a$, $SR^a$, CN or $C_{1-6}$ alkyl;

$R^2$ is, independently at each occurrence, H, =O, $CF_3$, $OCF_3$, $CHF_2$, CN, $NO_2$, $OR^a$, $SR^a$, —$NR^7R^8$, or $C_{1-6}$ alkyl;

$R^3$ is a heterocycle selected from: benzisoxazole, indazole, quinoline, tetrahydroquinoline, phthalazine, and quinazoline, wherein said heterocycle is substituted with 0-3 $R^{3a}$;

$R^{3a}$ is, independently at each occurrence, =O, F, Cl, Br, I, $OCF_3$, $CF_3$, —$(CH_2)_rCN$, $NO_2$, —$(CH_2)_rOR^{3b}$, —$(CH_2)_r—SR^{3b}$, —$(CH_2)_rNR^7R^8$, —$C(O)C_{1-4}$ alkyl, —$SO_2NHR^{3b}$, —$(CH_2)_rNR^8CO_2R^{3b}$, —$(CH_2)_rS(O)_pNR^8R^9$, —$S(O)R^{3c}$, —$S(O)_2R^{3c}$, —$(CH_2)_rCO_2R^{3b}$, —$(CH_2)_rC(O)NR^8R^9$, $C_{1-4}$ haloalkyl, $C_{1-4}$ haloalkyloxy-, or $C_{1-6}$ alkyl;

$R^{3b}$ is, independently at each occurrence, H, or $C_{1-6}$ alkyl;

$R^{3c}$ is, independently at each occurrence, $C_{1-6}$ alkyl $R^4$ is, independently at each occurrence, H, F, Cl, Br, I, $OCF_3$, $CF_3$, CN, $NO_2$, $OR^a$, $SR^a$, —$C(O)R^a$, —$C(O)OR^a$, —$OC(O)R^a$, —$NR^7R^8$, —$C(O)NR^8R^9$, —$NR^8C(O)R^b$, —$NR^8C(O)OR^b$, —$S(O)R^c$, —$S(O)_2R^c$, or $C_{1-6}$ alkyl $R^7$ is, independently at each occurrence, H, $C_{1-4}$ alkyl, —$C(O)(C_{1-4}$ alkyl), or —$(CH_2)_n$-phenyl;

$R^8$ is, independently at each occurrence, H, $C_{1-6}$ alkyl, or —$(CH_2)_n$-phenyl;

$R^9$ is, independently at each occurrence, H, $C_{1-6}$ alkyl, or —$(CH_2)_n$-phenyl;

$R^{10}$ is, independently at each occurrence, H, or $C_{1-6}$ alkyl substituted with 0-2 F;

$R^{11}$ is —$(CH_2)_s$-phenyl substituted with 0-2 $R^{11b}$;

$R^{11b}$ is, independently at each occurrence, H, $OR^a$, $SR^a$, F, Cl, Br, CN, $NO_2$, $CF_3$, $OCF_3$, $OCHF_2$, —$NR^7R^8$, —$C(O)R^a$, —$C(O)OR^a$, —$C(O)NR^7R^8$, —$CH_2OR^a$, —$CH_2NR^7R^8$, —$NR^8C(O)R^b$, —$S(O)_pNR^8R^9$, —$NR^8S(O)_pR^c$, —$S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy;

$R^a$ is, independently at each occurrence, H, $CF_3$, $C_{1-6}$ alkyl, —$(CH_2)_r—C_{3-7}$ cycloalkyl, or —$(CH_2)_r—C_{6-10}$ aryl;

$R^b$ is, independently at each occurrence, $CF_3$, OH, $C_{1-4}$ alkoxy, or $C_{1-6}$ alkyl;

$R^c$ is, independently at each occurrence, $CF_3$, or $C_{1-6}$ alkyl;

r, at each occurrence, is selected from 0, 1, 2, 3, and 4;

n, at each occurrence, is selected from 0, 1, 2, 3, and 4;

p, at each occurrence, is selected from 0, 1, and 2; and s, at each occurrence, is selected from 1, 2, 3, and 4.

2. A compound according to claim 1, wherein:

$R^1$ is, independently at each occurrence, Me, Et, $CF_3$, OMe, OH, —$NH_2$, —$C(=NH)NH_2$, —$C(O)NH_2$, or —$CH_2NH_2$;

$R^3$ is a heterocycle substituted with 0-2 $R^{3a}$, wherein said heterocycle is selected from: benzisoxazole, quinazoline, phthalazine, quinoline, 3H-quinazolin-4-one, 2H-phthalazin-1-one, 1H-quinolin-4-one, 1H-quinolin-2-one, and 1,2,3,4-tetrahydroquinoline;

$R^{3a}$ is, independently at each occurrence, F, Cl, Br, Me, CN, OH, OMe, —$CH_2OH$, —$CH_2OMe$, $CF_3$, COMe, $CO_2H$, $CO_2Me$, —$CH_2CO_2H$, —$(CH_2)_2CO_2H$, —$CH_2CO_2Me$, —$CH_2CO_2Et$, —$CH_2CN$, $NH_2$, —$CH_2NH_2$, —$CH_2NMe_2$, —$NHC(O)Me$, —$NHCO_2Me$, —$NHCO_2Et$, —$NHCO_2Bn$, —$NHCO_2iBu$, —$CH_2NHCO_2Me$, —$NHSO_2Me$, —$SO_2NH_2$, —$SO_2NHMe$, —$CONH_2$, —$CONHMe$, —$CON(Me)_2$, —$CH_2CONH_2$, or —$C(=NH)NH_2$; and $R^4$ is, independently at each occurrence, H, F, Cl, Br, OH, OMe, $NH_2$, Me, Et, $CF_3$, —$CH_2OH$, —$(CH_2)_2OH$, —$(CH_2)_3OH$, —$CH_2NH_2$, —$(CH_2)_2NH_2$, —$(CH_2)_3NH_2$, —$C(O)_2H$, —$C(O)NH_2$, —$C(O)NHMe$, —$C(O)N(Me)_2$, —$CH_2CO_2H$, —$CH_2C(O)NH_2$, —$NHC(O)Me$ or —$NHCO_2Me$.

3. A compound according to claim 1, wherein:

$R^{11}$ is —$CH_2$-phenyl substituted with 0-2 $R^{11b}$; and $R^{11b}$ is, independently at each occurrence, H, F, Cl, Br, OMe, $C_{1-4}$ alkyl, $OCF_3$, $OCHF_2$, OPh, OBn, $NO_2$, —$NH_2$, —$CO_2H$, —$CO_2Me$, —$CONH_2$, —$C(O)Ph$, —$C(O)NMePh$, —$C(O)NHPh$, —$NHC(O)Me$, —$NHC(O)CH_2Ph$, —$NMeC(O)Ph$, —$NHC(O)CH_2CH_2Ph$, —$NHS(O)_2Ph$, —$NMeS(O)_2Ph$, —$S(O)_2NMePh$, or $CF_3$.

4. A compound according to claim 3, wherein:

A is 4-aminomethyl-cyclohexyl, or 4-methyl-cyclohexyl; and $R^3$ is 3-$NH_2$-benzisoxazol-5-yl, 3-$NH_2$-benzisoxazol-6-yl, 3-$NH_2$-indazol-5-yl, 3-$NH_2$-indazol-6-yl, 3-OH-indazol-5-yl, 3-OH-indazol-6-yl, quinolin-5-yl, 1-$NH_2$-phthalazin-6-yl, 4-$NH_2$-quinazolin-7-yl, 2-Me-4-$NH_2$-quinazolin-7-yl, 2,4-di-$NH_2$-quinazolin-7-yl,

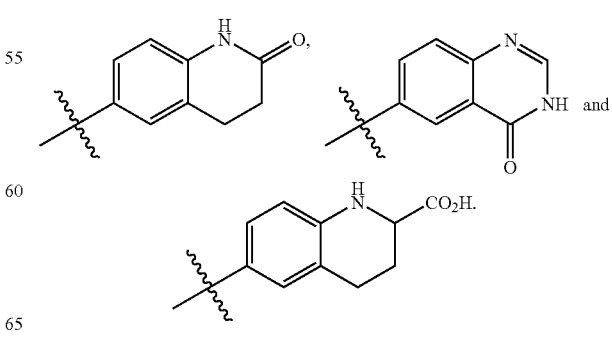

5. A compound according to claim 4, wherein:

A is 4-aminomethyl-cyclohexyl;

R³ is 3-NH₂-indazol-6-yl, 3-NH₂-benzisoxazol-6-yl, quinolin-5-yl, 3-OH-indazol-5-yl, or

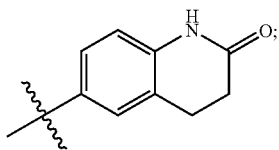

R⁴ is, independently at each occurrence, H, F, Cl, Br, OH, OMe, NH₂, Me or Et ; and R¹¹ is benzyl or 3-[C(O)NMePh]-benzyl.

6. A compound according to claim 1, wherein the compound is the (S)-enantiomer.

7. A compound of Formula (Id):

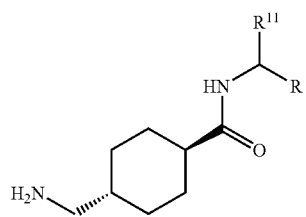

or a stereoisomer, a pharmaceutically acceptable salt thereof, wherein:

R₁₁ is benzyl or 3-[C(O)NMePh]-benzyl;

R is

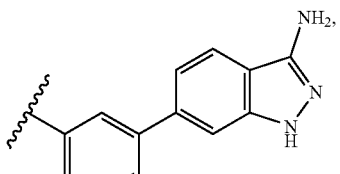

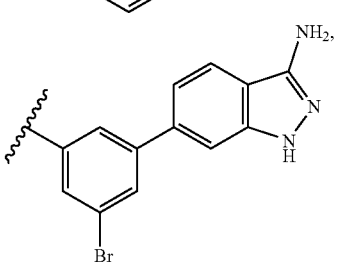

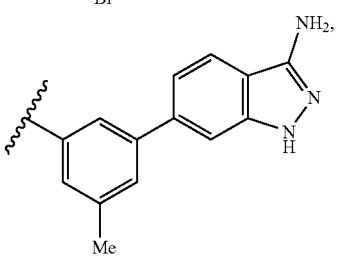

-continued

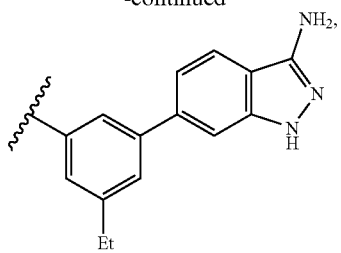

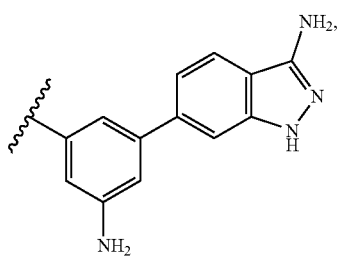

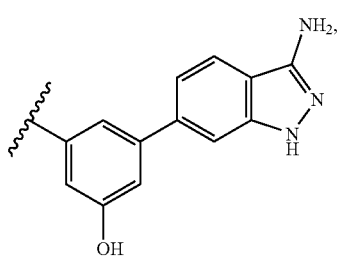

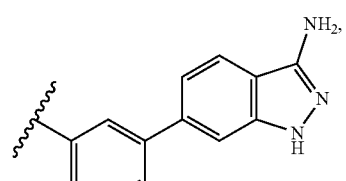

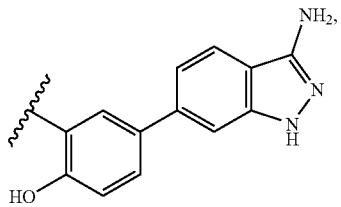

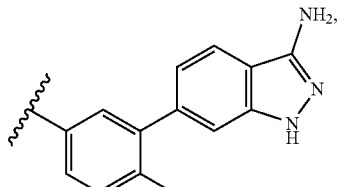

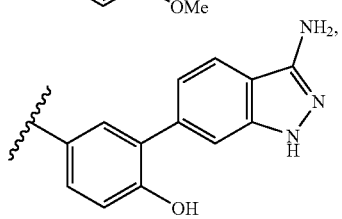

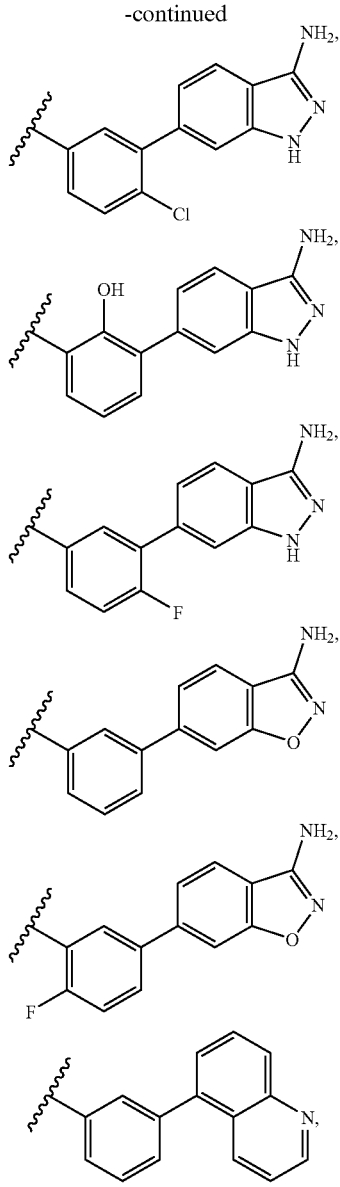

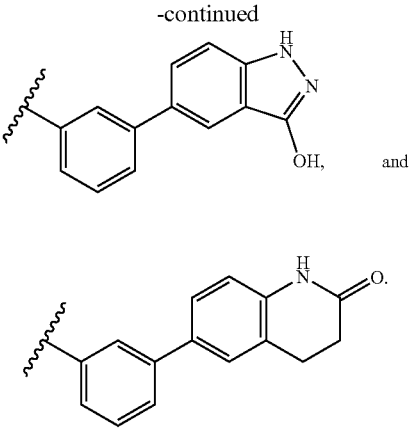

8. A pharmaceutical composition, comprising: a pharmaceutically acceptable carrier and a therapeutically effective amount of a compound of claim 1.

9. A pharmaceutical composition, comprising: a pharmaceutically acceptable carrier and a therapeutically effective amount of a compound of claim 2.

10. A pharmaceutical composition, comprising: a pharmaceutically acceptable carrier and a therapeutically effective amount of a compound of claim 3.

11. A pharmaceutical composition, comprising: a pharmaceutically acceptable carrier and a therapeutically effective amount of a compound of claim 4.

12. A pharmaceutical composition, comprising: a pharmaceutically acceptable carrier and a therapeutically effective amount of a compound of claim 5.

13. A pharmaceutical composition, comprising: a pharmaceutically acceptable carrier and a therapeutically effective amount of a compound of claim 6.

14. A pharmaceutical composition, comprising: a pharmaceutically acceptable carrier and a therapeutically effective amount of a compound of claim 7.

* * * * *